United States Patent
Wright et al.

(10) Patent No.: US 10,167,483 B2
(45) Date of Patent: *Jan. 1, 2019

(54) HERBICIDE RESISTANCE GENES

(71) Applicant: Dow AgroSciences LLC, Indianapolis, IN (US)

(72) Inventors: Terry R. Wright, Carmel, IN (US); Justin M. Lira, Zionsville, IN (US); Terence Anthony Walsh, Zionsville, IN (US); Donald Merlo, Carmel, IN (US); Jayakumar Pon Samuel, Carmel, IN (US); Gaofeng Lin, Zionsville, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 527 days.

This patent is subject to a terminal disclaimer.

(21) Appl. No.: 14/491,197

(22) Filed: Sep. 19, 2014

(65) Prior Publication Data

US 2015/0080218 A1 Mar. 19, 2015
US 2017/0009214 A9 Jan. 12, 2017

Related U.S. Application Data

(63) Continuation of application No. 13/647,081, filed on Oct. 8, 2012, now Pat. No. 8,916,752, which is a continuation of application No. 12/091,896, filed as application No. PCT/US2006/042133 on Oct. 27, 2006, now Pat. No. 8,283,522.

(60) Provisional application No. 60/731,044, filed on Oct. 28, 2005.

(51) Int. Cl.
*C12N 15/82* (2006.01)
*C12N 9/02* (2006.01)

(52) U.S. Cl.
CPC ....... *C12N 15/8274* (2013.01); *C12N 9/0069* (2013.01); *C12N 9/0071* (2013.01); *C12N 15/8275* (2013.01); *C12Y 113/11* (2013.01)

(58) Field of Classification Search
CPC .................................................. C12N 9/0071
See application file for complete search history.

(56) References Cited

U.S. PATENT DOCUMENTS

| | | | |
|---|---|---|---|
| 4,683,195 A | 7/1987 | Mullis et al. | |
| 4,761,373 A | 8/1988 | Anderson et al. | |
| 5,608,147 A * | 3/1997 | Kaphammer | C12N 9/0004 435/410 |
| 5,656,422 A * | 8/1997 | Crawford | C12Q 1/26 435/174 |
| 6,645,497 B2 | 11/2003 | Malvar et al. | |
| 6,664,384 B1 * | 12/2003 | Xu | C12N 15/8216 435/320.1 |
| 7,205,561 B2 | 4/2007 | Chelvayohan et al. | |
| 7,250,561 B1 * | 7/2007 | Pallett | C12N 9/0069 435/320.1 |
| 8,278,505 B2 * | 10/2012 | Lira | C12N 9/0004 435/419 |
| 8,283,522 B2 * | 10/2012 | Wright | C12N 9/0069 435/419 |
| 8,916,752 B2 * | 12/2014 | Wright | C12N 9/0069 435/419 |
| 9,062,284 B2 * | 6/2015 | Lira | C12N 9/0004 |

FOREIGN PATENT DOCUMENTS

WO WO 2003/034813 5/2003
WO WO 2005/107437 11/2005
WO WO 2007/053482 5/2007

OTHER PUBLICATIONS

Schleinitz et al Sep. 2004, Applied and Environmental Microbiology 70(9): 5357-5365.*
Fourgoux-Nicol et al 1999, Plant Molecular Biology 40: 857-872.*
Maliga 2002, Current Opinion in Plant Biology 5: 164-172.*
Schleinitz, et al., Localization and Characterization of two Novel Genes Encoding Stereospecific Diosygenases Catalyzing 2(2,4-Dichlorophenoxy)propionate Cleavage in *Delftia acidovorans* MCI, Applied and Environmental Microbiology, Sep. 2004, vol. 70, p. 5357-5365.
Gressel, Jonathan, Molecular biology of weed control, Transgenic Research 2000, vol. 9, p. 355-382.
Hegg, Eric L. et al., Herbicide-Degrading α-Keto Acid-Dependent Enzyme TfdA: Metal Coordination Environment and Mechanistic Insights, Biochemistry, 1999, vol. 38, p. 16714-16726.
Perlack, Frederick J., Modification of the Coding Sequence Enhances Plant Expression of Insect Control Protein Genes, *Proc. Natl., Acad. Sci.*, USA, Biochemistry, Apr. 1991, vol. 88, p. 3324-3328.
Kasuga, Mie, Improving Plant Drought, Salt, and Freezing Tolerance by Gene Transfer of a Single Stress-Inducible Transcription Factor, Nature Biotechnology, Mar. 1999, vol. 17, p. 287-291.

(Continued)

*Primary Examiner* — David H Kruse
(74) *Attorney, Agent, or Firm* — Barnes & Thornburg LLP

(57) ABSTRACT

The subject invention provides novel plants that are not only resistant to 2,4-D, but also to pyridyloxyacetate herbicides. Heretofore, there was no expectation or suggestion that a plant with both of these advantageous properties could be produced by the introduction of a single gene. The subject invention also includes plants that produce one or more enzymes of the subject invention "stacked" together with one or more other herbicide resistance genes. The subject invention enables novel combinations of herbicides to be used in new ways. Furthermore, the subject invention provides novel methods of preventing the development of, and controlling, strains of weeds that are resistant to one or more herbicides such as glyphosate. The preferred enzyme and gene for use according to the subject invention are referred to herein as AAD-12 (AryloxyAlkanoate Dioxygenase). This highly novel discovery is the basis of significant herbicide tolerant crop trait and selectable marker opportunities.

25 Claims, 3 Drawing Sheets

Specification includes a Sequence Listing.

(56) References Cited

OTHER PUBLICATIONS

Verdaguer, Bertrand, Isolation and Expression in Transgenic Tobacco and Rice Plants, of the Cassava Vein Mosaic Virus (CVMV) Promoter, Plant Molecular Biology, 1996, vol. 31, p. 1129-1139.

Westendorf, et al., Purification and Characterisation of the Enantiospecific Dioxygenases from Delftia acidovorans MC1 Initiating the Degradation of Phenoxypropionate and Phenoxyacetate Herbicides, Acta Biotechnol. 2003, vol. 23, p. 3-17.

Fourgoux-Nicol et al., Isolation of rapeseed genes expressed early and specifically during development of the male gametophyte, Plant Biology, 1999, vol. 40, p. 857-872.

Iowa State University Extension 2005 Herbicide manual for Agricultural Professionals, p. 50-72.

Halford et al., Weed Technology, 2001, vol. 15, p. 737-744.

Muller et al., "Purification and Characterization of Two Enantioselective α-Ketoglutarate-Dependent Dioxygenases, RdpA and SdpA, from Sphingomonas herbicidovorans MH," Appl. Environ. Microbiol., 72(7):4853-61 (2006).

Schleinitz et al., "Delftia acidovorans plasmid pMC1, partial sequence," Appl. Environ. Microbiol. 70 (9), 5357-5365, Genbank accession No. AY327575 (2004).

Westendorf et al., "The two enantiospecific dichlorprop/α-ketoglutarate-dioxygenases from Delftia acidovorans MC1—protein and sequence data of RdpA and SdpA," Microbiol. Res.157: 317-322 (2002).

Wright et al., "Robust crop resistance to broadleaf and grass herbicides provided by aryloxyalkanoate dioxygenase transgenes," Natl. Acad. Sci., 107(47): 20240-5 (2010).

\* cited by examiner

FIG. 2

SEQUENCE LISTING

<160> NUMBER OF SEQ ID NOS: 21

<210> SEQ ID NO 1
<211> LENGTH: 879
<212> TYPE: DNA
<213> ORGANISM: Delftia acidovorans

<400> SEQUENCE: 1

```
atgcagacga cgctgcagat taccccaca ggcgccaccc tgggcgccac cgtcaccggc      60
gtgcacctgg ccacgctgga cgacgccggc ttcgccgccc tgcacgccgc ctggctgcag     120
catgcgctgc tgatcttccc cggccagcac ctcagcaacg accagcagat cacttttgcc    180
aaacgcttcg gcgcgatcga gcgcatcggc ggcggcgaca tcgtggccat ctccaatgtc    240
aaggccgatg gcacggtgcg ccagcacagc cccgccgagt gggacgacat gatgaaggtc    300
atcgtcggca acatggcctg gcatgccgac agcacctaca tgccggtgat ggcgcagggc    360
gcggtgttct cggccgaagt ggtgcccgca gtgggcgggc gcacctgctt cgccgacatg    420
cgcgccgcct acgacgcgct ggacgaggcc acccgcgccc tggtgcacca gcgctcggcg    480
cggcattcgc tggtgtattc gcagagcaag ctgggccatg tgcagcaggc cggctcggcc    540
tacatcggct acggcatgga caccaccgcc acgcccctgc gcccgctggt caaggtgcat    600
cccgagaccg gccgcccctc gctgctgatc ggccgccatg cccatgccat cccgggcatg    660
gacgccgccg aatccgagcg cttcctggaa ggcctggtcg actgggcctg ccaggcgccg    720
cgggtgcatg cccaccaatg gccgccggc gacgtggtgg tgtgggacaa ccgctgcctg    780
ctgcaccgcg ccgagccctg ggatttcaag ctgccgcggg tgatgtggca cagccgcctg    840
gccggccgcc ccgagaccga gggcgccgcc ctggtgtaa                            879
```

<210> SEQ ID NO 2
<211> LENGTH: 292
<212> TYPE: PRT
<213> ORGANISM: Delftia acidovorans

<400> SEQUENCE: 2

```
Met Gln Thr Thr Leu Gln Ile Thr Pro Thr Gly Ala Thr Leu Gly Ala
1               5                   10                  15

Thr Val Thr Gly Val His Leu Ala Thr Leu Asp Asp Ala Gly Phe Ala
            20                  25                  30

Ala Leu His Ala Ala Trp Leu Gln His Ala Leu Leu Ile Phe Pro Gly
        35                  40                  45

Gln His Leu Ser Asn Asp Gln Gln Ile Thr Phe Ala Lys Arg Phe Gly
    50                  55                  60

Ala Ile Glu Arg Ile Gly Gly Gly Asp Ile Val Ala Ile Ser Asn Val
65                  70                  75                  80
```

Lys Ala Asp Gly Thr Val Arg Gln His Ser Pro Ala Glu Trp Asp
                85                  90                  95

Met Met Lys Val Ile Val Gly Asn Met Ala Trp His Ala Asp Ser Thr
            100                 105                 110

Tyr Met Pro Val Met Ala Gln Gly Ala Val Phe Ser Ala Glu Val Val
        115                 120                 125

Pro Ala Val Gly Gly Arg Thr Cys Phe Ala Asp Met Arg Ala Ala Tyr
    130                 135                 140

Asp Ala Leu Asp Glu Ala Thr Arg Ala Leu Val His Gln Arg Ser Ala
145                 150                 155                 160

Arg His Ser Leu Val Tyr Ser Gln Ser Lys Leu Gly His Val Gln Gln
                165                 170                 175

Ala Gly Ser Ala Tyr Ile Gly Tyr Gly Met Asp Thr Thr Ala Thr Pro
            180                 185                 190

Leu Arg Pro Leu Val Lys Val His Pro Glu Thr Gly Arg Pro Ser Leu
        195                 200                 205

Leu Ile Gly Arg His Ala His Ala Ile Pro Gly Met Asp Ala Ala Glu
    210                 215                 220

Ser Glu Arg Phe Leu Glu Gly Leu Val Asp Trp Ala Cys Gln Ala Pro
225                 230                 235                 240

Arg Val His Ala His Gln Trp Ala Ala Gly Asp Val Val Trp Asp
                245                 250                 255

Asn Arg Cys Leu Leu His Arg Ala Glu Pro Trp Asp Phe Lys Leu Pro
            260                 265                 270

Arg Val Met Trp His Ser Arg Leu Ala Gly Arg Pro Glu Thr Glu Gly
        275                 280                 285

Ala Ala Leu Val
    290

<210> SEQ ID NO 3
<211> LENGTH: 882
<212> TYPE: DNA
<213> ORGANISM: Delftia acidovorans

<400> SEQUENCE: 3
atggctcaga ccactctcca aatcacaccc actggtgcca ccttgggtgc cacagtcact    60
ggtgttcacc ttgccacact tgacgatgct ggtttcgctg ccctccatgc agcctggctt   120
caacatgcac tcttgatctt ccctgggcaa cacctcagca tgaccaaca gattaccttt   180 gctaaacgct ttggagcaat tgagaggatt ggcggaggtg acattgttgc catatccaat   240
gtcaaggcag atggcacagt gcgccagcac tctcctgctg agtgggatga catgatgaag   300
gtcattgtgg caacatggc ctggcacgcc gactcaacct acatgccagt catggctcaa   360
ggagctgtgt tcagcgcaga gttgtcccca gcagttgggg gcagaacctg ctttgctgac   420
atgagggcag cctacgatgc ccttgatgag caacccgtg ctcttgttca ccaaggtct   480 gctcgtcact cccttgtgta ttctcagagc aagttggac atgtccaaca ggcccgtca   540 gcctacatag gttatggcat ggacaccact gcaactcctc tcagaccatt ggtcaaggtg   600
catcctgaga ctggaaggcc cagctcttg atcggccgcc atgcccatgc catccctggc   660
atggatgcag ctgaatcaga gcgcttcctt gaaggacttg ttgactgggc ctgccaggct   720
cccagagtcc atgctcacca atgggctgct ggagatgtgg ttgtgtggga caaccgctgt   780
ttgctccacc gtgctgagcc ctgggatttc aagttgccac gtgtgatgtg gcactccaga   840
ctcgctggac gcccagaaac tgagggtgct gccttggttt ga                     882

<210> SEQ ID NO 4
<211> LENGTH: 293
<212> TYPE: PRT
<213> ORGANISM: Delftia acidovorans

<400> SEQUENCE: 4

Met Ala Gln Thr Thr Leu Gln Ile Thr Pro Thr Gly Ala Thr Leu Gly
1               5                   10                  15

Ala Thr Val Thr Gly Val His Leu Ala Thr Leu Asp Asp Ala Gly Phe
            20                  25                  30

Ala Ala Leu His Ala Ala Trp Leu Gln His Ala Leu Leu Ile Phe Pro
        35                  40                  45

Gly Gln His Leu Ser Asn Asp Gln Gln Ile Thr Phe Ala Lys Arg Phe
    50                  55                  60

Gly Ala Ile Glu Arg Ile Gly Gly Asp Ile Val Ala Ile Ser Asn
65                  70                  75                  80

Val Lys Ala Asp Gly Thr Val Arg Gln His Ser Pro Ala Glu Trp Asp
                85                  90                  95

Asp Met Met Lys Val Ile Val Gly Asn Met Ala Trp His Ala Asp Ser
            100                 105                 110

Thr Tyr Met Pro Val Met Ala Gln Gly Ala Val Phe Ser Ala Glu Val
        115                 120                 125

Val Pro Ala Val Gly Gly Arg Thr Cys Phe Ala Asp Met Arg Ala Ala
    130                 135                 140

Tyr Asp Ala Leu Asp Glu Ala Thr Arg Ala Leu Val His Gln Arg Ser
145                 150                 155                 160

Ala Arg His Ser Leu Val Tyr Ser Gln Ser Lys Leu Gly His Val Gln
                165                 170                 175

Gln Ala Gly Ser Ala Tyr Ile Gly Tyr Gly Met Asp Thr Thr Ala Thr
            180                 185                 190

Pro Leu Arg Pro Leu Val Lys Val His Pro Glu Thr Gly Arg Pro Ser
        195                 200                 205

Leu Leu Ile Gly Arg His Ala His Ala Ile Pro Gly Met Asp Ala Ala
    210                 215                 220

Glu Ser Glu Arg Phe Leu Glu Gly Leu Val Asp Trp Ala Cys Gln Ala
225                 230                 235                 240

Pro Arg Val His Ala His Gln Trp Ala Ala Gly Asp Val Val Val Trp
                245                 250                 255

Asp Asn Arg Cys Leu Leu His Arg Ala Glu Pro Trp Asp Phe Lys Leu
            260                 265                 270

Pro Arg Val Met Trp His Ser Arg Leu Ala Gly Arg Pro Glu Thr Glu
        275                 280                 285

Gly Ala Ala Leu Val
    290

<210> SEQ ID NO 5
<211> LENGTH: 882
<212> TYPE: DNA
<213> ORGANISM: Delftia acidovorans

<400> SEQUENCE: 5
atggctcaga ctaccctgca gattaccccg actggtgcga ccctgggtgc aaccgttacc      60
ggcgttcacc tggcgactct ggatgacgca ggtttcgctg cgctgcacgc ggcttggctg     120
caacatgctc tcctgatttt cccaggtcag cacctgtcca acgaccagca aatcactttt     180

```
gcaaaacgct tcggtgcgat cgaacgtatc ggtggcggtg atattgtggc gatctccaac    240
gtaaaagcgg atggtactgt acgtcagcac agcccggcgg agtgggacga tatgatgaag    300
gtgatcgtag gcaacatggc atggcatgct gacagcacct acatgccggt tatggcgcag    360
ggtgcggttt tctctgctga agtggttccg gcagtgggcg tcgcacctg cttcgcagac     420 atgcgtgcag cttacgacgc gttagacgaa gctacccgcg cactggtaca ccagcgctct    480
gcgcgtcact ctctggtgta ttcccagagc aaactgggcc acgttcagca agcgggctcc    540
gcatatatcg gctacggtat ggataccact gcgaccccgc tgcgtccgct ggtaaaagtg    600
catccggaaa ccggccgtcc gtctctcctg atcggccgtc acgctcatgc gattccgggt    660
atggacgcgg cagaatccga gcgtttcctg gaaggtctgg ttgattgggc ttgtcaggcg    720
ccgcgtgtgc atgctcacca gtgggcagct ggcgacgtgg ttgtatggga taaccgctgc    780
ctgcttcacc gtgcagaacc gtgggacttt aagctgccac gtgttatgtg gcacagccgt    840
ctggcaggcc gcccagaaac cgagggcgcg gctctggttt aa                      882

<210> SEQ ID NO 6
<211> LENGTH: 16
<212> TYPE: DNA
<213> ORGANISM: Artificial sequence
<220> FEATURE:
<223> OTHER INFORMATION: Chemically synthesized M13 forward sequencing
      primer

<400> SEQUENCE: 6
gtaaaacgac ggccag                                                    16

<210> SEQ ID NO 7
<211> LENGTH: 17
<212> TYPE: DNA
<213> ORGANISM: Artificial sequence
<220> FEATURE:
<223> OTHER INFORMATION: Chemically synthesized M13 reverse sequencing
      primer

<400> SEQUENCE: 7
caggaaacag ctatgac                                                   17

<210> SEQ ID NO 8
<211> LENGTH: 24
<212> TYPE: DNA
<213> ORGANISM: Artificial sequence
<220> FEATURE:
<223> OTHER INFORMATION: Chemically synthesized forward AAD-12 (v1) PTU
      primer

<400> SEQUENCE: 8
gaacagttag acatggtcta aagg                                           24

<210> SEQ ID NO 9
<211> LENGTH: 27
<212> TYPE: DNA
<213> ORGANISM: Artificial sequence
<220> FEATURE:
<223> OTHER INFORMATION: Chemically synthesized reverse AAD-12 (v1) PTU
      primer

<400> SEQUENCE: 9
gctgcaacac tgataaatgc caactgg                                        27

<210> SEQ ID NO 10
```

```
<211> LENGTH: 22
<212> TYPE: DNA
<213> ORGANISM: Artificial sequence
<220> FEATURE:
<223> OTHER INFORMATION: Chemically synthesized forward AAD-12 (v1)
      coding PCR primer

<400> SEQUENCE: 10
atggctcaga ccactctcca aa                                              22

<210> SEQ ID NO 11
<211> LENGTH: 20
<212> TYPE: DNA
<213> ORGANISM: Artificial sequence
<220> FEATURE:
<223> OTHER INFORMATION: Chemically synthesized reverse AAD-12 (v1)
      coding PCR primer

<400> SEQUENCE: 11
agctgcatcc atgccaggga                                                 20

<210> SEQ ID NO 12
<211> LENGTH: 22
<212> TYPE: DNA
<213> ORGANISM: Artificial sequence
<220> FEATURE:
<223> OTHER INFORMATION: Chemically synthesized SdpacodF: AAD-12 (v1)
      forward coding
      region primer

<400> SEQUENCE: 12
atggctcatg ctgccctcag cc                                              22

<210> SEQ ID NO 13
<211> LENGTH: 22
<212> TYPE: DNA
<213> ORGANISM: Artificial sequence
<220> FEATURE:
<223> OTHER INFORMATION: Chemically synthesized SdpacodR: AAD-12 (v1)
      reverse coding
      region primer

<400> SEQUENCE: 13
cgggcaggcc taactccacc aa                                              22

<210> SEQ ID NO 14
<211> LENGTH: 32
<212> TYPE: DNA
<213> ORGANISM: Artificial sequence
<220> FEATURE:
<223> OTHER INFORMATION: Chemically synthesized primer "NcoI of Brady"

<400> SEQUENCE: 14
tataccacat gtcgatcgcc atccggcagc tt                                   32

<210> SEQ ID NO 15
<211> LENGTH: 33
<212> TYPE: DNA
<213> ORGANISM: Artificial sequence
<220> FEATURE:
<223> OTHER INFORMATION: Chemically synthesized primer "SacI of Brady"

<400> SEQUENCE: 15
gagctcctat cactccgccg cctgctgctg cac                                  33

<210> SEQ ID NO 16
<211> LENGTH: 34
```

```
<212> TYPE: DNA
<213> ORGANISM: Artificial Sequence
<220> FEATURE:
<223> OTHER INFORMATION: Primer brjap 5'(speI)

<400> SEQUENCE: 16
actagtaaca aagaaggaga tataccatga cgat                              34

<210> SEQ ID NO 17
<211> LENGTH: 33
<212> TYPE: DNA
<213> ORGANISM: Artificial Sequence
<220> FEATURE:
<223> OTHER INFORMATION: Primer br jap 3' (xhoI)

<400> SEQUENCE: 17
ttctcgagct atcactccgc cgcctgctgc tgc                              33

<210> SEQ ID NO 18
<211> LENGTH: 287
<212> TYPE: PRT
<213> ORGANISM: Ralstonia eutropha JMP134

<400> SEQUENCE: 18
```

Met Ser Val Val Ala Asn Pro Leu His Pro Leu Phe Ala Ala Gly Val
1               5                   10                  15

Glu Asp Ile Asp Leu Arg Glu Ala Leu Gly Ser Thr Glu Val Arg Glu
            20                  25                  30

Ile Glu Arg Leu Met Asp Glu Lys Ser Val Leu Val Phe Arg Gly Gln
        35                  40                  45

Pro Leu Ser Gln Asp Gln Gln Ile Ala Phe Ala Arg Asn Phe Gly Pro
    50                  55                  60

Leu Glu Gly Gly Phe Ile Lys Val Asn Gln Arg Pro Ser Arg Phe Lys
65                  70                  75                  80

Tyr Ala Glu Leu Ala Asp Ile Ser Asn Val Ser Leu Asp Gly Lys Val
                85                  90                  95

Ala Gln Arg Asp Ala Arg Glu Val Val Gly Asn Phe Ala Asn Gln Leu
            100                 105                 110

Trp His Ser Asp Ser Ser Phe Gln Gln Pro Ala Ala Arg Tyr Ser Met
        115                 120                 125

Leu Ser Ala Val Val Pro Pro Ser Gly Gly Asp Thr Glu Phe Cys
    130                 135                 140

Asp Met Arg Ala Ala Tyr Asp Ala Leu Pro Arg Asp Leu Gln Ser Glu
145                 150                 155                 160

Leu Glu Gly Leu Arg Ala Glu His Tyr Ala Leu Asn Ser Arg Phe Leu
                165                 170                 175

Leu Gly Asp Thr Asp Tyr Ser Glu Ala Gln Arg Asn Ala Met Pro Pro
            180                 185                 190

Val Asn Trp Pro Leu Val Arg Thr His Ala Gly Ser Gly Arg Lys Phe
        195                 200                 205

Leu Phe Ile Gly Ala His Ala Ser His Val Glu Gly Leu Pro Val Ala
    210                 215                 220

Glu Gly Arg Met Leu Leu Ala Glu Leu Leu Glu His Ala Thr Gln Arg
225                 230                 235                 240

Glu Phe Val Tyr Arg His Arg Trp Asn Val Gly Asp Leu Val Met Trp
                245                 250                 255

Asp Asn Arg Cys Val Leu His Arg Gly Arg Arg Tyr Asp Ile Ser Ala
            260                 265                 270

```
Arg Arg Glu Leu Arg Arg Ala Thr Thr Leu Asp Asp Ala Val Val
        275                 280                 285

<210> SEQ ID NO 19
<211> LENGTH: 289
<212> TYPE: PRT
<213> ORGANISM: Bradyrhizobium japonicum USDA 110

<400> SEQUENCE: 19

Met Thr Ile Ala Ile Arg Gln Leu Gln Thr His Phe Val Gly Gln Val
1               5                   10                  15

Ser Gly Leu Asp Leu Arg Lys Pro Leu Thr Pro Gly Glu Ala Arg Glu
            20                  25                  30

Val Glu Ser Ala Met Asp Lys Tyr Ala Val Leu Val Phe His Asp Gln
        35                  40                  45

Asp Ile Thr Asp Glu Gln Gln Met Ala Phe Ala Leu Asn Phe Gly Gln
    50                  55                  60

Arg Glu Asp Ala Arg Gly Gly Thr Val Thr Lys Glu Lys Asp Tyr Arg
65                  70                  75                  80

Leu Gln Ser Gly Leu Asn Asp Val Ser Asn Leu Gly Lys Asp Gly Lys
                85                  90                  95

Pro Leu Ala Lys Asp Ser Arg Thr His Leu Phe Asn Leu Gly Asn Cys
            100                 105                 110

Leu Trp His Ser Asp Ser Ser Phe Arg Pro Ile Pro Ala Lys Phe Ser
        115                 120                 125

Leu Leu Ser Ala Arg Val Val Asn Pro Thr Gly Gly Asn Thr Glu Phe
    130                 135                 140

Ala Asp Met Arg Ala Ala Tyr Asp Ala Leu Asp Glu Thr Lys Ala
145                 150                 155                 160

Glu Ile Glu Asp Leu Val Cys Glu His Ser Leu Met Tyr Ser Arg Gly
                165                 170                 175

Ser Leu Gly Phe Thr Glu Tyr Thr Asp Glu Lys Gln Met Phe Lys
            180                 185                 190

Pro Val Leu Gln Arg Leu Val Arg Thr His Pro Val His Arg Arg Lys
        195                 200                 205

Ser Leu Tyr Leu Ser Ser His Ala Gly Lys Ile Ala Ser Met Ser Val
    210                 215                 220

Pro Glu Gly Arg Leu Leu Leu Arg Asp Leu Asn Glu His Ala Thr Gln
225                 230                 235                 240

Pro Glu Phe Val Tyr Val His Lys Trp Lys Leu His Asp Leu Val Met
                245                 250                 255

Trp Asp Asn Arg Gln Thr Met His Arg Val Arg Arg Tyr Asp Gln Ser
            260                 265                 270

Gln Pro Arg Asp Met Arg Arg Ala Thr Val Ala Gly Thr Glu Pro Thr
        275                 280                 285

Val

<210> SEQ ID NO 20
<211> LENGTH: 295
<212> TYPE: PRT
<213> ORGANISM: Sphingobium herbicidovorans

<400> SEQUENCE: 20

Met His Ala Ala Leu Ser Pro Leu Ser Gln Arg Phe Glu Arg Ile Ala
1               5                   10                  15
```

```
Val Gln Pro Leu Thr Gly Val Leu Ala Glu Ile Thr Gly Val Asp
                20                  25                  30

Leu Arg Glu Pro Leu Asp Asp Ser Thr Trp Asn Glu Ile Leu Asp Ala
     35                  40                  45

Phe His Thr Tyr Gln Val Ile Tyr Phe Pro Gly Gln Ala Ile Thr Asn
 50                  55                  60

Glu Gln His Ile Ala Phe Ser Arg Arg Phe Gly Pro Val Asp Pro Val
 65                  70                  75                  80

Pro Leu Leu Lys Ser Ile Glu Gly Tyr Pro Glu Val Gln Met Ile Arg
                 85                  90                  95

Arg Glu Ala Asn Glu Ser Gly Arg Val Ile Gly Asp Asp Trp His Thr
                100                 105                 110

Asp Ser Thr Phe Leu Asp Ala Pro Ala Ala Val Val Met Arg Ala
             115                 120                 125

Ile Asp Val Pro Glu His Gly Gly Asp Thr Gly Phe Leu Ser Met Tyr
130                 135                 140

Thr Ala Trp Glu Thr Leu Ser Pro Thr Met Gln Ala Thr Ile Glu Gly
145                 150                 155                 160

Leu Asn Val Val His Ser Ala Thr Arg Val Phe Gly Ser Leu Tyr Gln
                165                 170                 175

Ala Gln Asn Arg Arg Phe Ser Asn Thr Ser Val Lys Val Met Asp Val
                180                 185                 190

Asp Ala Gly Asp Arg Glu Thr Val His Pro Leu Val Thr His Pro
             195                 200                 205

Gly Ser Gly Arg Lys Gly Leu Tyr Val Asn Gln Val Tyr Cys Gln Arg
210                 215                 220

Ile Glu Gly Met Thr Asp Ala Glu Ser Lys Pro Leu Leu Gln Phe Leu
225                 230                 235                 240

Tyr Glu His Ala Thr Arg Phe Asp Phe Thr Cys Arg Val Arg Trp Lys
                245                 250                 255

Lys Asp Gln Val Leu Val Trp Asp Asn Leu Cys Thr Met His Arg Ala
                260                 265                 270

Val Pro Asp Tyr Ala Gly Lys Phe Arg Tyr Leu Thr Arg Thr Thr Val
                275                 280                 285

Gly Gly Val Arg Pro Ala Arg
290                 295

<210> SEQ ID NO 21
<211> LENGTH: 283
<212> TYPE: PRT
<213> ORGANISM: unknown
<220> FEATURE:
<223> OTHER INFORMATION: tauD

<400> SEQUENCE: 21

Met Ser Glu Arg Leu Ser Ile Thr Pro Leu Gly Pro Tyr Ile Gly Ala
1               5                   10                  15

Gln Ile Ser Gly Ala Asp Leu Thr Arg Pro Leu Ser Asp Asn Gln Phe
                20                  25                  30

Glu Gln Leu Tyr His Ala Val Leu Arg His Gln Val Val Phe Leu Arg
             35                  40                  45

Asp Gln Ala Ile Thr Pro Gln Gln Gln Arg Ala Leu Ala Gln Arg Phe
 50                  55                  60

Gly Glu Leu His Ile His Pro Val Tyr Pro His Ala Glu Gly Val Asp
 65                  70                  75                  80
```

-continued

```
Glu Ile Ile Val Leu Asp Thr His Asn Asp Asn Pro Pro Asp Asn Asp
            85                  90                  95

Asn Trp His Thr Asp Val Thr Phe Ile Glu Thr Pro Pro Ala Gly Ala
            100                 105                 110

Ile Leu Ala Ala Lys Glu Leu Pro Ser Thr Gly Gly Asp Thr Leu Trp
            115             120                 125

Thr Ser Gly Ile Ala Ala Tyr Glu Ala Leu Ser Val Pro Phe Arg Gln
        130             135             140

Leu Leu Ser Gly Leu Arg Ala Glu His Asp Phe Arg Lys Ser Phe Pro
145             150                 155                 160

Glu Tyr Lys Tyr Arg Lys Thr Glu Glu Glu His Gln Arg Trp Arg Glu
                165                 170                 175

Ala Val Ala Lys Asn Pro Pro Leu Leu His Pro Val Val Arg Thr His
            180                 185                 190

Pro Val Ser Gly Lys Gln Ala Leu Phe Val Asn Glu Gly Phe Thr Thr
        195                 200                 205

Arg Ile Val Asp Val Ser Glu Lys Glu Ser Glu Ala Leu Leu Ser Phe
    210                 215                 220

Leu Phe Ala His Ile Thr Lys Pro Glu Phe Gln Val Arg Trp Arg Trp
225                 230                 235                 240

Gln Pro Asn Asp Ile Ala Ile Trp Asp Asn Arg Val Thr Gln His Tyr
                245                 250                 255

Ala Asn Ala Asp Tyr Leu Pro Gln Arg Arg Ile Met His Arg Ala Thr
                260                 265                 270

Ile Leu Gly Asp Lys Pro Phe Tyr Arg Ala Gly
            275                 280
```

HERBICIDE RESISTANCE GENES

CROSS REFERENCES

This application is a continuation of U.S. patent application Ser. No. 13/647,081, filed on Oct. 8, 2012, which is a continuation of U.S. Pat. No. 8,283,522 with Ser. No. 12/091,896, filed on Nov. 3, 2008, which claims the benefit of PCT International Application Serial No. PCT/US2006/042133, filed on Oct. 27, 2006, which claims the benefit of U.S. Provisional Application Ser. No. 60/731,044, filed on Oct. 28, 2005, the disclosures each of which are expressly incorporated herein by reference.

BACKGROUND OF THE INVENTION

Weeds can quickly deplete soil of valuable nutrients needed by crops and other desirable plants. There are many different types of herbicides presently used for the control of weeds. One extremely popular herbicide is glyphosate.

Crops, such as corn, soybeans, canola, cotton, sugar beets, wheat, turf, and rice, have been developed that are resistant to glyphosate. Thus, fields with actively growing glyphosate resistant soybeans, for example, can be sprayed to control weeds without significantly damaging the soybean plants.

With the introduction of genetically engineered, glyphosate tolerant crops (GTCs) in the mid-1990's, growers were enabled with a simple, convenient, flexible, and inexpensive tool for controlling a wide spectrum of broadleaf and grass weeds unparalleled in agriculture.

Consequently, producers were quick to adopt GTCs and in many instances abandon many of the accepted best agronomic practices such as crop rotation, herbicide mode of action rotation, tank mixing, incorporation of mechanical with chemical and cultural weed control. Currently glyphosate tolerant soybean, cotton, corn, and canola are commercially available in the United States and elsewhere in the Western Hemisphere. Alfalfa was the first perennial GTC introduced, furthering the opportunity for repeated use of glyphosate on the same crop and fields repeatedly over a period of years. More GTCs (e.g., wheat, rice, sugar beets, turf, etc.) are poised for introduction pending global market acceptance. Many other glyphosate resistant species are in experimental to development stages (e.g., sugar cane, sunflower, beets, peas, carrot, cucumber, lettuce, onion, strawberry, tomato, and tobacco; forestry species like poplar and sweetgum; and horticultural species like marigold, *petunia*, and begonias; see "isb.vt.edu/cfdocs/fieldtests1.cfm, 2005" website). Additionally, the cost of glyphosate has dropped dramatically in recent years to the point that few conventional weed control programs can effectively compete on price and performance with glyphosate GTC systems.

Glyphosate has been used successfully in burndown and other non-crop areas for total vegetation control for more than 15 years. In many instances, as with GTCs, glyphosate has been used 1-3 times per year for 3, 5, 10, up to 15 years in a row. These circumstances have led to an over-reliance on glyphosate and GTC technology and have placed a heavy selection pressure on native weed species for plants that are naturally more tolerant to glyphosate or which have developed a mechanism to resist glyphosate's herbicidal activity.

Extensive use of glyphosate-only weed control programs is resulting in the selection of glyphosate-resistant weeds, and is selecting for the propagation of weed species that are inherently more tolerant to glyphosate than most target species (i.e., weed shifts). (Powles and Preston, 2006, Ng et al., 2003; Simarmata et al., 2003; Lorraine-Colwill et al., 2003; Sfiligoj, 2004; Miller et al., 2003; Heap, 2005; Murphy et al., 2002; Martin et al., 2002.) Although glyphosate has been widely used globally for more than 15 years, only a handful of weeds have been reported to have developed resistance to glyphosate (Heap, 2005); however, most of these have been identified in the past five years. Resistant weeds include both grass and broadleaf species-*Lolium rigidum, Lolium multiflorum, Eleusine indica, Sorghum halepense, Ambrosia artemisiifolia, Conyza canadensis, Conyza bonariensis, Plantago lanceolata, Amaranthus palmerii*, and *Amaranthus rudis*. Additionally, weeds that had previously not been an agronomic problem prior to the wide use of GTCs are now becoming more prevalent and difficult to control in the context of GTCs, which comprise >80% of U.S. cotton and soybean acres and >20% of U.S. corn acres (Gianessi, 2005). These weed shifts are occurring predominantly with (but not exclusively) difficult-to-control broadleaf weeds. Some examples include *Ipomoea, Amaranthus, Chenopodium, Taraxacum*, and *Commelina* species.

In areas where growers are faced with glyphosate resistant weeds or a shift to more difficult-to-control weed species, growers can compensate for glyphosate's weaknesses by tank mixing or alternating with other herbicides that will control the missed weeds. One popular and efficacious tankmix partner for controlling broadleaf escapes in many instances has been 2,4-dichlorophenoxyacetic acid (2,4-D). 2,4-D has been used agronomically and in non-crop situations for broad spectrum, broadleaf weed control for more than 60 years. Individual cases of more tolerant species have been reported, but 2,4-D remains one of the most widely used herbicides globally. A limitation to further use of 2,4-D is that its selectivity in dicot crops like soybean or cotton is very poor, and hence 2,4-D is not typically used on (and generally not near) sensitive dicot crops. Additionally, 2,4-D's use in grass crops is somewhat limited by the nature of crop injury that can occur. 2,4-D in combination with glyphosate has been used to provide a more robust burndown treatment prior to planting no-till soybeans and cotton; however, due to these dicot species' sensitivity to 2,4-D, these burndown treatments must occur at least 14-30 days prior to planting (Agriliance, 2005).

2,4-D is in the phenoxy acid class of herbicides, as is MCPA. 2,4-D has been used in many monocot crops (such as corn, wheat, and rice) for the selective control of broadleaf weeds without severely damaging the desired crop plants. 2,4-D is a synthetic auxin derivative that acts to deregulate normal cell-hormone homeostasis and impede balanced, controlled growth; however, the exact mode of action is still not known. Triclopyr and fluroxypyr are pyridyloxyacetic acid herbicides whose mode of action is as a synthetic auxin, also.

These herbicides have different levels of selectivity on certain plants (e.g., dicots are more sensitive than grasses). Differential metabolism by different plants is one explanation for varying levels of selectivity. In general, plants metabolize 2,4-D slowly, so varying plant response to 2,4-D may be more likely explained by different activity at the target site(s) (WSSA, 2002). Plant metabolism of 2,4-D typically occurs via a two-phase mechanism, typically hydroxylation followed by conjugation with amino acids or glucose (WSSA, 2002).

Over time, microbial populations have developed an alternative and efficient pathway for degradation of this particular xenobiotic, which results in the complete mineralization of 2,4-D. Successive applications of the herbicide select for microbes that can utilize the herbicide as a carbon source for growth, giving them a competitive advantage in the soil. For this reason, 2,4-D currently formulated has a relatively short soil half-life, and no significant carryover effects to subsequent crops are encountered. This adds to the herbicidal utility of 2,4-D.

One organism that has been extensively researched for its ability to degrade 2,4-D is *Ralstonia eutropha* (Streber et al., 1987). The gene that codes for the first enzymatic step in the mineralization pathway is tfdA. See U.S. Pat. No. 6,153,401 and GENBANK Acc. No. M16730. TfdA catalyzes the conversion of 2,4-D acid to dichlorophenol (DCP) via an α-ketoglutarate-dependent dioxygenase reaction (Smejkal et al., 2001). DCP has little herbicidal activity compared to 2,4-D. TfdA has been used in transgenic plants to impart 2,4-D resistance in dicot plants (e.g., cotton and tobacco) normally sensitive to 2,4-D (Streber et al. (1989), Lyon et al. (1989), Lyon (1993), and U.S. Pat. No. 5,608,147).

A large number of tfdA-type genes that encode proteins capable of degrading 2,4-D have been identified from the environment and deposited into the Genbank database. Many homologues are similar to tfdA (>85% amino acid identity) and have similar enzymatic properties to tfdA. However, there are a number of homologues that have a significantly lower identity to tfdA (25-50%), yet have the characteristic residues associated with α-ketoglutarate dioxygenase $Fe^{+2}$ dioxygenases. It is therefore not obvious what the substrate specificities of these divergent dioxygenases are.

One unique example with low homology to tfdA (31% amino acid identity) is sdpA from *Delfia acidovorans* (Kohler et al., 1999, Westendorf et al., 2002, Westendorf et al., 2003). This enzyme has been shown to catalyze the first step in (S)-dichlorprop (and other (S)-phenoxypropionic acids) as well as 2,4-D (a phenoxyacetic acid) mineralization (Westendorf et al., 2003). Transformation of this gene into plants, has not heretofore been reported.

Development of new herbicide-tolerant crop (HTC) technologies has been limited in success due largely to the efficacy, low cost, and convenience of GTCs. Consequently, a very high rate of adoption for GTCs has occurred among producers. This created little incentive for developing new HTC technologies.

Aryloxyalkanoate chemical substructures are a common entity of many commercialized herbicides including the phenoxyacetate auxins (such as 2,4-D and dichlorprop), pyridyloxyacetate auxins (such as fluroxypyr and triclopyr), aryloxyphenoxypropionates (AOPP) acetyl-coenzyme A carboxylase (ACCase) inhibitors (such as haloxyfop, quizalofop, and diclofop), and 5-substituted phenoxyacetate protoporphyrinogen oxidase IX inhibitors (such as pyraflufen and flumiclorac). However, these classes of herbicides are all quite distinct, and no evidence exists in the current literature for common degradation pathways among these chemical classes. A multifunctional enzyme for the degradation of herbicides covering multiple modes of action has recently been described (PCT US/2005/014737; filed May 2, 2005). Another unique multifunctional enzyme and potential uses are described hereafter.

BRIEF SUMMARY OF THE INVENTION

The subject invention provides novel plants that are not only resistant to 2,4-D, but also to pyridyloxyacetate herbicides. Heretofore, there was no expectation or suggestion that a plant with both of these advantageous properties could be produced by the introduction of a single gene. The subject invention also includes plants that produce one or more enzymes of the subject invention "stacked" together with one or more other herbicide resistance genes, including, but not limited to, glyphosate-, ALS- (imidazolinone, sulfonylurea), aryloxyalkanoate-, HPPD-, PPO-, and glufosinate-resistance genes, so as to provide herbicide-tolerant plants compatible with broader and more robust weed control and herbicide resistance management options. The present invention further includes methods and compositions utilizing homologues of the genes and proteins exemplified herein.

In some embodiments, the invention provides monocot and dicot plants tolerant to 2,4-D, MCPA, triclopyr, fluroxypyr, and one or more commercially available herbicides (e.g., glyphosate, glufosinate, paraquat, ALS-inhibitors (e.g., sulfonylureas, imidazolinones, triazolopyrimidine sulfonanilides, et al), HPPD inhibitors (e.g, mesotrione, isoxaflutole, et al.), dicamba, bromoxynil, aryloxyphenoxypropionates, and others). Vectors comprising nucleic acid sequences responsible for such herbicide tolerance are also disclosed, as are methods of using such tolerant plants and combinations of herbicides for weed control and prevention of weed population shifts. The subject invention enables novel combinations of herbicides to be used in new ways. Furthermore, the subject invention provides novel methods of preventing the development of, and controlling, strains of weeds that are resistant to one or more herbicides such as glyphosate. The subject invention enables novel uses of novel combinations of herbicides and crops, including pre-plant application to an area to be planted immediately prior to planting with seed for plants that would otherwise be sensitive to that herbicide (such as 2,4-D).

The subject invention relates in part to the identification of an enzyme that is not only able to degrade 2,4-D, but also surprisingly possesses novel properties, which distinguish the enzyme of the subject invention from previously known tfdA proteins, for example. More specifically, the subject invention relates to the use of an enzyme that is capable of degrading both 2,4-D and pyridyloxyacetate herbicides. No α-ketoglutarate-dependent dioxygenase enzyme has previously been reported to have the ability to degrade herbicides of both the phenoxyacetate and pyridyloxyacetates auxin herbicides. The preferred enzyme and gene for use according to the subject invention are referred to herein as AAD-12 (AryloxyAlkanoate Dioxygenase). This highly novel discovery is the basis of significant herbicide-tolerant crop (HTC) trait and selectable marker opportunities. Plants of the subject invention can be resistant throughout their entire life cycle.

There was no prior motivation to produce plants comprising an AAD-12 gene (preferably an AAD-12 polynucleotide that has a sequence optimized for expression in one or more types of plants, as exemplified herein), and there was no expectation that such plants could effectively produce an AAD-12 enzyme to render the plants resistant a phenoxyacetic acid herbicide (such as 2,4-D) and/or one or more pyridyloxyacetates herbicides such as triclopyr and fluroxypyr. Thus, the subject invention provides many advantages that were not heretofore thought to be possible in the art.

This invention also relates in part to the identification and use of genes encoding aryloxyalkanoate dioxygenase enzymes that are capable of degrading phenoxyacetate auxin and/or pyridyloxyacetates auxin herbicides. Methods of screening proteins for these activities are within the scope of the subject invention. Thus, the subject invention includes degradation of 2,4-dichlorophenoxyacetic acid and other aryloxyalkanoate auxin herbicides by a recombinantly expressed AAD-12 enzyme. The subject invention also includes methods of controlling weeds wherein said methods comprise applying one or more pyridyloxyacetate or phenoxyacetate auxin herbicides to plants comprising an AAD-12 gene. The subject invention also provides methods of using an AAD-12 gene as a selectable marker for identifying plant cells and whole plants transformed with AAD-12, optionally including one, two, or more exogenous genes simultaneously inserted into target plant cells. Methods of the subject invention include selecting transformed cells that are resistant to appropriate levels of an herbicide. The subject invention further includes methods of preparing a polypeptide, having the biological activity of aryloxyalkanoate dioxygenase, by culturing plants and/or cells of the subject invention.

BRIEF DESCRIPTION OF THE FIGURES

FIG. 2 is an amino acid sequence alignment of an exemplified AAD-12 protein (SEQ ID NO:2), TfdA (SEQ ID NO:18), AAD-2 (SEQ ID NO:19), AAD-1 (SEQ ID NO 20), and TauD (SEQ ID NO:21).

BRIEF DESCRIPTION OF THE SEQUENCES

SEQ ID NO:1 is the nucleotide sequence of AAD-12 from *Delftia acidovorans*.

SEQ ID NO:2 is the translated protein sequence encoded by SEQ ID NO: 1.

SEQ ID NO:3 is the plant optimized nucleotide sequence of AAD-12 (v1).

SEQ ID NO:4 is the translated protein sequence encoded by SEQ ID NO:3.

SEQ ID NO:5 is the *E. coli* optimized nucleotide sequence of AAD-12 (v2).

SEQ ID NO:6 is the sequence of the M13 forward primer.

SEQ ID NO:7 is the sequence of the M13 reverse primer.

SEQ ID NO:8 is the sequence of the forward AAD-12 (v1) PTU primer.

SEQ ID NO:9 is the sequence of the reverse AAD-12 (v1) PTU primer.

SEQ ID NO:10 is the sequence of the forward AAD-12 (v1) coding PCR primer.

SEQ ID NO:11 is the sequence of the reverse AAD-12 (v1) coding PCR primer.

SEQ ID NO:12 shows the sequence of the "sdpacodF" AAD-12 (v1) primer.

SEQ ID NO:13 shows the sequence of the "sdpacodR" AAD-12 (v1) primer.

SEQ ID NO:14 shows the sequence of the "Nco1 of Brady" primer.

SEQ ID NO:15 shows the sequence of the "Sac1 of Brady" primer.

SEQ ID NO:16 provides the sequence of forward primer brjap 5' (speI).

SEQ ID NO:17 provides the sequence of reverse primer brjap 3' (xhoI).

SEQ ID NO:18 provides the sequence of tfdA.

SEQ ID NO:19 provides the sequence of AAD-2.

SEQ ID NO:20 provides the sequence of AAD-1.

SEQ ID NO:21 provides the sequence of tauD.

DETAILED DESCRIPTION OF THE INVENTION

Figure 1:
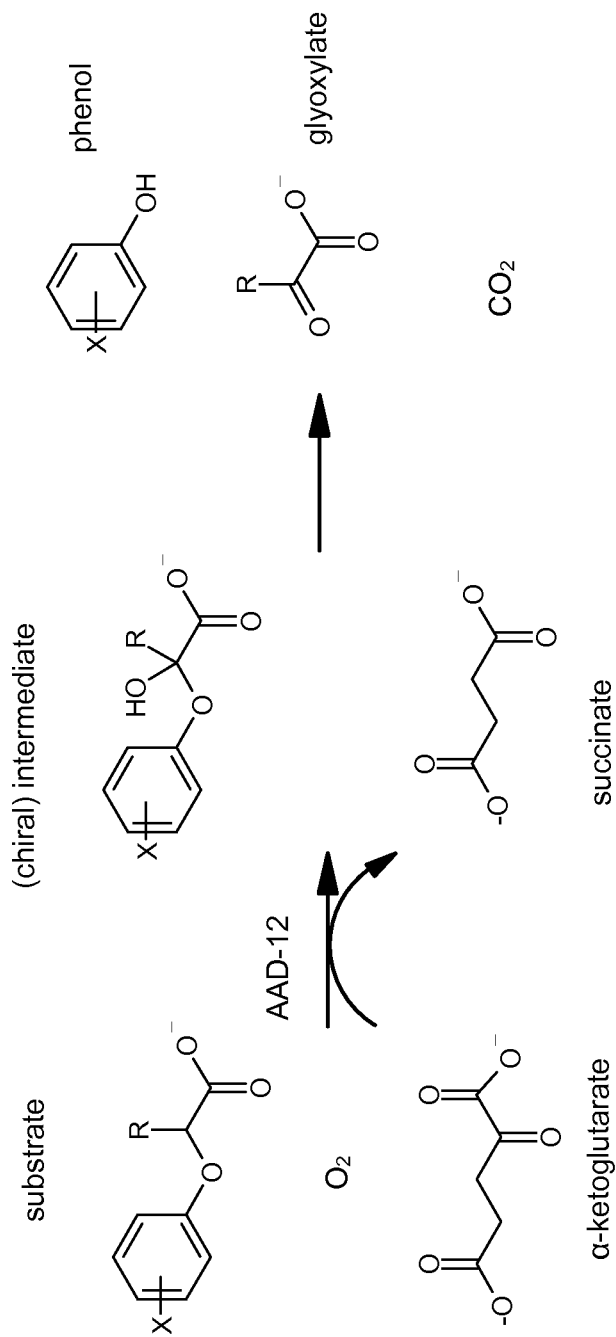
FIG. 1 illustrates the general chemical reaction that is catalyzed by AAD-12 enzymes of the subject invention.

The subject development of a 2,4-D resistance gene and subsequent resistant crops provides excellent options for controlling broadleaf, glyphosate-resistant (or highly tolerant and shifted) weed species for in-crop applications. 2,4-D is a broad-spectrum, relatively inexpensive, and robust broadleaf herbicide that would provide excellent utility for growers if greater crop tolerance could be provided in dicot and monocot crops alike. 2,4-D-tolerant transgenic dicot crops would also have greater flexibility in the timing and rate of application. An additional utility of the subject herbicide tolerance trait for 2,4-D is its utility to prevent damage to normally sensitive crops from 2,4-D drift, volatilization, inversion (or other off-site movement phenomenon), misapplication, vandalism, and the like. An additional benefit of the AAD-12 gene is that unlike all tfdA homologues characterized to date, AAD-12 is able to degrade the pyridyloxyacetates auxins (e.g., triclopyr, fluroxypyr) in addition to achiral phenoxy auxins (e.g., 2,4-D, MCPA, 4-chlorophenoxyacetic acid). See Table 1. A general illustration of the chemical reactions catalyzed by the subject AAD-12 enzyme is shown in FIG. 1. (Addition of $O_2$ is stereospecific; breakdown of intermediate to phenol and glyoxylate is spontaneous.) It should be understood that the chemical structures in FIG. 1 illustrate the molecular backbones and that various R groups and the like (such as those shown in Table 1) are included but are not necessarily specifically illustrated in FIG. 1. Multiple mixes of different phenoxy auxin combinations have been used globally to address specific weed spectra and environmental conditions in various regions. Use of the AAD-12 gene in plants affords protection to a much wider spectrum of auxin herbicides, thereby increasing the flexibility and spectra of weeds that can be controlled. The subject invention can also be used to protect from drift or other off-site synthetic auxin herbicide injury for the full breadth of commercially available phenoxy auxins. Table 1 defines commercially available pyridyloxy and phenoxy auxins and provides relevant chemical structures.

TABLE 1

Commercially available phenoxyacetate and pyridyloxyacetate auxins. Reference to phenoxy auxin and pyridyloxy auxin herbicides is generally made to the active acid but some are commercially formulated as any of a variety of corresponding ester formulations and these are likewise considered as substrates for AAD-12 enzyme in planta as general plant esterases convert these esters to the active acids in planta. Likewise reference can also be for the corresponding organic or inorganic salt of the corresponding acid. Possible use rate ranges can be as stand-alone treatments or in combination with other herbicides in both crop and non-crop uses.

| Chemical name | CAS no | Possible use rate ranges (g ae/ha) | Preferred use rate ranges (g ae/ha) | Structure |
|---|---|---|---|---|
| 2,4-D | 94-75-7 | 25-4000 | 280-1120 | 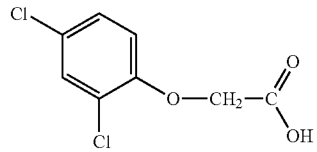 [SMILES: O=C(O)COc1ccc(Cl)cc1Cl] |
| 2,4,5-T | 93-76-5 | 25-4000 | 25-4000 | 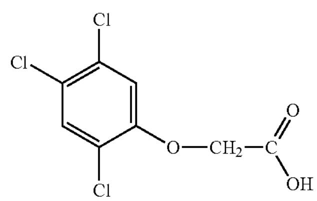 [SMILES: O=C(O)COc1cc(Cl)c(Cl)cc1Cl] |
| 4-CPA | 122-88-3 | 25-4000 | 25-4000 | 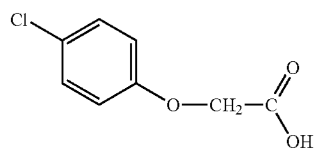 [SMILES: O=C(O)COc1ccc(Cl)cc1] |
| 3,4-DA | 588-22-7 | 25-4000 | 25-4000 | 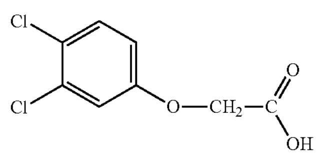 [SMILES: O=C(O)COc1ccc(Cl)c(Cl)c1] |
| MCPA | 94-74-6 | 25-4000 | 125-1550 | 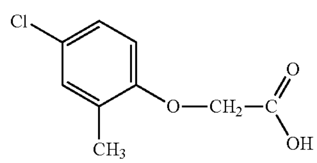 |
| Triclopyr | 55335-06-3 | 50-2000 | 70-840 | 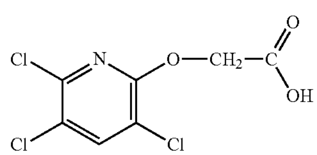 [SMILES: O=C(O)COc1nc(Cl)c(Cl)cc1Cl] |
| Fluroxypyr | 69377-81-7 | 25-2000 | 35-560 | 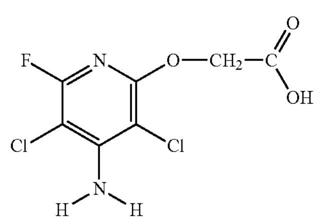 [SMILES: Nc1c(Cl)c(F)nc(OCC(=O)O)c1Cl] |

A single gene (AAD-12) has now been identified which, when genetically engineered for expression in plants, has the properties to allow the use of phenoxy auxin herbicides in plants where inherent tolerance never existed or was not sufficiently high to allow use of these herbicides. Additionally, AAD-12 can provide protection in planta to pyridyloxyacetate herbicides where natural tolerance also was not sufficient to allow selectivity, expanding the potential utility of these herbicides. Plants containing AAD-12 alone now may be treated sequentially or tank mixed with one, two, or a combination of several phenoxy auxin herbicides. The rate for each phenoxy auxin herbicide may range from 25 to 4000 g ae/ha, and more typically from 100 to 2000 g ae/ha for the control of a broad spectrum of dicot weeds. Likewise, one, two, or a mixture of several pyridyloxyacetate auxin compounds may be applied to plants expressing AAD-12 with reduced risk of injury from said herbicides. The rate for each pyridyloxyacetate herbicide may range from 25 to 2000 g ae/ha, and more typically from 35-840 g ae/ha for the control of additional dicot weeds.

Glyphosate is used extensively because it controls a very wide spectrum of broadleaf and grass weed species. However, repeated use of glyphosate in GTCs and in non-crop applications has, and will continue to, select for weed shifts to naturally more tolerant species or glyphosate-resistant biotypes. Tankmix herbicide partners used at efficacious rates that offer control of the same species but having different modes of action is prescribed by most herbicide resistance management strategies as a method to delay the appearance of resistant weeds. Stacking AAD-12 with a glyphosate tolerance trait (and/or with other herbicide-tolerance traits) could provide a mechanism to allow for the control of glyphosate resistant dicot weed species in GTCs by enabling the use of glyphosate, phenoxy auxin(s) (e.g., 2,4-D) and pyridyloxyacetates auxin herbicides (e.g., triclopyr)-selectively in the same crop. Applications of these herbicides could be simultaneously in a tank mixture comprising two or more herbicides of different modes of action; individual applications of single herbicide composition in sequential applications as pre-plant, preemergence, or postemergence and split timing of applications ranging from approximately 2 hours to approximately 3 months; or, alternatively, any combination of any number of herbicides representing each chemical class can be applied at any timing within about 7 months of planting the crop up to harvest of the crop (or the preharvest interval for the individual herbicide, whichever is shortest).

It is important to have flexibility in controlling a broad spectrum of grass and broadleaf weeds in terms of timing of application, rate of individual herbicides, and the ability to control difficult or resistant weeds. Glyphosate applications in a crop with a glyphosate resistance gene/AAD-12 stack could range from about 250-2500 g ae/ha; phenoxy auxin herbicide(s) (one or more) could be applied from about 25-4000 g ae/ha; and pyridyloxyacetates auxin herbicide(s) (one or more) could be applied from 25-2000 g ae/ha. The optimal combination(s) and timing of these application(s) will depend on the particular situation, species, and environment, and will be best determined by a person skilled in the art of weed control and having the benefit of the subject disclosure.

Plantlets are typically resistant throughout the entire growing cycle. Transformed plants will typically be resistant to new herbicide application at any time the gene is expressed. Tolerance is shown herein to 2,4-D across the life cycle using the constitutive promoters tested thus far (primarily CsVMV and AtUbi 10). One would typically expect this, but it is an improvement upon other non-metabolic activities where tolerance can be significantly impacted by the reduced expression of a site of action mechanism of resistance, for example. One example is Roundup Ready cotton, where the plants were tolerant if sprayed early, but if sprayed too late the glyphosate concentrated in the meristems (because it is not metabolized and is translocated); viral promoters Monsanto used are not well expressed in the flowers. The subject invention provides an improvement in these regards.

Herbicide formulations (e.g., ester, acid, or salt formulation; or soluble concentrate, emulsifiable concentrate, or soluble liquid) and tankmix additives (e.g., adjuvants, surfactants, drift retardants, or compatibility agents) can significantly affect weed control from a given herbicide or combination of one or more herbicides. Any combination of these with any of the aforementioned herbicide chemistries is within the scope of this invention.

One skilled in the art would also see the benefit of combining two or more modes of action for increasing the spectrum of weeds controlled and/or for the control of naturally more tolerant or resistant weed species. This could also extend to chemistries for which herbicide tolerance was enabled in crops through human involvement (either transgenically or non-transgenically) beyond GTCs. Indeed, traits encoding glyphosate resistance (e.g., resistant plant or bacterial EPSPS, glyphosate oxidoreductase (GOX), GAT), glufosinate resistance (e.g., Pat, bar), acetolactate synthase (ALS)-inhibiting herbicide resistance (e.g., imidazolinone, sulfonylurea, triazolopyrimidine sulfonanilide, pyrmidinylthiobenzoates, and other chemistries=AHAS, Csrl, SurA, et al.), bromoxynil resistance (e.g., Bxn), resistance to inhibitors of HPPD (4-hydroxlphenyl-pyruvate-dioxygenase) enzyme, resistance to inhibitors of phytoene desaturase (PDS), resistance to photosystem II inhibiting herbicides (e.g., psbA), resistance to photosystem I inhibiting herbicides, resistance to protoporphyrinogen oxidase IX (PPO)-inhibiting herbicides (e.g., PPO-1), resistance to phenylurea herbicides (e.g., CYP76B1), dicamba-degrading enzymes (see, e.g., US 20030135879), and others could be stacked alone or in multiple combinations to provide the ability to effectively control or prevent weed shifts and/or resistance to any herbicide of the aforementioned classes. In vivo modified EPSPS can be used in some preferred embodiments, as well as Class I, Class II, and Class III glyphosate resistance genes.

Regarding additional herbicides, some additional preferred ALS inhibitors include but are not limited to the sulfonylureas (such as chlorsulfuron, halosulfuron, nicosulfuron, sulfometuron, sulfosulfuron, trifloxysulfuron), imidazoloninones (such as imazamox, imazethapyr, imazaquin), triazolopyrimidine sulfonanilides (such as cloransulam-methyl, diclosulam, florasulam, flumetsulam, metosulam, and penoxsulam), pyrimidinylthiobenzoates (such as bispyribac and pyrithiobac), and flucarbazone. Some preferred HPPD inhibitors include but are not limited to mesotrione, isoxaflutole, and sulcotrione. Some preferred PPO inhibitors include but are not limited to flumiclorac, flumioxazin, flufenpyr, pyraflufen, fluthiacet, butafenacil, carfentrazone, sulfentrazone, and the diphenylethers (such as acifluorfen, fomesafen, lactofen, and oxyfluorfen).

Additionally, AAD-12 alone or stacked with one or more additional HTC traits can be stacked with one or more additional input (e.g., insect resistance, fungal resistance, or stress tolerance, et al.) or output (e.g., increased yield, improved oil profile, improved fiber quality, et al.) traits. Thus, the subject invention can be used to provide a complete agronomic package of improved crop quality with the ability to flexibly and cost effectively control any number of agronomic pests.

The subject invention relates in part to the identification of an enzyme that is not only able to degrade 2,4-D, but also surprisingly possesses novel properties, which distinguish the enzyme of the subject invention from previously known tfdA proteins, for example. Even though this enzyme has very low homology to tfdA, the genes of the subject invention can still be generally classified in the same overall family of α-ketoglutarate-dependent dioxygenases. This family of proteins is characterized by three conserved histidine residues in a "HX(D/E)X$_{23-26}$(T/S)X$_{114-183}$HX$_{10-13}$R" motif which comprises the active site. The histidines coordinate Fe$^{+2}$ ion in the active site that is essential for catalytic activity (Hogan et al., 2000). The preliminary in vitro expression experiments discussed herein were tailored to help select for novel attributes. These experiments also indicate the AAD-12 enzyme is unique from another disparate enzyme of the same class, disclosed in a previously filed patent application (PCT US/2005/014737; filed May 2, 2005). The AAD-1 enzyme of that application shares only about 25% sequence identity with the subject AAD-12 protein.

More specifically, the subject invention relates in part to the use of an enzyme that is not only capable of degrading 2,4-D, but also pyridyloxyacetate herbicides. No α-ketoglutarate-dependent dioxygenase enzyme has previously been reported to have the ability to degrade herbicides of different chemical classes and modes of action. Preferred enzymes and genes for use according to the subject invention are referred to herein as AAD-12 (AryloxyAlkanoate Dioxygenase) genes and proteins.

This invention also relates in part to the identification and use of genes encoding aryloxyalkanoate dioxygenase enzymes that are capable of degrading phenoxy auxin and pyridyloxyacetate herbicides. Thus, the subject invention relates in part to the degradation of 2,4-dichlorophenoxyacetic acid, other phenoxyacetic acids, and pyridyloxyacetic acid herbicides by a recombinantly expressed AAD-12 enzyme.

The subject proteins tested positive for 2,4-D conversion to 2,4-dichlorophenol ("DCP"; herbicidally inactive) in analytical assays. Partially purified proteins of the subject invention can rapidly convert 2,4-D to DCP in vitro. An additional advantage that AAD-12 transformed plants provide is that parent herbicide(s) are metabolized to inactive forms, thereby reducing the potential for harvesting herbicidal residues in grain or stover.

The subject invention also includes methods of controlling weeds wherein said methods comprise applying a pyridyloxyacetate and/or a phenoxy auxin herbicide to plants comprising an AAD-12 gene.

In light of these discoveries, novel plants that comprise a polynucleotide encoding this type of enzyme are now provided. Heretofore, there was no motivation to produce such plants, and there was no expectation that such plants could effectively produce this enzyme to render the plants resistant to not only phenoxy acid herbicides (such as 2,4-D) but also pyridyloxyacetate herbicides. Thus, the subject invention provides many advantages that were not heretofore thought to be possible in the art.

Publicly available strains (deposited in culture collections like ATCC or DSMZ) can be acquired and screened, using techniques disclosed herein, for novel genes. Sequences disclosed herein can be used to amplify and clone the homologous genes into a recombinant expression system for further screening and testing according to the subject invention.

As discussed above in the Background section, one organism that has been extensively researched for its ability to degrade 2,4-D is *Ralstonia eutropha* (Streber et al., 1987). The gene that codes for the first enzyme in the degradation pathway is tfdA. See U.S. Pat. No. 6,153,401 and GENBANK Acc. No. M16730. TfdA catalyzes the conversion of 2,4-D acid to herbicidally inactive DCP via an α-ketoglutarate-dependent dioxygenase reaction (Smejkal et al., 2001). TfdA has been used in transgenic plants to impart 2,4-D resistance in dicot plants (e.g., cotton and tobacco) normally sensitive to 2,4-D (Streber et al., 1989; Lyon et al., 1989; Lyon et al., 1993). A large number of tfdA-type genes that encode proteins capable of degrading 2,4-D have been identified from the environment and deposited into the Genbank database. Many homologues are quite similar to tfdA (>85% amino acid identity) and have similar enzymatic properties to tfdA. However, a small collection of α-ketoglutarate-dependent dioxygenase homologues are presently identified that have a low level of homology to tfdA.

The subject invention relates in part to surprising discoveries of new uses for and functions of a distantly related enzyme, sdpA, from *Delfia acidivorans* (Westendorf et al., 2002, 2003) with low homology to tfdA (31% amino acid identity). This α-ketoglutarate-dependent dioxygenase enzyme purified in its native form had previously been shown to degrade 2,4-D and S-dichlorprop (Westendorf et al., 2002 and 2003). However, no α-ketoglutarate-dependent dioxygenase enzyme has previously been reported to have the ability to degrade herbicides of pyridyloxyacetate chemical class. SdpA has never been expressed in plants, nor was there any motivation to do so in part because development of new HTC technologies has been limited due largely to the efficacy, low cost, and convenience of GTCs (Devine, 2005).

In light of the novel activity, proteins and genes of the subject invention are referred to herein as AAD-12 proteins and genes. AAD-12 was presently confirmed to degrade a variety of phenoxyacetate auxin herbicides in vitro. However, this enzyme, as reported for the first time herein, was surprisingly found to also be capable of degrading additional substrates of the class of aryloxyalkanoate molecules. Substrates of significant agronomic importance include the pyridyloxyacetate auxin herbicides. This highly novel discovery is the basis of significant Herbicide Tolerant Crop (HTC) and selectable marker trait opportunities. This enzyme is unique in its ability to deliver herbicide degradative activity to a range of broad spectrum broadleaf herbicides (phenoxyacetate and pyridyloxyacetate auxins).

Thus, the subject invention relates in part to the degradation of 2,4-dichlorophenoxyacetic acid, other phenoxyacetic auxin herbicides, and pyridyloxyacetate herbicides by a recombinantly expressed aryloxyalkanoate dioxygenase enzyme (AAD-12). This invention also relates in part to identification and uses of genes encoding an aryloxyalkanoate dioxygenase degrading enzyme (AAD-12) capable of degrading phenoxy and/or pyridyloxy auxin herbicides.

The subject enzyme enables transgenic expression resulting in tolerance to combinations of herbicides that would control nearly all broadleaf weeds. AAD-12 can serve as an excellent herbicide tolerant crop (HTC) trait to stack with other HTC traits [e.g., glyphosate resistance, glufosinate resistance, ALS-inhibitor (e.g., imidazolinone, sulfonylurea, triazolopyrimidine sulfonanilide) resistance, bromoxynil resistance, HPPD-inhibitor resistance, PPO-inhibitor resistance, et al.], and insect resistance traits (Cry1F, Cry1Ab, Cry 34/45, other Bt. Proteins, or insecticidal proteins of a non-*Bacillus* origin, et al.) for example. Additionally, AAD-12 can serve as a selectable marker to aid in selection of primary transformants of plants genetically engineered with a second gene or group of genes.

In addition, the subject microbial gene has been redesigned such that the protein is encoded by codons having a bias toward both monocot and dicot plant usage (hemicot). *Arabidopsis*, corn, tobacco, cotton, soybean, canola, and rice have been transformed with AAD-12-containing constructs and have demonstrated high levels of resistance to both the phenoxy and pyridyloxy auxin herbicides. Thus, the subject invention also relates to "plant optimized" genes that encode proteins of the subject invention.

Oxyalkanoate groups are useful for introducing a stable acid functionality into herbicides. The acidic group can impart phloem mobility by "acid trapping," a desirable attribute for herbicide action and therefore could be incorporated into new herbicides for mobility purposes. Aspects of the subject invention also provide a mechanism of creating HTCs. There exist many potential commercial and experimental herbicides that can serve as substrates for AAD-12. Thus, the use of the subject genes can also result in herbicide tolerance to those other herbicides as well.

HTC traits of the subject invention can be used in novel combinations with other HTC traits (including but not limited to glyphosate tolerance). These combinations of traits give rise to novel methods of controlling weed (and like) species, due to the newly acquired resistance or inherent tolerance to herbicides (e.g., glyphosate). Thus, in addition to the HTC traits, novel methods for controlling weeds using herbicides, for which herbicide tolerance was created by said enzyme in transgenic crops, are within the scope of the invention.

This invention can be applied in the context of commercializing a 2,4-D resistance trait stacked with current glyphosate resistance traits in soybeans, for example. Thus, this invention provides a tool to combat broadleaf weed species shifts and/or selection of herbicide resistant broadleaf weeds, which culminates from extremely high reliance by growers on glyphosate for weed control with various crops.

The transgenic expression of the subject AAD-12 genes is exemplified in, for example, *Arabidopsis*, tobacco, soybean, cotton, rice, corn and canola. Soybeans are a preferred crop for transformation according to the subject invention. However, this invention can be utilized in multiple other monocot (such as pasture grasses or turf grass) and dicot crops like alfalfa, clover, tree species, et al. Likewise, 2,4-D (or other AAD-12-substrates) can be more positively utilized in grass crops where tolerance is moderate, and increased tolerance via this trait would provide growers the opportunity to use these herbicides at more efficacious rates and over a wider application timing without the risk of crop injury.

Still further, the subject invention provides a single gene that can provide resistance to herbicides that control broadleaf weed. This gene may be utilized in multiple crops to enable the use of a broad spectrum herbicide combination. The subject invention can also control weeds resistant to current chemicals, and aids in the control of shifting weed spectra resulting from current agronomic practices. The subject AAD-12 can also be used in efforts to effectively detoxify additional herbicide substrates to non-herbicidal forms. Thus, the subject invention provides for the development of additional HTC traits and/or selectable marker technology.

Separate from, or in addition to, using the subject genes to produce HTCs, the subject genes can also be used as selectable markers for successfully selecting transformants in cell cultures, greenhouses, and in the field. There is high inherent value for the subject genes simply as a selectable marker for biotechnology projects. The promiscuity of AAD-12 for other aryloxyalkanoate auxinic herbicides provides many opportunities to utilize this gene for HTC and/or selectable marker purposes.

Proteins (and Source Isolates) of the Subject Invention.

The present invention provides functional proteins. By "functional activity" (or "active") it is meant herein that the proteins/enzymes for use according to the subject invention have the ability to degrade or diminish the activity of a herbicide (alone or in combination with other proteins). Plants producing proteins of the subject invention will preferably produce "an effective amount" of the protein so that when the plant is treated with a herbicide, the level of protein expression is sufficient to render the plant completely or partially resistant or tolerant to the herbicide (at a typical rate, unless otherwise specified; typical application rates can be found in the well-known *Herbicide Handbook* (Weed Science Society of America, Eighth Edition, 2002), for example). The herbicide can be applied at rates that would normally kill the target plant, at normal field use rates and concentrations. (Because of the subject invention, the level and/or concentration can optionally be higher than those that were previously used.) Preferably, plant cells and plants of the subject invention are protected against growth inhibition or injury caused by herbicide treatment. Transformed plants and plant cells of the subject invention are preferably rendered resistant or tolerant to an herbicide, as discussed herein, meaning that the transformed plant and plant cells can grow in the presence of effective amounts of one or more herbicides as discussed herein. Preferred proteins of the subject invention have catalytic activity to metabolize one or more aryloxyalkanoate compounds.

One cannot easily discuss the term "resistance" and not use the verb "tolerate" or the adjective "tolerant." The industry has spent innumerable hours debating Herbicide Tolerant Crops (HTC) versus Herbicide Resistant Crops (HRC). HTC is a preferred term in the industry. However, the official Weed Science Society of America definition of resistance is "the inherited ability of a plant to survive and reproduce following exposure to a dose of herbicide normally lethal to the wild type. In a plant, resistance may be naturally occurring or induced by such techniques as genetic engineering or selection of variants produced by tissue culture or mutagenesis." As used herein unless otherwise indicated, herbicide "resistance" is heritable and allows a plant to grow and reproduce in the presence of a typical herbicidally effective treatment by a herbicide for a given plant, as suggested by the current edition of *The Herbicide Handbook* as of the filing of the subject disclosure. As is recognized by those skilled in the art, a plant may still be considered "resistant" even though some degree of plant injury from herbicidal exposure is apparent. As used herein, the term "tolerance" is broader than the term "resistance," and includes "resistance" as defined herein, as well an improved capacity of a particular plant to withstand the various degrees of herbicidally induced injury that typically result in wild-type plants of the same genotype at the same herbicidal dose.

Transfer of the functional activity to plant or bacterial systems can involve a nucleic acid sequence, encoding the amino acid sequence for a protein of the subject invention, integrated into a protein expression vector appropriate to the host in which the vector will reside. One way to obtain a nucleic acid sequence encoding a protein with functional activity is to isolate the native genetic material from the bacterial species which produce the protein of interest, using information deduced from the protein's amino acid sequence, as disclosed herein. The native sequences can be optimized for expression in plants, for example, as discussed in more detail below. An optimized polynucleotide can also be designed based on the protein sequence.

The subject invention provides classes of proteins having novel activities as identified herein. One way to characterize these classes of proteins and the polynucleotides that encode them is by defining a polynucleotide by its ability to hybridize, under a range of specified conditions, with an exemplified nucleotide sequence (the complement thereof and/or a probe or probes derived from either strand) and/or by their ability to be amplified by PCR using primers derived from the exemplified sequences.

There are a number of methods for obtaining proteins for use according to the subject invention. For example, antibodies to the proteins disclosed herein can be used to identify and isolate other proteins from a mixture of proteins. Specifically, antibodies may be raised to the portions of the proteins that are most conserved or most distinct, as compared to other related proteins. These antibodies can then be used to specifically identify equivalent proteins with the characteristic activity by immunoprecipitation, enzyme linked immunosorbent assay (ELISA), or immuno-blotting. Antibodies to the proteins disclosed herein, or to equivalent proteins, or to fragments of these proteins, can be readily prepared using standard procedures. Such antibodies are an aspect of the subject invention. Antibodies of the subject invention include monoclonal and polyclonal antibodies, preferably produced in response to an exemplified or suggested protein.

One skilled in the art would readily recognize that proteins (and genes) of the subject invention can be obtained from a variety of sources. Since entire herbicide degradation operons are known to be encoded on transposable elements such as plasmids, as well as genomically integrated, proteins of the subject invention can be obtained from a wide variety of microorganisms, for example, including recombinant and/or wild-type bacteria.

Mutants of bacterial isolates can be made by procedures that are well known in the art. For example, asporogenous mutants can be obtained through ethylmethane sulfonate (EMS) mutagenesis of an isolate. The mutant strains can also be made using ultraviolet light and nitrosoguanidine by procedures well known in the art.

A protein "from" or "obtainable from" any of the subject isolates referred to or suggested herein means that the protein (or a similar protein) can be obtained from the isolate or some other source, such as another bacterial strain or a plant. "Derived from" also has this connotation, and includes proteins obtainable from a given type of bacterium that are modified for expression in a plant, for example. One skilled in the art will readily recognize that, given the disclosure of a bacterial gene and protein, a plant can be engineered to produce the protein. Antibody preparations, nucleic acid probes (DNA, RNA, or PNA, for example), and the like can be prepared using the polynucleotide and/or amino acid sequences disclosed herein and used to screen and recover other related genes from other (natural) sources.

Standard molecular biology techniques may be used to clone and sequence the proteins and genes described herein. Additional information may be found in Sambrook et al., 1989, which is incorporated herein by reference.

Polynucleotides and Probes.

The subject invention further provides nucleic acid sequences that encode proteins for use according to the subject invention. The subject invention further provides methods of identifying and characterizing genes that encode proteins having the desired herbicidal activity. In one embodiment, the subject invention provides unique nucleotide sequences that are useful as hybridization probes and/or primers for PCR techniques. The primers produce characteristic gene fragments that can be used in the identification, characterization, and/or isolation of specific genes of interest. The nucleotide sequences of the subject invention encode proteins that are distinct from previously described proteins.

The polynucleotides of the subject invention can be used to form complete "genes" to encode proteins or peptides in a desired host cell. For example, as the skilled artisan would readily recognize, the subject polynucleotides can be appropriately placed under the control of a promoter in a host of interest, as is readily known in the art. The level of gene expression and temporal/tissue specific expression can greatly impact the utility of the invention. Generally, greater levels of protein expression of a degradative gene will result in faster and more complete degradation of a substrate (in this case a target herbicide). Promoters will be desired to express the target gene at high levels unless the high expression has a consequential negative impact on the health of the plant. Typically, one would wish to have the AAD-12 gene constitutively expressed in all tissues for complete protection of the plant at all growth stages. However, one could alternatively use a vegetatively expressed resistance gene; this would allow use of the target herbicide in-crop for weed control and would subsequently control sexual reproduction of the target crop by application during the flowering stage. In addition, desired levels and times of expression can also depend on the type of plant and the level of tolerance desired. Some preferred embodiments use strong constitutive promoters combined with transcription enhancers and the like to increase expression levels and to enhance tolerance to desired levels. Some such applications are discussed in more detail below, before the Examples section.

As the skilled artisan knows, DNA typically exists in a double-stranded form. In this arrangement, one strand is complementary to the other strand and vice versa. As DNA is replicated in a plant (for example), additional complementary strands of DNA are produced. The "coding strand" is often used in the art to refer to the strand that binds with the anti-sense strand. The mRNA is transcribed from the "anti-sense" strand of DNA. The "sense" or "coding" strand has a series of codons (a codon is three nucleotides that can be read as a three-residue unit to specify a particular amino acid) that can be read as an open reading frame (ORF) to form a protein or peptide of interest. In order to produce a protein in vivo, a strand of DNA is typically transcribed into a complementary strand of mRNA which is used as the template for the protein. Thus, the subject invention includes the use of the exemplified polynucleotides shown in the attached sequence listing and/or equivalents including the complementary strands. RNA and PNA (peptide nucleic acids) that are functionally equivalent to the exemplified DNA molecules are included in the subject invention.

In one embodiment of the subject invention, bacterial isolates can be cultivated under conditions resulting in high multiplication of the microbe. After treating the microbe to provide single-stranded genomic nucleic acid, the DNA can be contacted with the primers of the invention and subjected to PCR amplification. Characteristic fragments of genes of interest will be amplified by the procedure, thus identifying the presence of the gene(s) of interest.

Further aspects of the subject invention include genes and isolates identified using the methods and nucleotide sequences disclosed herein. The genes thus identified can encode herbicidal resistance proteins of the subject invention.

Proteins and genes for use according to the subject invention can be identified and obtained by using oligonucleotide probes, for example. These probes are detectable nucleotide sequences that can be detectable by virtue of an appropriate label or may be made inherently fluorescent as described in International Application No. WO 93/16094. The probes (and the polynucleotides of the subject invention) may be DNA, RNA, or PNA. In addition to adenine (A), cytosine (C), guanine (G), thymine (T), and uracil (U; for RNA molecules), synthetic probes (and polynucleotides) of the subject invention can also have inosine (a neutral base capable of pairing with all four bases; sometimes used in place of a mixture of all four bases in synthetic probes) and/or other synthetic (non-natural) bases. Thus, where a synthetic, degenerate oligonucleotide is referred to herein, and "N" or "n" is used generically, "N" or "n" can be G, A, T, C, or inosine. Ambiguity codes as used herein are in accordance with standard IUPAC naming conventions as of the filing of the subject application (for example, R means A or G, Y means C or T, etc.).

As is well known in the art, if a probe molecule hybridizes with a nucleic acid sample, it can be reasonably assumed that the probe and sample have substantial homology/similarity/identity. Preferably, hybridization of the polynucleotide is first conducted followed by washes under conditions of low, moderate, or high stringency by techniques well-known in the art, as described in, for example, Keller, G. H., M. M. Manak (1987) DNA Probes, Stockton Press, New York, N.Y., pp. 169-170. For example, as stated therein, low stringency conditions can be achieved by first washing with 2×SSC (Standard Saline Citrate)/0.1% SDS (Sodium Dodecyl Sulfate) for 15 minutes at room temperature. Two washes are typically performed. Higher stringency can then be achieved by lowering the salt concentration and/or by raising the temperature. For example, the wash described above can be followed by two washings with 0.1×SSC/0.1% SDS for 15 minutes each at room temperature followed by subsequent washes with 0.1×SSC/0.1% SDS for 30 minutes each at 55° C. These temperatures can be used with other hybridization and wash protocols set forth herein and as would be known to one skilled in the art (SSPE can be used as the salt instead of SSC, for example). The 2×SSC/0.1% SDS can be prepared by adding 50 ml of 20×SSC and 5 ml of 10% SDS to 445 ml of water. 20×SSC can be prepared by combining NaCl (175.3 g/0.150 M), sodium citrate (88.2 g/0.015 M), and water, adjusting pH to 7.0 with 10 N NaOH, then adjusting the volume to 1 liter. 10% SDS can be prepared by dissolving 10 g of SDS in 50 ml of autoclaved water, then diluting to 100 ml.

Detection of the probe provides a means for determining in a known manner whether hybridization has been maintained. Such a probe analysis provides a rapid method for identifying genes of the subject invention. The nucleotide segments used as probes according to the invention can be synthesized using a DNA synthesizer and standard procedures. These nucleotide sequences can also be used as PCR primers to amplify genes of the subject invention.

Hybridization characteristics of a molecule can be used to define polynucleotides of the subject invention. Thus the subject invention includes polynucleotides (and/or their complements, preferably their full complements) that hybridize with a polynucleotide exemplified herein. That is, one way to define a gene (and the protein it encodes), for example, is by its ability to hybridize (under any of the conditions specifically disclosed herein) with a known or specifically exemplified gene.

As used herein, "stringent" conditions for hybridization refers to conditions which achieve the same, or about the same, degree of specificity of hybridization as the conditions employed by the current applicants. Specifically, hybridization of immobilized DNA on Southern blots with $^{32}$P-labeled gene-specific probes can be performed by standard methods (see, e.g., Maniatis et al. 1982). In general, hybridization and subsequent washes can be carried out under conditions that allow for detection of target sequences. For double-stranded DNA gene probes, hybridization can be carried out overnight at 20-25° C. below the melting temperature (Tm) of the DNA hybrid in 6×SSPE, 5×Denhardt's solution, 0.1% SDS, 0.1 mg/ml denatured DNA. The melting temperature is described by the following formula (Beltz et al. 1983):

$$Tm = 81.5° C. + 16.6 \text{ Log } [Na+] + 0.41(\% G+C) - 0.61(\% \text{ formamide}) - 600/\text{length of duplex in base pairs.}$$

Washes can typically be carried out as follows:
(1) Twice at room temperature for 15 minutes in 1×SSPE, 0.1% SDS (low stringency wash).
(2) Once at Tm−20° C. for 15 minutes in 0.2×SSPE, 0.1% SDS (moderate stringency wash).

For oligonucleotide probes, hybridization can be carried out overnight at 10-20° C. below the melting temperature (Tm) of the hybrid in 6×SSPE, 5×Denhardt's solution, 0.1% SDS, 0.1 mg/ml denatured DNA. Tm for oligonucleotide probes can be determined by the following formula:

$$Tm(° C.) = 2(\text{number } T/A \text{ base pairs}) + 4(\text{number } G/C \text{ base pairs})$$

(Suggs et al., 1981).

Washes can typically be out as follows:
(1) Twice at room temperature for 15 minutes 1×SSPE, 0.1% SDS (low stringency wash).
(2) Once at the hybridization temperature for 15 minutes in 1×SSPE, 0.1% SDS (moderate stringency wash).

In general, salt and/or temperature can be altered to change stringency. With a labeled DNA fragment >70 or so bases in length, the following conditions can be used:
Low: 1 or 2×SSPE, room temperature
Low: 1 or 2×SSPE, 42° C.
Moderate: 0.2× or 1×SSPE, 65° C.
High: 0.1×SSPE, 65° C.

Duplex formation and stability depend on substantial complementarity between the two strands of a hybrid, and, as noted above, a certain degree of mismatch can be tolerated. Therefore, the probe sequences of the subject invention include mutations (both single and multiple), deletions, insertions of the described sequences, and combinations thereof, wherein said mutations, insertions and deletions permit formation of stable hybrids with the target polynucleotide of interest. Mutations, insertions, and deletions can be produced in a given polynucleotide sequence in many ways, and these methods are known to an ordinarily skilled artisan. Other methods may become known in the future.

PCR Technology.

Polymerase Chain Reaction (PCR) is a repetitive, enzymatic, primed synthesis of a nucleic acid sequence. This procedure is well known and commonly used by those skilled in this art (see Mullis, U.S. Pat. Nos. 4,683,195, 4,683,202, and 4,800,159; Saiki et al., 1985). PCR is based on the enzymatic amplification of a DNA fragment of interest that is flanked by two oligonucleotide primers that hybridize to opposite strands of the target sequence. The primers are preferably oriented with the 3' ends pointing towards each other. Repeated cycles of heat denaturation of the template, annealing of the primers to their complementary sequences, and extension of the annealed primers with a DNA polymerase result in the amplification of the segment defined by the 5' ends of the PCR primers. The extension product of each primer can serve as a template for the other primer, so each cycle essentially doubles the amount of DNA fragment produced in the previous cycle. This results in the exponential accumulation of the specific target fragment, up to several million-fold in a few hours. By using a thermostable DNA polymerase such as Taq polymerase, isolated from the thermophilic bacterium *Thermus aquaticus*, the amplification process can be completely automated. Other enzymes which can be used are known to those skilled in the art.

Exemplified DNA sequences, or segments thereof, can be used as primers for PCR amplification. In performing PCR amplification, a certain degree of mismatch can be tolerated between primer and template. Therefore, mutations, deletions, and insertions (especially additions of nucleotides to the 5' end) of the exemplified primers fall within the scope of the subject invention. Mutations, insertions, and deletions can be produced in a given primer by methods known to an ordinarily skilled artisan.

Modification of Genes and Proteins.

The subject genes and proteins can be fused to other genes and proteins to produce chimeric or fusion proteins. The genes and proteins useful according to the subject invention include not only the specifically exemplified full-length sequences, but also portions, segments and/or fragments (including contiguous fragments and internal and/or terminal deletions compared to the full-length molecules) of these sequences, variants, mutants, chimerics, and fusions thereof. Proteins of the subject invention can have substituted amino acids so long as they retain desired functional activity. "Variant" genes have nucleotide sequences that encode the same proteins or equivalent proteins having activity equivalent or similar to an exemplified protein.

The top two results of BLAST searches with the native aad-12 nucleotide sequence show a reasonable level of homology (about 85%) over 120 basepairs of sequence. Hybridization under certain conditions could be expected to include these two sequences. See GENBANK Acc. Nos. DQ406818.1 (89329742; *Rhodoferax*) and AJ6288601.1 (44903451; *Sphingomonas*). *Rhodoferax* is very similar to *Delftia* but *Sphingomonas* is an entirely different Class phylogenetically.

The terms "variant proteins" and "equivalent proteins" refer to proteins having the same or essentially the same biological/functional activity against the target substrates and equivalent sequences as the exemplified proteins. As used herein, reference to an "equivalent" sequence refers to sequences having amino acid substitutions, deletions, additions, or insertions that improve or do not adversely affect activity to a significant extent. Fragments retaining activity are also included in this definition. Fragments and other equivalents that retain the same or similar function or activity as a corresponding fragment of an exemplified protein are within the scope of the subject invention. Changes, such as amino acid substitutions or additions, can be made for a variety of purposes, such as increasing (or decreasing) protease stability of the protein (without materially/substantially decreasing the functional activity of the protein), removing or adding a restriction site, and the like. Variations of genes may be readily constructed using standard techniques for making point mutations, for example.

In addition, U.S. Pat. No. 5,605,793, for example, describes methods for generating additional molecular diversity by using DNA reassembly after random or focused fragmentation. This can be referred to as gene "shuffling," which typically involves mixing fragments (of a desired size) of two or more different DNA molecules, followed by repeated rounds of renaturation. This can improve the activity of a protein encoded by a starting gene. The result is a chimeric protein having improved activity, altered substrate specificity, increased enzyme stability, altered stereospecificity, or other characteristics.

"Shuffling" can be designed and targeted after obtaining and examining the atomic 3D (three dimensional) coordinates and crystal structure of a protein of interest. Thus, "focused shuffling" can be directed to certain segments of a protein that are ideal for modification, such as surface-exposed segments, and preferably not internal segments that are involved with protein folding and essential 3D structural integrity.

Figure 2:
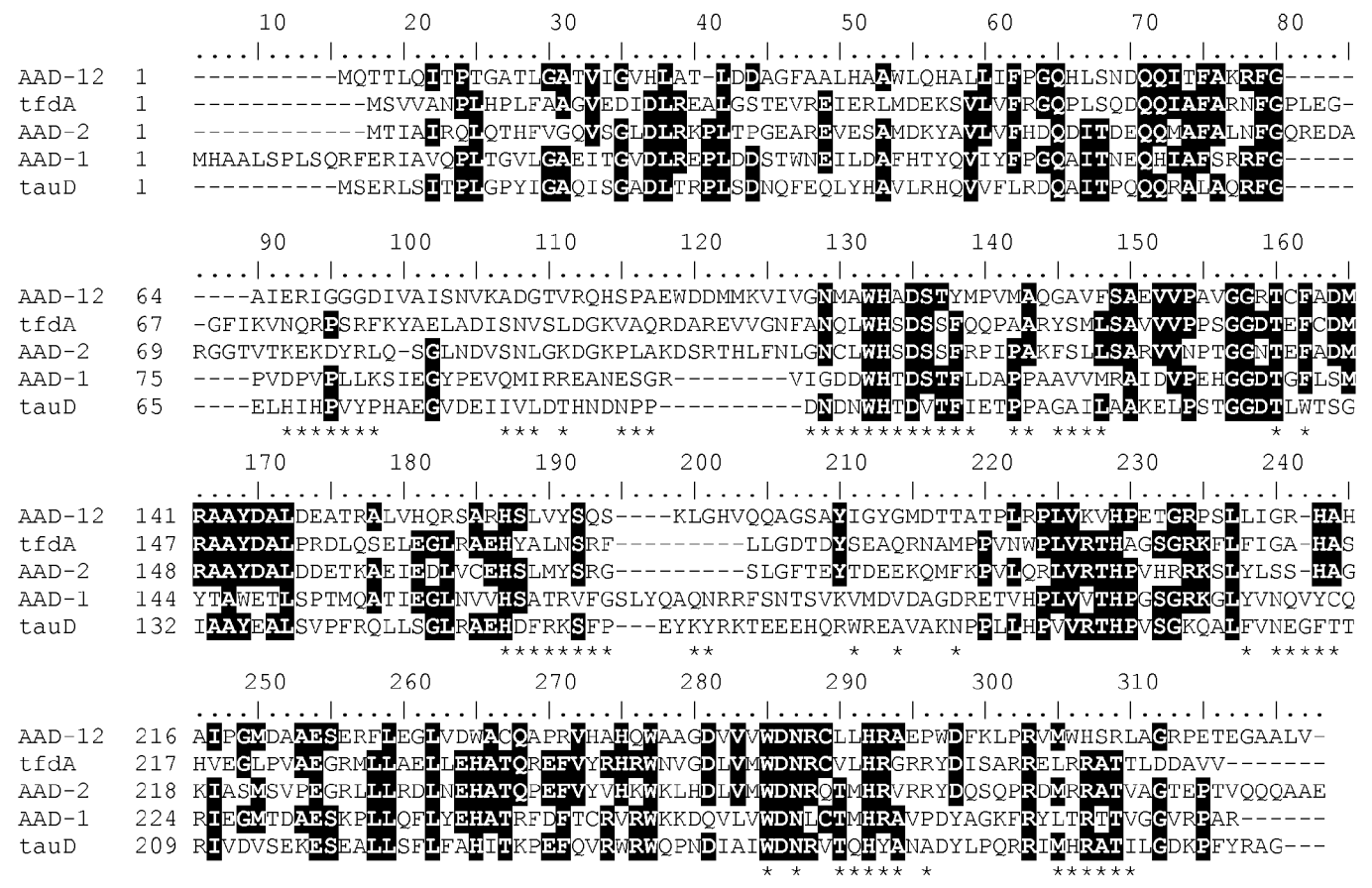

Specific changes to the "active site" of the enzyme can be made to affect the inherent functionallity with respect to activity or stereospecificity (see alignment FIG. 2). Muller et. al. (2006). The known tauD crystal structure was used as a model dioxygenase to determine active site residues while bound to its inherent substrate taurine. Elkins et al. (2002) "X-ray crystal structure of *Escherichia coli* taurine/alpha-ketoglutarate dioxygenase complexed to ferrous iron and substrates," Biochemistry 41(16):5185-5192. Regarding sequence optimization and designability of enzyme active sites, see Chakrabarti et al., PNAS, (Aug. 23, 2005), 102 (34):12035-12040.

Variant genes can be used to produce variant proteins; recombinant hosts can be used to produce the variant proteins. Using these "gene shuffling" techniques, equivalent genes and proteins can be constructed that comprise any 5, 10, or 20 contiguous residues (amino acid or nucleotide) of any sequence exemplified herein. As one skilled in the art knows, the gene shuffling techniques, for example, can be adjusted to obtain equivalents having, for example, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, or 293 contiguous residues (amino acid or nucleotide), corresponding to a segment (of the same size) in any of the exemplified or suggested sequences (or the complements (full complements) thereof). Similarly sized segments, especially those for conserved regions, can also be used as probes and/or primers.

Fragments of full-length genes can be made using commercially available exonucleases or endonucleases according to standard procedures. For example, enzymes such as Bal31 or site-directed mutagenesis can be used to systematically cut off nucleotides from the ends of these genes. Also, genes that encode active fragments may be obtained using a variety of restriction enzymes. Proteases may be used to directly obtain active fragments of these proteins.

It is within the scope of the invention as disclosed herein that proteins can be truncated and still retain functional activity. By "truncated protein" it is meant that a portion of a protein may be cleaved off while the remaining truncated protein retains and exhibits the desired activity after cleavage. Cleavage can be achieved by various proteases. Furthermore, effectively cleaved proteins can be produced using molecular biology techniques wherein the DNA bases encoding said protein are removed either through digestion with restriction endonucleases or other techniques available to the skilled artisan. After truncation, said proteins can be expressed in heterologous systems such as *E. coli*, baculoviruses, plant-based viral systems, yeast, and the like and then placed in insect assays as disclosed herein to determine activity. It is well-known in the art that truncated proteins can be successfully produced so that they retain functional activity while having less than the entire, full-length sequence. For example, B.t. proteins can be used in a truncated (core protein) form (see, e.g., Höfte et al. (1989), and Adang et al. (1985)). As used herein, the term "protein" can include functionally active truncations.

In some cases, especially for expression in plants, it can be advantageous to use truncated genes that express truncated proteins. Preferred truncated genes will typically encode 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the full-length protein.

Certain proteins of the subject invention have been specifically exemplified herein. As these proteins are merely exemplary of the proteins of the subject invention, it should be readily apparent that the subject invention comprises variant or equivalent proteins (and nucleotide sequences coding for equivalents thereof) having the same or similar activity of the exemplified proteins. Equivalent proteins will have amino acid similarity (and/or homology) with an exemplified protein. The amino acid identity will typically be at least 60%, preferably at least 75%, more preferably at least 80%, even more preferably at least 90%, and can be at least 95%. Preferred proteins of the subject invention can also be defined in terms of more particular identity and/or similarity ranges. For example, the identity and/or similarity can be 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% as compared to a sequence exemplified or suggested herein. Any number listed above can be used to define the upper and lower limits.

Unless otherwise specified, as used herein, percent sequence identity and/or similarity of two nucleic acids is determined using the algorithm of Karlin and Altschul, 1990, modified as in Karlin and Altschul 1993. Such an algorithm is incorporated into the NBLAST and XBLAST programs of Altschul et al., 1990. BLAST nucleotide searches are performed with the NBLAST program, score=100, wordlength=12. Gapped BLAST can be used as described in Altschul et al., 1997. When utilizing BLAST and Gapped BLAST programs, the default parameters of the respective programs (NBLAST and XBLAST) are used. See NCBI/NIH website. To obtain gapped alignments for comparison purposes, the AlignX function of Vector NTI Suite 8 (InforMax, Inc., North Bethesda, Md., U.S.A.), was used employing the default parameters. These were: a Gap opening penalty of 15, a Gap extension penalty of 6.66, and a Gap separation penalty range of 8.

Various properties and three-dimensional features of the protein can also be changed without adversely affecting the activity/functionality of the protein. Conservative amino acid substitutions can be tolerated/made to not adversely affect the activity and/or three-dimensional configuration of the molecule. Amino acids can be placed in the following classes: non-polar, uncharged polar, basic, and acidic. Conservative substitutions whereby an amino acid of one class is replaced with another amino acid of the same type fall within the scope of the subject invention so long as the substitution is not adverse to the biological activity of the compound. Table 2 provides a listing of examples of amino acids belonging to each class.

TABLE 2

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. However, preferred substitutions do not significantly detract from the functional/biological activity of the protein.

As used herein, reference to "isolated" polynucleotides and/or "purified" proteins refers to these molecules when they are not associated with the other molecules with which they would be found in nature. Thus, reference to "isolated" and/or "purified" signifies the involvement of the "hand of man" as described herein. For example, a bacterial "gene" of the subject invention put into a plant for expression is an "isolated polynucleotide." Likewise, a protein derived from a bacterial protein and produced by a plant is an "isolated protein."

Because of the degeneracy/redundancy of the genetic code, a variety of different DNA sequences can encode the amino acid sequences disclosed herein. It is well within the skill of a person trained in the art to create alternative DNA sequences that encode the same, or essentially the same, proteins. These variant DNA sequences are within the scope of the subject invention. This is also discussed in more detail below in the section entitled "Optimization of sequence for expression in plants."

Optimization of Sequence for Expression in Plants.

To obtain high expression of heterologous genes in plants it is generally preferred to reengineer the genes so that they are more efficiently expressed in (the cytoplasm of) plant cells. Maize is one such plant where it may be preferred to re-design the heterologous gene(s) prior to transformation to increase the expression level thereof in said plant. Therefore, an additional step in the design of genes encoding a bacterial protein is reengineering of a heterologous gene for optimal expression, using codon bias more closely aligned with the target plant sequence, whether a dicot or monocot species. Sequences can also be optimized for expression in any of the more particular types of plants discussed elsewhere herein.

Transgenic Hosts.

The protein-encoding genes of the subject invention can be introduced into a wide variety of microbial or plant hosts. The subject invention includes transgenic plant cells and transgenic plants. Preferred plants (and plant cells) are corn, *Arabidopsis*, tobacco, soybeans, cotton, canola, rice, wheat, turf, legume forages (e.g., alfalfa and clover), pasture grasses, and the like. Other types of transgenic plants can also be made according to the subject invention, such as fruits, vegetables, ornamental plants, and trees. More generally, dicots and/or monocots can be used in various aspects of the subject invention.

In preferred embodiments, expression of the gene results, directly or indirectly, in the intracellular production (and maintenance) of the protein(s) of interest. Plants can be rendered herbicide-resistant in this manner. Such hosts can be referred to as transgenic, recombinant, transformed, and/or transfected hosts and/or cells. In some aspects of this invention (when cloning and preparing the gene of interest, for example), microbial (preferably bacterial) cells can be produced and used according to standard techniques, with the benefit of the subject disclosure.

Plant cells transfected with a polynucleotide of the subject invention can be regenerated into whole plants. The subject invention includes cell cultures including tissue cell cultures, liquid cultures, and plated cultures. Seeds produced by and/or used to generate plants of the subject invention are also included within the scope of the subject invention. Other plant tissues and parts are also included in the subject invention. The subject invention likewise includes methods of producing plants or cells comprising a polynucleotide of the subject invention. One preferred method of producing such plants is by planting a seed of the subject invention.

Although plants can be preferred, the subject invention also includes production of highly active recombinant AAD-12 in a *Pseudomonas fluorescens* (Pf) host strain, for example. The subject invention includes preferred growth temperatures for maintaining soluble active AAD-12 in this host; a fermentation condition where AAD-12 is produced as more than 40% total cell protein, or at least 10 g/L; a purification process results high recovery of active recombinant AAD-12 from a Pf host; a purification scheme which yields at least 10 g active AAD-12 per kg of cells; a purification scheme which can yield 20 g active AAD-12 per kg of cells; a formulation process that can store and restore AAD-12 activity in solution; and a lyophilization process that can retain AAD-12 activity for long-term storage and shelf life.

Insertion of Genes to Form Transgenic Hosts.

One aspect of the subject invention is the transformation/transfection of plants, plant cells, and other host cells with polynucleotides of the subject invention that express proteins of the subject invention. Plants transformed in this manner can be rendered resistant to a variety of herbicides with different modes of action.

A wide variety of methods are available for introducing a gene encoding a desired protein into the target host under conditions that allow for stable maintenance and expression of the gene. These methods are well known to those skilled in the art and are described, for example, in U.S. Pat. No. 5,135,867.

Vectors comprising an AAD-12 polynucleotide are included in the scope of the subject invention. For example, a large number of cloning vectors comprising a replication system in *E. coli* and a marker that permits selection of the transformed cells are available for preparation for the insertion of foreign genes into higher plants. The vectors comprise, for example, pBR322, pUC series, M13mp series, pACYC184, etc. Accordingly, the sequence encoding the protein can be inserted into the vector at a suitable restriction site. The resulting plasmid is used for transformation into *E. coli*. The *E. coli* cells are cultivated in a suitable nutrient medium, then harvested and lysed. The plasmid is recovered by purification away from genomic DNA. Sequence analysis, restriction analysis, electrophoresis, and other biochemical-molecular biological methods are generally carried out as methods of analysis. After each manipulation, the DNA sequence used can be restriction digested and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted. The use of T-DNA for the transformation of plant cells has been intensively researched and described in EP 120 516; Hoekema (1985); Fraley et al. (1986); and An et al. (1985).

A large number of techniques are available for inserting DNA into a plant host cell. Those techniques include transformation with T-DNA using *Agrobacterium tumefaciens* or *Agrobacterium rhizogenes* as transformation agent, fusion, injection, biolistics (microparticle bombardment), silicon carbide whiskers, aerosol beaming, PEG, or electroporation as well as other possible methods. If Agrobacteria are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in Agrobacteria. The intermediate vector can be transferred into *Agrobacterium tumefaciens* by means of a helper plasmid (conjugation). Binary vectors can replicate themselves both in *E. coli* and in Agrobacteria. They comprise a selection marker gene and a linker or polylinker which are framed by the right and left T-DNA border regions. They can be transformed directly into Agrobacteria (Holsters, 1978). The *Agrobacterium* used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can be cultivated advantageously with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives.

The transformed cells grow inside the plants in the usual manner. They can form germ cells and transmit the transformed trait(s) to progeny plants. Such plants can be grown in the normal manner and crossed with plants that have the same transformed hereditary factors or other hereditary factors. The resulting hybrid individuals have the corresponding phenotypic properties.

In some preferred embodiments of the invention, genes encoding the bacterial protein are expressed from transcriptional units inserted into the plant genome. Preferably, said transcriptional units are recombinant vectors capable of stable integration into the plant genome and enable selection of transformed plant lines expressing mRNA encoding the proteins.

Once the inserted DNA has been integrated in the genome, it is relatively stable there (and does not come out again). It normally contains a selection marker that confers on the transformed plant cells resistance to a biocide or an antibiotic, such as kanamycin, G418, bleomycin, hygromycin, or chloramphenicol, inter alia. Plant selectable markers also typically can provide resistance to various herbicides such as glufosinate (e.g., PAT/bar), glyphosate (EPSPS), ALS-inhibitors (e.g., imidazolinone, sulfonylurea, triazolopyrimidine sulfonanilide, et al.), bromoxynil, HPPD-inhibitor resistance, PPO-inhibitors, ACC-ase inhibitors, and many others. The individually employed marker should accordingly permit the selection of transformed cells rather than cells that do not contain the inserted DNA. The gene(s) of interest are preferably expressed either by constitutive or inducible promoters in the plant cell. Once expressed, the mRNA is translated into proteins, thereby incorporating amino acids of interest into protein. The genes encoding a protein expressed in the plant cells can be under the control of a constitutive promoter, a tissue-specific promoter, or an inducible promoter.

Several techniques exist for introducing foreign recombinant vectors into plant cells, and for obtaining plants that stably maintain and express the introduced gene. Such techniques include the introduction of genetic material coated onto microparticles directly into cells (U.S. Pat. No. 4,945,050 to Cornell and U.S. Pat. No. 5,141,131 to Dow-Elanco, now Dow AgroSciences, LLC). In addition, plants may be transformed using *Agrobacterium* technology, see U.S. Pat. No. 5,177,010 to University of Toledo; U.S. Pat. No. 5,104,310 to Texas A&M; European Patent Application 0131624B1; European Patent Applications 120516, 159418B1 and 176,112 to Schilperoot; U.S. Pat. Nos. 5,149, 645, 5,469,976, 5,464,763 and 4,940,838 and 4,693,976 to Schilperoot; European Patent Applications 116718, 290799, 320500, all to Max Planck; European Patent Applications 604662 and 627752, and U.S. Pat. No. 5,591,616, to Japan Tobacco; European Patent Applications 0267159 and 0292435, and U.S. Pat. No. 5,231,019, all to Ciba Geigy, now Syngenta; U.S. Pat. Nos. 5,463,174 and 4,762,785, both to Calgene; and U.S. Pat. Nos. 5,004,863 and 5,159,135, both to Agracetus. Other transformation technology includes whiskers technology. See U.S. Pat. Nos. 5,302,523 and 5,464,765, both to Zeneca, now Syngenta. Other direct DNA delivery transformation technology includes aerosol beam technology. See U.S. Pat. No. 6,809,232. Electroporation technology has also been used to transform plants. See WO 87/06614 to Boyce Thompson Institute; U.S. Pat. Nos. 5,472,869 and 5,384,253, both to Dekalb; and WO 92/09696 and WO 93/21335, both to Plant Genetic Systems. Furthermore, viral vectors can also be used to produce transgenic plants expressing the protein of interest. For example, monocotyledonous plants can be transformed with a viral vector using the methods described in U.S. Pat. No. 5,569,597 to Mycogen Plant Science and Ciba-Geigy (now Syngenta), as well as U.S. Pat. Nos. 5,589,367 and 5,316,931, both to Biosource, now Large Scale Biology.

As mentioned previously, the manner in which the DNA construct is introduced into the plant host is not critical to this invention. Any method that provides for efficient transformation may be employed. For example, various methods for plant cell transformation are described herein and include the use of Ti or Ri-plasmids and the like to perform *Agrobacterium* mediated transformation. In many instances, it will be desirable to have the construct used for transformation bordered on one or both sides by T-DNA borders, more specifically the right border. This is particularly useful when the construct uses *Agrobacterium tumefaciens* or *Agrobacterium rhizogenes* as a mode for transformation, although T-DNA borders may find use with other modes of transformation. Where *Agrobacterium* is used for plant cell transformation, a vector may be used which may be introduced into the host for homologous recombination with T-DNA or the Ti or Ri plasmid present in the host. Introduction of the vector may be performed via electroporation, tri-parental mating and other techniques for transforming gram-negative bacteria which are known to those skilled in the art. The manner of vector transformation into the *Agrobacterium* host is not critical to this invention. The Ti or Ri plasmid containing the T-DNA for recombination may be capable or incapable of causing gall formation, and is not critical to said invention so long as the vir genes are present in said host.

In some cases where *Agrobacterium* is used for transformation, the expression construct being within the T-DNA borders will be inserted into a broad spectrum vector such as pRK2 or derivatives thereof as described in Ditta et al. (1980) and EPO 0 120 515. Included within the expression construct and the T-DNA will be one or more markers as described herein which allow for selection of transformed *Agrobacterium* and transformed plant cells. The particular marker employed is not essential to this invention, with the preferred marker depending on the host and construction used.

For transformation of plant cells using *Agrobacterium*, explants may be combined and incubated with the transformed *Agrobacterium* for sufficient time to allow transformation thereof. After transformation, the Agrobacteria are killed by selection with the appropriate antibiotic and plant cells are cultured with the appropriate selective medium. Once calli are formed, shoot formation can be encouraged by employing the appropriate plant hormones according to methods well known in the art of plant tissue culturing and plant regeneration. However, a callus intermediate stage is not always necessary. After shoot formation, said plant cells can be transferred to medium which encourages root formation thereby completing plant regeneration. The plants may then be grown to seed and said seed can be used to establish future generations. Regardless of transformation technique, the gene encoding a bacterial protein is preferably incorporated into a gene transfer vector adapted to express said gene in a plant cell by including in the vector a plant promoter regulatory element, as well as 3' non-translated transcriptional termination regions such as Nos and the like.

In addition to numerous technologies for transforming plants, the type of tissue that is contacted with the foreign genes may vary as well. Such tissue would include but would not be limited to embryogenic tissue, callus tissue types I, II, and III, hypocotyl, meristem, root tissue, tissues for expression in phloem, and the like. Almost all plant tissues may be transformed during dedifferentiation using appropriate techniques described herein.

As mentioned above, a variety of selectable markers can be used, if desired. Preference for a particular marker is at the discretion of the artisan, but any of the following selectable markers may be used along with any other gene not listed herein which could function as a selectable marker. Such selectable markers include but are not limited to aminoglycoside phosphotransferase gene of transposon Tn5 (Aph II) which encodes resistance to the antibiotics kanamycin, neomycin and G41; hygromycin resistance; methotrexate resistance, as well as those genes which encode for resistance or tolerance to glyphosate; phosphinothricin (bialaphos or glufosinate); ALS-inhibiting herbicides (imidazolinones, sulfonylureas and triazolopyrimidine herbicides), ACC-ase inhibitors (e.g., ayryloxypropionates or cyclohexanediones), and others such as bromoxynil, and HPPD-inhibitors (e.g., mesotrione) and the like.

In addition to a selectable marker, it may be desirous to use a reporter gene. In some instances a reporter gene may be used with or without a selectable marker. Reporter genes are genes that are typically not present in the recipient organism or tissue and typically encode for proteins resulting in some phenotypic change or enzymatic property. Examples of such genes are provided in Weising et al., 1988. Preferred reporter genes include the beta-glucuronidase (GUS) of the uidA locus of *E. coli*, the chloramphenicol acetyl transferase gene from Tn9 of *E. coli*, the green fluorescent protein from the bioluminescent jellyfish *Aequorea victoria*, and the luciferase genes from firefly *Photinus pyralis*. An assay for detecting reporter gene expression may then be performed at a suitable time after said gene has been introduced into recipient cells. A preferred such assay entails the use of the gene encoding beta-glucuronidase (GUS) of the uidA locus of *E. coli* as described by Jefferson et al., (1987) to identify transformed cells.

In addition to plant promoter regulatory elements, promoter regulatory elements from a variety of sources can be used efficiently in plant cells to express foreign genes. For example, promoter regulatory elements of bacterial origin, such as the octopine synthase promoter, the nopaline synthase promoter, the mannopine synthase promoter; promoters of viral origin, such as the cauliflower mosaic virus (35S and 19S), 35T (which is a re-engineered 35S promoter, see U.S. Pat. No. 6,166,302, especially Example 7E) and the like may be used. Plant promoter regulatory elements include but are not limited to ribulose-1,6-bisphosphate (RUBP) carboxylase small subunit (ssu), beta-conglycinin promoter, beta-phaseolin promoter, ADH promoter, heat-shock promoters, and tissue specific promoters. Other elements such as matrix attachment regions, scaffold attachment regions, introns, enhancers, polyadenylation sequences and the like may be present and thus may improve the transcription efficiency or DNA integration. Such elements may or may not be necessary for DNA function, although they can provide better expression or functioning of the DNA by affecting transcription, mRNA stability, and the like. Such elements may be included in the DNA as desired to obtain optimal performance of the transformed DNA in the plant. Typical elements include but are not limited to Adh-intron 1, Adh-intron 6, the alfalfa mosaic virus coat protein leader sequence, osmotin UTR sequences, the maize streak virus coat protein leader sequence, as well as others available to a skilled artisan. Constitutive promoter regulatory elements may also be used thereby directing continuous gene expression in all cells types and at all times (e.g., actin, ubiquitin, CaMV 35S, and the like). Tissue specific promoter regulatory elements are responsible for gene expression in specific cell or tissue types, such as the leaves or seeds (e.g., zein, oleosin, napin, ACP, globulin and the like) and these may also be used.

Promoter regulatory elements may also be active (or inactive) during a certain stage of the plant's development as well as active in plant tissues and organs. Examples of such include but are not limited to pollen-specific, embryo-specific, corn-silk-specific, cotton-fiber-specific, root-specific, seed-endosperm-specific, or vegetative phase-specific promoter regulatory elements and the like. Under certain circumstances it may be desirable to use an inducible promoter regulatory element, which is responsible for expression of genes in response to a specific signal, such as: physical stimulus (heat shock genes), light (RUBP carboxylase), hormone (Em), metabolites, chemical (tetracycline responsive), and stress. Other desirable transcription and translation elements that function in plants may be used. Numerous plant-specific gene transfer vectors are known in the art.

Plant RNA viral based systems can also be used to express bacterial protein. In so doing, the gene encoding a protein can be inserted into the coat promoter region of a suitable plant virus which will infect the host plant of interest. The protein can then be expressed thus providing protection of the plant from herbicide damage. Plant RNA viral based systems are described in U.S. Pat. No. 5,500,360 to Mycogen Plant Sciences, Inc. and U.S. Pat. Nos. 5,316,931 and 5,589,367 to Biosource, now Large Scale Biology.

Means of Further Increasing Tolerance or Resistance Levels.

It is shown herein that plants of the subject invention can be imparted with novel herbicide resistance traits without observable adverse effects on phenotype including yield. Such plants are within the scope of the subject invention. Plants exemplified and suggested herein can withstand 2x, 3x, 4x, and 5x typical application levels, for example, of at least one subject herbicide. Improvements in these tolerance levels are within the scope of this invention. For example, various techniques are know in the art, and can forseeably be optimized and further developed, for increasing expression of a given gene.

One such method includes increasing the copy number of the subject AAD-12 genes (in expression cassettes and the like). Transformation events can also be selected for those having multiple copies of the genes.

Strong promoters and enhancers can be used to "supercharge" expression. Examples of such promoters include the preferred 35T promoter which uses 35S enhancers. 35S, maize ubiquitin, *Arabidopsis* ubiquitin, A.t. actin, and CSMV promoters are included for such uses. Other strong viral promoters are also preferred. Enhancers include 4 OCS and the 35S double enhancer. Matrix attachment regions (MARs) can also be used to increase transformation efficiencies and transgene expression, for example.

Shuffling (directed evolution) and transcription factors can also be used for embodiments according to the subject invention.

Variant proteins can also be designed that differ at the sequence level but that retain the same or similar overall essential three-dimensional structure, surface charge distribution, and the like. See e.g. U.S. Pat. No. 7,058,515; Larson et al., Protein Sci. 2002 11: 2804-2813, "Thoroughly sampling sequence space: Large-scale protein design of structural ensembles."; Crameri et al., *Nature Biotechnology* 15, 436-438 (1997), "Molecular evolution of an arsenate detoxification pathway by DNA shuffling."; Stemmer, W.P.C. 1994. DNA shuffling by random fragmentation and reassembly: in vitro recombination for molecular evolution. Proc. Natl. Acad. Sci. USA 91: 10747-10751; Stemmer, W.P.C. 1994. Rapid evolution of a protein in vitro by DNA shuffling. Nature 370: 389-391; Stemmer, W.P.C. 1995. Searching sequence space. Bio/Technology 13: 549-553; Crameri, A., Cwirla, S. and Stemmer, W.P.C. 1996. Construction and evolution of antibody-phage libraries by DNA shuffling. Nature Medicine 2: 100-103; and Crameri, A., Whitehorn, E. A., Tate, E. and Stemmer, W.P.C. 1996. Improved green fluorescent protein by molecular evolution using DNA shuffling. Nature Biotechnology 14: 315-319.

The activity of recombinant polynucleotides inserted into plant cells can be dependent upon the influence of endogenous plant DNA adjacent the insert. Thus, another option is taking advantage of events that are known to be excellent locations in a plant genome for insertions. See e.g. WO 2005/103266 A1, relating to cry1F and cry1Ac cotton events; the subject AAD-12 gene can be substituted in those genomic loci in place of the cry1F and/or cry1Ac inserts. Thus, targeted homologous recombination, for example, can be used according to the subject invention. This type of technology is the subject of, for example, WO 03/080809 A2 and the corresponding published U.S. application (USPA 20030232410), relating to the use of zinc fingers for targeted recombination. The use of recombinases (cre-lox and flp-frt for example) is also known in the art.

AAD-12 detoxification is believed to occur in the cytoplasm. Thus, means for further stabilizing this protein and mRNAs (including blocking mRNA degradation) are included in aspects of the subject invention, and art-known techniques can be applied accordingly. The subject proteins can be designed to resist degradation by proteases and the like (protease cleavage sites can be effectively removed by re-engineering the amino acid sequence of the protein). Such embodiments include the use of 5' and 3' stem loop structures like UTRs from osmotin, and per5 (AU-rich untranslated 5' sequences). 5' caps like 7-methyl or 2'-O-methyl groups, e.g., 7-methylguanylic acid residue, can also be used. See, e.g.: Proc. Natl. Acad. Sci. USA Vol. 74, No. 7, pp. 2734-2738 (July 1977 *Importance of 5'-terminal blocking structure to stabilize mRNA in eukaryotic protein synthesis*. Protein complexes or ligand blocking groups can also be used.

Computational design of 5' or 3' UTR most suitable for AAD-12 (synthetic hairpins) can also be conducted within the scope of the subject invention. Computer modeling in general, as well as gene shuffling and directed evolution, are discussed elsewhere herein. More specifically regarding computer modeling and UTRs, computer modeling techniques for use in predicting/evaluating 5' and 3' UTR derivatives of the present invention include, but are not limited to: MFold version 3.1 available from Genetics Corporation Group, Madison, Wis. (see Zucker et al., Algorithms and Thermodynamics for RNA Secondary Structure Prediction: A Practical Guide. In RNA Biochemistry and Biotechnology, 11-43, J. Barciszewski & B. F. C. Clark, eds., NATO ASI Series, Kluwer Academic Publishers, Dordrecht, N L, (1999); Zucker et al., *Expanded Sequence Dependence of Thermodynamic Parameters Improves Prediction of RNA Secondary Structure. J. Mol. Biol.* 288, 911-940 (1999); Zucker et al., RNA Secondary Structure Prediction. In *Current Protocols in Nucleic Acid Chemistry* S. Beaucage, D. E. Bergstrom, G. D. Glick, and R. A. Jones eds., John Wiley & Sons, New York, 11.2.1-11.2.10, (2000)), COVE (RNA structure analysis using covariance models (stochastic context free grammar methods)) v. 2.4.2 (Eddy & Durbin, Nucl. Acids Res. 1994, 22: 2079-2088) which is freely distributed as source code and which can be downloaded by accessing the website genetics.wustl.edu/eddy/software/, and FOLDALIGN, also freely distributed and available for downloading at the website bioinf.au.dk. FOLDALIGN/ (see *Finding the most significant common sequence and structure motifs in a set of RNA sequences*. J. Gorodkin, L. J. Heyer and G. D. Stormo. Nucleic Acids Research, Vol. 25, no. 18 pp 3724-3732, 1997; *Finding Common Sequence and Structure Motifs in a set of RNA Sequences*. J. Gorodkin, L. J. Heyer, and G. D. Stormo. ISMB 5; 120-123, 1997).

Embodiments of the subject invention can be used in conjunction with naturally evolved or chemically induced mutants (mutants can be selected by screening techniques, then transformed with AAD-12 and possibly other genes). Plants of the subject invention can be combined with ALS resistance and/or evolved glyphosate resistance. Aminopyralid resistance, for example, can also be combined or "stacked" with an AAD-12 gene.

Traditional breeding techniques can also be combined with the subject invention to powerfully combine, introgress, and improve desired traits.

Further improvements also include use with appropriate safeners to further protect plants and/or to add cross resistance to more herbicides. (Safeners typically act to increase plants immune system by activating/expressing cP450. Safeners are chemical agents that reduce the phytotoxicity of herbicides to crop plants by a physiological or molecular mechanism, without compromising weed control efficacy.)

Herbicide safeners include benoxacor, cloquintocet, cyometrinil, dichlormid, dicyclonon, dietholate, fenchlorazole, fenclorim, flurazole, fluxofenim, furilazole, isoxadifen, mefenpyr, mephenate, naphthalic anhydride, and oxabetrinil. Plant activators (a new class of compounds that protect plants by activating their defense mechanisms) can also be used in embodiments of the subject invention. These include acibenzolar and probenazole.

Commercialized safeners can be used for the protection of large-seeded grass crops, such as corn, grain *sorghum*, and wet-sown rice, against preplant-incorporated or preemergence-applied herbicides of the thiocarbamate and chloroacetanilide families. Safeners also have been developed to protect winter cereal crops such as wheat against postemergence applications of aryloxyphenoxypropionate and sulfonylurea herbicides. The use of safeners for the protection of corn and rice against sulfonylurea, imidazolinone, cyclohexanedione, isoxazole, and triketone herbicides is also well-established. A safener-induced enhancement of herbicide detoxification in safened plants is widely accepted as the major mechanism involved in safener action. Safeners induce cofactors such as glutathione and herbicide-detoxifying enzymes such as glutathione S-transferases, cytochrome P450 monooxygenases, and glucosyl transferases. Hatzios K K, Burgos N (2004) "Metabolism-based herbicide resistance: regulation by safeners," Weed Science: Vol. 52, No. 3 pp. 454-467.

Use of a cytochrome p450 monooxygenase gene stacked with AAD-12 is one preferred embodiment. There are P450s involved in herbicide metabolism; cP450 can be of mammalian or plant origin, for example. In higher plants, cytochrome P450 monooxygenase (P450) is known to conduct secondary metabolism. It also plays an important role in the oxidative metabolism of xenobiotics in cooperation with NADPH-cytochrome P450 oxidoreductase (reductase). Resistance to some herbicides has been reported as a result of the metabolism by P450 as well as glutathione S-transferase. A number of microsomal P450 species involved in xenobiotic metabolism in mammals have been characterized by molecular cloning. Some of them were reported to metabolize several herbicides efficiently. Thus, transgenic plants with plant or mammalian P450 can show resistance to several herbicides.

One preferred embodiment of the foregoing is the use cP450 for resistance to acetochlor (acetochlor-based products include Surpass®, Keystone®, Keystone LA, FulTime® and TopNotch herbicides) and/or trifluralin (such as Treflan®). Such resistance in soybeans and/or corn is included in some preferred embodiments. For additional guidance regarding such embodiments, see e.g. Inui et al., "A selectable marker using cytochrome P450 monooxygenases for *Arabidopsis* transformation," *Plant Biotechnology* 22, 281-286 (2005) (relating to a selection system for transformation of *Arabidopsis thaliana* via *Agrobacterium tumefaciens* that uses human cytochrome P450 monooxygenases that metabolize herbicides; herbicide tolerant seedlings were transformed and selected with the herbicides acetochlor, amiprophos-methyl, chlorpropham, chlorsulfuron, norflurazon, and pendimethalin); Siminszky et al., "Expression of a soybean cytochrome P450 monooxygenase cDNA in yeast and tobacco enhances the metabolism of phenylurea herbicides," *PNAS* Vol. 96, Issue 4, 1750-1755, Feb. 16, 1999; Sheldon et al, *Weed Science*: Vol. 48, No. 3, pp. 291-295, "A cytochrome P450 monooxygenase cDNA (CYP71A10) confers resistance to linuron in transgenic *Nicotiana tabacum*"; and "Phytoremediation of the herbicides atrazine and metolachlor by transgenic rice plants expressing human CYP1A1, CYP2B6, and CYP2C19," *J Agric Food Chem.* 2006 Apr. 19; 54(8):2985-91 (relating to testing a human cytochrome p450 monooxygenase in rice where the rice plants reportedly showed high tolerance to chloroacetomides (acetochlor, alachlor, metoachlor, pretilachlor, and thenylchlor), oxyacetamides (mefenacet), pyridazinones (norflurazon), 2,6-dinitroanalines (trifluralin and pendimethalin), phosphamidates (amiprofos-methyl, thiocarbamates (pyributicarb), and ureas (chlortoluron)).

There is also the possibility of altering or using different 2,4-D chemistries to make the subject AAD-12 genes more efficient. Such possible changes include creating better substrates and better leaving groups (higher electronegativity).

Auxin transport inhibitors (e.g. diflufenzopyr) can also be used to increase herbicide activity with 2,4-D.

Unless specifically indicated or implied, the terms "a", "an", and "the" signify "at least one" as used herein.

All patents, patent applications, provisional applications, and publications referred to or cited herein are incorporated by reference in their entirety to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1—Method for Identifying Genes that Impart Resistance to 2,4-D in Planta As a way to identify genes which possess herbicide degrading activities in planta, it is possible to mine current public databases such as NCBI (National Center for Biotechnology Information). To begin the process, it is necessary to have a functional gene sequence already identified that encodes a protein with the desired characteristics (i.e., α-ketoglutarate dioxygenase activity). This protein sequence is then used as the input for the BLAST (Basic Local Alignment Search Tool) (Altschul et al., 1997) algorithm to compare against available NCBI protein sequences deposited. Using default settings, this search returns upwards of 100 homologous protein sequences at varying levels. These range from highly identical (85-98%) to very low identity (23-32%) at the amino acid level. Traditionally only sequences with high homology would be expected to retain similar properties to the input sequence. In this case, only sequences with ≤50% homology were chosen. As exemplified herein, cloning and recombinantly expressing homologues with as little as 31% amino acid conservation (relative to tfdA from *Ralstonia eutropha*) can be used to impart commercial levels of resistance not only to the intended herbicide, but also to substrates never previously tested with these enzymes.

A single gene (sdpA) was identified from the NCBI database (see the ncbi.nlm.nih.gov website; accession #AF516752) as a homologue with only 31% amino acid identity to tfdA. Percent identity was determined by first translating both the sdpA and tfdA DNA sequences deposited in the database to proteins, then using ClustalW in the VectorNTI software package to perform the multiple sequence alignment.

Example 2—Optimization of Sequence for Expression in Plants and Bacteria 2.1—Background.

To obtain higher levels of expression of heterologous genes in plants, it may be preferred to reengineer the protein encoding sequence of the genes so that they are more efficiently expressed in plant cells. Maize is one such plant where it may be preferred to re-design the heterologous protein coding region prior to transformation to increase the expression level of the gene and the level of encoded protein in the plant. Therefore, an additional step in the design of genes encoding a bacterial protein is reengineering of a heterologous gene for optimal expression.

One reason for the reengineering of a bacterial protein for expression in maize is due to the non-optimal G+C content of the native gene. For example, the very low G+C content of many native bacterial gene(s) (and consequent skewing towards high A+T content) results in the generation of sequences mimicking or duplicating plant gene control sequences that are known to be highly A+T rich. The presence of some A+T-rich sequences within the DNA of gene(s) introduced into plants (e.g., TATA box regions normally found in gene promoters) may result in aberrant transcription of the gene(s). On the other hand, the presence of other regulatory sequences residing in the transcribed mRNA (e.g., polyadenylation signal sequences (AAUAAA), or sequences complementary to small nuclear RNAs involved in pre-mRNA splicing) may lead to RNA instability. Therefore, one goal in the design of genes encoding a bacterial protein for maize expression, more preferably referred to as plant optimized gene(s), is to generate a DNA sequence having a higher G+C content, and preferably one close to that of maize genes coding for metabolic enzymes. Another goal in the design of the plant optimized gene(s) encoding a bacterial protein is to generate a DNA sequence in which the sequence modifications do not hinder translation.

Table 3 illustrates how high the G+C content is in maize. For the data in Table 3, coding regions of the genes were extracted from GenBank (Release 71) entries, and base compositions were calculated using the MacVector™ program (Accelerys, San Diego, Calif.). Intron sequences were ignored in the calculations.

TABLE 3

Compilation of G + C contents of protein coding regions of maize genes

| Protein Class[a] | Range % G + C | Mean % G + C[b] |
|---|---|---|
| Metabolic Enzymes (76) | 44.4-75.3 | 59.0 (.+−.8.0) |
| Structural Proteins (18) | 48.6-70.5 | 63.6 (.+−.6.7) |
| Regulatory Proteins (5) | 57.2-68.8 | 62.0 (.+−.4.9) |

TABLE 3-continued

Compilation of G + C contents of protein coding regions of maize genes

| Protein Class[a] | Range % G + C | Mean % G + C[b] |
|---|---|---|
| Uncharacterized Proteins (9) | 41.5-70.3 | 64.3 (.+−.7.2) |
| All Proteins (108) | 44.4-75.3 | 60.8 (.+−.5.2)[c] |

[a]Number of genes in class given in parentheses.
[b]Standard deviations given in parentheses.
[c]Combined groups mean ignored in mean calculation Due to the plasticity afforded by the redundancy/degeneracy of the genetic code (i.e., some amino acids are specified by more than one codon), evolution of the genomes in different organisms or classes of organisms has resulted in differential usage of redundant codons. This "codon bias" is reflected in the mean base composition of protein coding regions. For example, organisms with relatively low G+C contents utilize codons having A or T in the third position of redundant codons, whereas those having higher G+C contents utilize codons having G or C in the third position. It is thought that the presence of "minor" codons within an mRNA may reduce the absolute translation rate of that mRNA, especially when the relative abundance of the charged tRNA corresponding to the minor codon is low. An extension of this is that the diminution of translation rate by individual minor codons would be at least additive for multiple minor codons. Therefore, mRNAs having high relative contents of minor codons would have correspondingly low translation rates. This rate would be reflected by subsequent low levels of the encoded protein.

In engineering genes encoding a bacterial protein for maize (or other plant, such as cotton or soybean) expression, the codon bias of the plant has been determined. The codon bias for maize is the statistical codon distribution that the plant uses for coding its proteins and the preferred codon usage is shown in Table 4. After determining the bias, the percent frequency of the codons in the gene(s) of interest is determined. The primary codons preferred by the plant should be determined, as well as the second, third, and fourth choices of preferred codons when multiple choices exist. A new DNA sequence can then be designed which encodes the amino sequence of the bacterial protein, but the new DNA sequence differs from the native bacterial DNA sequence (encoding the protein) by the substitution of the plant (first preferred, second preferred, third preferred, or fourth preferred) codons to specify the amino acid at each position within the protein amino acid sequence. The new sequence is then analyzed for restriction enzyme sites that might have been created by the modification. The identified sites are further modified by replacing the codons with first, second, third, or fourth choice preferred codons. Other sites in the sequence which could affect transcription or translation of the gene of interest are the exon:intron junctions (5' or 3'), poly A addition signals, or RNA polymerase termination signals. The sequence is further analyzed and modified to reduce the frequency of TA or GC doublets. In addition to the doublets, G or C sequence blocks that have more than about four residues that are the same can affect transcription of the sequence. Therefore, these blocks are also modified by replacing the codons of first or second choice, etc. with the next preferred codon of choice.

TABLE 4

Preferred amino acid codons for proteins expressed in maize

| Amino Acid | Codon* |
|---|---|
| Alanine | GCC/GCG |
| Cysteine | TGC/TGT |
| Aspartic Acid | GAC/GAT |
| Glutamic Acid | GAG/GAA |
| Phenylalanine | TTC/TTT |
| Glycine | GGC/GGG |
| Histidine | CAC/CAT |
| Isoleucine | ATC/ATT |
| Lysine | AAG/AAA |
| Leucine | CTG/CTC |
| Methionine | ATG |
| Asparagine | AAC/AAT |
| Proline | CCG/CCA |
| Glutamine | CAG/CAA |
| Arginine | AGG/CGC |
| Serine | AGC/TCC |
| Threonine | ACC/ACG |
| Valine | GTG/GTC |
| Tryptophan | TGG |
| Tryrosine | TAC/TAT |
| Stop | TGA/TAG |

It is preferred that the plant optimized gene(s) encoding a bacterial protein contain about 63% of first choice codons, between about 22% to about 37% second choice codons, and between about 15% to about 0% third or fourth choice codons, wherein the total percentage is 100%. Most preferred the plant optimized gene(s) contains about 63% of first choice codons, at least about 22% second choice codons, about 7.5% third choice codons, and about 7.5% fourth choice codons, wherein the total percentage is 100%. The method described above enables one skilled in the art to modify gene(s) that are foreign to a particular plant so that the genes are optimally expressed in plants. The method is further illustrated in PCT application WO 97/13402.

Thus, in order to design plant optimized genes encoding a bacterial protein, a DNA sequence is designed to encode the amino acid sequence of said protein utilizing a redundant genetic code established from a codon bias table compiled from the gene sequences for the particular plant or plants. The resulting DNA sequence has a higher degree of codon diversity, a desirable base composition, can contain strategically placed restriction enzyme recognition sites, and lacks sequences that might interfere with transcription of the gene, or translation of the product mRNA. Thus, synthetic genes that are functionally equivalent to the proteins/genes of the subject invention can be used to transform hosts, including plants. Additional guidance regarding the production of synthetic genes can be found in, for example, U.S. Pat. No. 5,380,831.

2.2—AAD-12 Plant Rebuild Analysis.

Extensive analysis of the 876 base pairs (bp) of the DNA sequence of the native AAD-12 coding region (SEQ ID NO:1) revealed the presence of several sequence motifs that are thought to be detrimental to optimal plant expression, as well as a non-optimal codon composition. The protein encoded by SEQ ID NO:1 (AAD-12) is presented as SEQ ID NO:2. To improve production of the recombinant protein in monocots as well as dicots, a "plant-optimized" DNA sequence AAD-12 (v1) (SEQ ID NO:3) was developed that encodes a protein (SEQ ID NO:4) which is the same as the native SEQ ID NO:2 except for the addition of an alanine residue at the second position (underlined in SEQ ID NO:4). The additional alanine codon (GCT; underlined in SEQ ID NO:3) encodes part of an NcoI restriction enzyme recognition site (CCATGG) spanning the ATG translational start codon. Thus, it serves the dual purpose of facilitating subsequent cloning operations while improving the sequence context surrounding the ATG start codon to optimize translation initiation. The proteins encoded by the native and plant-optimized (v1) coding regions are 99.3% identical, differing only at amino acid number 2. In contrast, the native and plant-optimized (v1) DNA sequences of the coding regions are only 79.7% identical. Table 5 shows the differences in codon compositions of the native (Columns A and D) and plant-optimized sequences (Columns B and E), and allows comparison to a theoretical plant-optimized sequence (Columns C and F).

TABLE 5

Codon composition comparisons of coding regions of Native AAD-12, Plant-Optimized version (v1) and a Theoretical Plant-Optimized version.

| Amino Acid | Codon | A<br>Native<br># | B<br>Plant Opt<br>v1 # | C<br>Theor. Plant<br>Opt. # |
|---|---|---|---|---|
| ALA (A) | GCA | 1 | 10 | 11 |
|  | GCC | 35 | 16 | 15 |
|  | GCG | 7 | 0 | 0 |
|  | GCT | 0 | 18 | 17 |
| ARG (R) | AGA | 0 | 4 | 5 |
|  | AGG | 0 | 4 | 6 |
|  | CGA | 0 | 0 | 0 |
|  | CGC | 15 | 6 | 4 |
|  | CGG | 3 | 0 | 0 |
|  | CGT | 0 | 4 | 3 |
| ASN (N) | AAC | 3 | 2 | 2 |
|  | AAT | 1 | 2 | 2 |
| ASP (D) | GAC | 15 | 9 | 9 |
|  | GAT | 2 | 8 | 8 |
| CYS (C) | TGC | 3 | 2 | 2 |
|  | TGT | 0 | 1 | 1 |
| END | TAA | 1 | 0 | 1 |
|  | TAG | 0 | 0 |  |
|  | TGA | 0 | 1 |  |
| GLN (Q) | CAA | 1 | 8 | 7 |
|  | CAG | 13 | 6 | 7 |
| GLU (E) | GAA | 3 | 4 | 4 |
|  | GAG | 8 | 7 | 7 |
| GLY (G) | GGA | 0 | 8 | 7 |
|  | GGC | 24 | 7 | 7 |
|  | GGG | 1 | 3 | 4 |
|  | GGT | 0 | 7 | 7 |
| HIS (H) | CAC | 8 | 9 | 9 |
|  | CAT | 8 | 7 | 7 |
| ILE (I) | ATA | 0 | 2 | 2 |
|  | ATC | 10 | 4 | 5 |
|  | ATT | 1 | 5 | 4 |
|  | Totals | 163 | 164 | 163 |
| Amino Acid | Codon | D<br>Native<br># | E<br>Plant Opt<br>v1 # | F<br>Theor. Plant<br>Opt. # |
| LEU (L) | CTA | 0 | 0 | 0 |
|  | CTC | 1 | 8 | 8 |
|  | CTG | 23 | 0 | 0 |
|  | CTT | 0 | 8 | 8 |
|  | TTA | 0 | 0 | 0 |
|  | TTG | 0 | 8 | 8 |

TABLE 5 -continued

Codon composition comparisons of coding regions of Native AAD-12, Plant-Optimized version (v1) and a Theoretical Plant-Optimized version.

| | | | | |
|---|---|---|---|---|
| LYS (K) | AAA | 1 | 1 | 2 |
| | AAG | 5 | 5 | 4 |
| MET (M) | ATG | 10 | 10 | 10 |
| PHE (F) | TTC | 7 | 5 | 5 |
| | TTT | 1 | 3 | 3 |
| PRO (P) | CCA | 0 | 5 | 6 |
| | CCC | 9 | 4 | 4 |
| | CCG | 5 | 0 | 0 |
| | CCT | 0 | 5 | 5 |
| SER (S) | AGC | 5 | 4 | 3 |
| | AGT | 0 | 0 | 0 |
| | TCA | 0 | 3 | 3 |
| | TCC | 2 | 3 | 3 |
| | TCG | 6 | 0 | 0 |
| | TCT | 0 | 3 | 3 |
| THR (T) | ACA | 1 | 4 | 5 |
| | ACC | 11 | 7 | 7 |
| | ACG | 5 | 0 | 0 |
| | ACT | 1 | 7 | 6 |
| TRP (W) | TGG | 8 | 8 | 8 |
| TYR (Y) | TAC | 4 | 3 | 3 |
| | TAT | 1 | 2 | 2 |
| VAL (V) | GTA | 0 | 0 | 0 |
| | GTC | 6 | 8 | 7 |
| | GTG | 18 | 8 | 9 |
| | GTT | 0 | 8 | 8 |
| | Totals | 130 | 130 | 130 |

It is clear from examination of Table 5 that the native and plant-optimized coding regions, while encoding nearly identical proteins, are substantially different from one another. The Plant-Optimized version (v1) closely mimics the codon composition of a theoretical plant-optimized coding region encoding the AAD-12 protein.

2.3 Rebuild for *E. coli* Expression

Specially engineered strains of *Escherichia coli* and associated vector systems are often used to produce relatively large amounts of proteins for biochemical and analytical studies. It is sometimes found that a native gene encoding the desired protein is not well suited for high level expression in *E. coli*, even though the source organism for the gene may be another bacterial genus. In such cases it is possible and desirable to reengineer the protein coding region of the gene to render it more suitable for expression in *E. coli*. *E. coli* Class II genes are defined as those that are highly and continuously expressed during the exponential growth phase of *E. coli* cells. (Henaut, A. and Danchin, A. (1996) in *Escherichia coli and Salmonella typhimurium cellular and molecular biology*, vol. 2, pp. 2047-2066. Neidhardt, F., Curtiss III, R., Ingraham, J., Lin. E., Low, B., Magasanik, B., Reznikoff, W., Riley, M., Schaechter, M. and Umbarger. H. (eds.) American Society for Microbiology, Washington, D.C.). Through examination of the codon compositions of the coding regions of *E. coli* Class II genes, one can devise an average codon composition for these *E. coli*-Class II gene coding regions. It is thought that a protein coding region having an average codon composition mimicking that of the Class II genes will be favored for expression during the exponential growth phase of *E. coli*. Using these guidelines, a new DNA sequence that encodes the AAD-12 protein (SEQ ID NO:4); including the additional alanine at the second position, as mentioned above), was designed according to the average codon composition of *E. coli* Class II gene coding regions. The initial sequence, whose design was based only on codon composition, was further engineered to include certain restriction enzyme recognition sequences suitable for cloning into *E. coli* expression vectors. Detrimental sequence features such as highly stable stemloop structures were avoided, as were intragenic sequences homologous to the 3' end of the 16S ribosomal RNA (i.e. Shine Dalgarno sequences) The *E. coli*-optimized sequence (v2) is disclosed as SEQ ID NO:5 and encodes the protein disclosed in SEQ ID NO:4.

The native and *E. coli*-optimized (v2) DNA sequences are 84.0% identical, while the plant-optimized (v1) and *E. coli*-optimized (v2) DNA sequences are 76.0% identical. Table 6 presents the codon compositions of the native AAD-12 coding region (Columns A and D), an AAD-12 coding region optimized for expression in *E. coli* (v2; Columns B and E) and the codon composition of a theoretical coding region for the AAD-12 protein having an optimal codon composition of *E. coli* Class II genes (Columns C and F).

TABLE 6

Codon composition comparisons of coding regions of Native AAD-12, E. coli-Optimized version (v2) and a Theoretical E. coli Class II-Optimized version.

| Amino Acid | Codon | A Native # | B E. coli Opt v2 # | C Theor. Class II # |
|---|---|---|---|---|
| ALA (A) | GCA | 1 | 13 | 13 |
|  | GCC | 35 | 0 | 0 |
|  | GCG | 7 | 18 | 17 |
|  | GCT | 0 | 13 | 14 |
| ARG (R) | AGA | 0 | 0 | 0 |
|  | AGG | 0 | 0 | 0 |
|  | CGA | 0 | 0 | 0 |
|  | CGC | 15 | 6 | 6 |
|  | CGG | 3 | 0 | 0 |
|  | CGT | 0 | 12 | 12 |
| ASN (N) | AAC | 3 | 4 | 4 |
|  | AAT | 1 | 0 | 0 |
| ASP (D) | GAC | 15 | 10 | 9 |
|  | GAT | 2 | 7 | 8 |
| CYS (C) | TGC | 3 | 2 | 2 |
|  | TGT | 0 | 1 | 1 |
| END | TAA | 1 | 1 | 1 |
|  | TAG | 0 | 0 | 0 |
|  | TGA | 0 | 0 | 0 |
| GLN (Q) | CAA | 1 | 3 | 3 |
|  | CAG | 13 | 11 | 11 |
| GLU (E) | GAA | 3 | 8 | 8 |
|  | GAG | 8 | 3 | 3 |
| GLY (G) | GGA | 0 | 0 | 0 |
|  | GGC | 24 | 12 | 11 |
|  | GGG | 1 | 0 | 0 |
|  | GGT | 0 | 13 | 14 |
| HIS (H) | CAC | 8 | 11 | 11 |
|  | CAT | 8 | 5 | 5 |
| ILE (I) | ATA | 0 | 0 | 0 |
|  | ATC | 10 | 7 | 7 |
|  | ATT | 1 | 4 | 4 |
|  | Totals | 163 | 164 | 164 |

| Amino Acid | Codon | D Native # | E E. coli Opt v2 # | F Theor, Class II # |
|---|---|---|---|---|
| LEU (L) | CTA | 0 | 0 | 0 |
|  | CTC | 1 | 2 | 0 |
|  | CTG | 23 | 20 | 24 |
|  | CTT | 0 | 1 | 0 |
|  | TTA | 0 | 1 | 0 |
|  | TTG | 0 | 0 | 0 |
| LYS (K) | AAA | 1 | 4 | 5 |
|  | AAG | 5 | 2 | 1 |
| MET (M) | ATG | 10 | 10 | 10 |
| PHE (F) | TTC | 7 | 6 | 6 |
|  | TTT | 1 | 2 | 2 |
| PRO (P) | CCA | 0 | 3 | 2 |
|  | CCC | 9 | 0 | 0 |
|  | CCG | 5 | 11 | 12 |
|  | CCT | 0 | 0 | 0 |
| SER (S) | AGC | 5 | 4 | 4 |
|  | AGT | 0 | 0 | 0 |
|  | TCA | 0 | 0 | 0 |

TABLE 6 -continued

Codon composition comparisons of coding regions of Native AAD-12, E. coli-Optimized version (v2) and a Theoretical E. coli Class II-Optimized version.

|         |     |     |     |     |
|---------|-----|-----|-----|-----|
|         | TCC | 2   | 5   | 4   |
|         | TCG | 6   | 0   | 0   |
|         | TCT | 0   | 4   | 5   |
| THR (T) | ACA | 1   | 0   | 0   |
|         | ACC | 11  | 12  | 12  |
|         | ACG | 5   | 0   | 0   |
|         | ACT | 1   | 6   | 6   |
| TRP (W) | TGG | 8   | 8   | 8   |
| TYR (Y) | TAC | 4   | 3   | 3   |
|         | TAT | 1   | 2   | 2   |
| VAL (V) | GTA | 0   | 6   | 6   |
|         | GTC | 6   | 0   | 0   |
|         | GTG | 18  | 8   | 7   |
|         | GTT | 0   | 10  | 11  |
|         | Totals | 130 | 130 | 130 |

It is clear from examination of Table 6 that the native and E. coli-optimized coding regions, while encoding nearly identical proteins, are substantially different from one another. The E. coli-Optimized version (v2) closely mimics the codon composition of a theoretical E. coli-optimized coding region encoding the AAD-12 protein.

2.4—Design of a Soybean-Codon-Biased DNA Sequence Encoding a Soybean EPSPS Having Mutations that Confer Glyphosate Tolerance.

This example teaches the design of a new DNA sequence that encodes a mutated soybean 5-enolpyruvoylshikimate 3-phosphate synthase (EPSPS), but is optimized for expression in soybean cells. The amino acid sequence of a triply-mutated soybean EPSPS is disclosed as SEQ ID NO:5 of WO 2004/009761. The mutated amino acids in the so-disclosed sequence are at residue 183 (threonine of native protein replaced with isoleucine), residue 186 (arginine in native protein replaced with lysine), and residue 187 (proline in native protein replaced with serine). Thus, one can deduce the amino acid sequence of the native soybean EPSPS protein by replacing the substituted amino acids of SEQ ID NO:5 of WO 2004/009761 with the native amino acids at the appropriate positions. Such native protein sequence is disclosed as SEQ ID NO:20 of PCT/US2005/014737 (filed May 2, 2005). A doubly mutated soybean EPSPS protein sequence, containing a mutation at residue 183 (threonine of native protein replaced with isoleucine), and at residue 187 (proline in native protein replaced with serine) is disclosed as SEQ ID NO:21 of PCT/US2005/014737.

A codon usage table for soybean (*Glycine max*) protein coding sequences, calculated from 362,096 codons (approximately 870 coding sequences), was obtained from the "kazusa.or.jp/codon" World Wide Web site. Those data were reformatted as displayed in Table 7. Columns D and H of Table 7 present the distributions (in % of usage for all codons for that amino acid) of synonymous codons for each amino acid, as found in the protein coding regions of soybean genes. It is evident that some synonymous codons for some amino acids (an amino acid may be specified by 1, 2, 3, 4, or 6 codons) are present relatively rarely in soybean protein coding regions (for example, compare usage of GCG and GCT codons to specify alanine). A biased soybean codon usage table was calculated from the data in Table 7. Codons found in soybean genes less than about 10% of total occurrences for the particular amino acid were ignored. To balance the distribution of the remaining codon choices for an amino acid, a weighted average representation for each codon was calculated, using the formula:

Weighted % of $C1 = 1/(\% \ C1 + \% \ C2 + \% \ C3 + \text{etc.}) \times \% \ C1 \times 100$ where C1 is the codon in question, C2, C3, etc. represent the remaining synonymous codons, and the % values for the relevant codons are taken from columns D and H of Table 7 (ignoring the rare codon values in bold font). The Weighted % value for each codon is given in Columns C and G of Table 7. TGA was arbitrarily chosen as the translation terminator. The biased codon usage frequencies were then entered into a specialized genetic code table for use by the OptGene™ gene design program (Ocimum Biosolutions LLC, Indianapolis, Ind.).

TABLE 7

Synonymous codon representation in soybean protein coding sequences, and calculation of a biased codon representation set for soybean-optimized synthetic gene design.

| A<br>Amino Acid | B<br>Codon | C<br>Weighted % | D<br>Soybean % |
|---|---|---|---|
| ALA (A) | GCA | 33.1 | 30.3 |
|  | GCC | 24.5 | 22.5 |
|  | GCG | DNU* | 8.5 |
|  | GCT | 42.3 | 38.7 |

TABLE 7 -continued

Synonymous codon representation in soybean protein coding sequences, and calculation of a biased codon representation set for soybean-optimized synthetic gene design.

| Amino Acid | Codon | Weighted % | Soybean % |
|---|---|---|---|
| ARG (R) | AGA | 36.0 | 30.9 |
|  | AGG | 32.2 | 27.6 |
|  | CGA | DNU | 8.2 |
|  | CGC | 14.8 | 12.7 |
|  | CGG | DNU | 6.0 |
|  | CGT | 16.9 | 14.5 |
| ASN (N) | AAC | 50.0 | 50.0 |
|  | AAT | 50.0 | 50.0 |
| ASP (D) | GAC | 38.1 | 38.1 |
|  | GAT | 61.9 | 61.9 |
| CYS (C) | TGC | 50.0 | 50.0 |
|  | TGT | 50.0 | 50.0 |
| END | TAA | DNU | 40.7 |
|  | TAG | DNU | 22.7 |
|  | TGA | 100.0 | 36.6 |
| GLN (Q) | CAA | 55.5 | 55.5 |
|  | CAG | 44.5 | 44.5 |
| GLU (E) | GAA | 50.5 | 50.5 |
|  | GAG | 49.5 | 49.5 |
| GLY (G) | GGA | 31.9 | 31.9 |
|  | GGC | 19.3 | 19.3 |
|  | GGG | 18.4 | 18.4 |
|  | GGT | 30.4 | 30.4 |
| HIS (H) | CAC | 44.8 | 44.8 |
|  | CAT | 55.2 | 55.2 |
| ILE (I) | ATA | 23.4 | 23.4 |
|  | ATC | 29.9 | 29.9 |
|  | ATT | 46.7 | 46.7 |
| LEU (L) | CTA | DNU | 9.1 |
|  | CTC | 22.4 | 18.1 |
|  | CTG | 16.3 | 13.2 |
|  | CTT | 31.5 | 25.5 |
|  | TTA | DNU | 9.8 |
|  | TTG | 29.9 | 24.2 |
| LYS (K) | AAA | 42.5 | 42.5 |
|  | AAG | 57.5 | 57.5 |
| MET (M) | ATG | 100.0 | 100 |
| PHE (F) | TTC | 49.2 | 49.2 |
|  | TTT | 50.8 | 50.8 |
| PRO (P) | CCA | 39.8 | 36.5 |
|  | CCC | 20.9 | 19.2 |
|  | CCG | DNU | 8.3 |
|  | CCT | 39.3 | 36.0 |
| SER (S) | AGC | 16.0 | 15.1 |
|  | AGT | 18.2 | 17.1 |
|  | TCA | 21.9 | 20.6 |
|  | TCC | 18.0 | 16.9 |
|  | TCG | DNU | 6.1 |
|  | TCT | 25.8 | 24.2 |
| THR (T) | ACA | 32.4 | 29.7 |
|  | ACC | 30.2 | 27.7 |
|  | ACG | DNU | 8.3 |
|  | ACT | 37.4 | 34.3 |
| TRP (W) | TGG | 100.0 | 100 |

TABLE 7 -continued

Synonymous codon representation in soybean protein coding sequences, and calculation of a biased codon representation set for soybean-optimized synthetic gene design.

| | | | |
|---|---|---|---|
| TYR (Y) | TAC | 48.2 | 48.2 |
| | TAT | 51.8 | 51.8 |
| VAL (V) | GTA | 11.5 | 11.5 |
| | GTC | 17.8 | 17.8 |
| | GTG | 32.0 | 32.0 |
| | GTT | 38.7 | 38.7 |

*DNU = Do Not Use

To derive a soybean-optimized DNA sequence encoding the doubly mutated EPSPS protein, the protein sequence of SEQ ID NO:21 from PCT/US2005/014737 was reverse-translated by the OptGene™ program using the soybean-biased genetic code derived above. The initial DNA sequence thus derived was then modified by compensating codon changes (while retaining overall weighted average representation for the codons) to reduce the numbers of CG and TA doublets between adjacent codons, increase the numbers of CT and TG doublets between adjacent codons, remove highly stable intrastrand secondary structures, remove or add restriction enzyme recognition sites, and to remove other sequences that might be detrimental to expression or cloning manipulations of the engineered gene. Further refinements of the sequence were made to eliminate potential plant intron splice sites, long runs of A/T or C/G residues, and other motifs that might interfere with RNA stability, transcription, or translation of the coding region in plant cells. Other changes were made to eliminate long internal Open Reading Frames (frames other than +1). These changes were all made within the constraints of retaining the soybean-biased codon composition as described above, and while preserving the amino acid sequence disclosed as SEQ ID NO:21 of PCT/US2005/014737.

The soybean-biased DNA sequence that encodes the EPSPS protein of SEQ ID NO:21 is disclosed as bases 1-1575 of SEQ ID NO:22 of PCT/US2005/014737. Synthesis of a DNA fragment comprising SEQ ID NO:22 of PCT/US2005/014737 was performed by a commercial supplier (PicoScript, Houston Tex.).

Example 3—Cloning of Expression and Transformation Vectors 3.1 Construction of *E. coli.* pET Expression Vector.

Using the restriction enzymes corresponding to the sites added with the additional cloning linkers (Xba 1, Xho 1) AAD-12 (v2) was cut out of the picoscript vector, and ligated into a pET280 streptomycin/spectinomycin resistant vector. Ligated products were then transformed into TOP 10F' *E. coli*, and plated on to Luria Broth+50 µg/ml Streptomycin & Spectinomycin (LB S/S) agar plates.

To differentiate between AAD-12 (v2): pET280 and pCR2.1: pET280 ligations, approximately 20 isolated colonies were picked into 6 ml of LB-S/S, and grown at 37° C. for 4 hours with agitation. Each culture was then spotted onto LB+Kanamycin 50 µg/ml plates, which were incubated at 37° C. overnight. Colonies that grew on the LB-K were assumed to have the pCR2.1 vector ligated in, and were discarded. Plasmids were isolated from the remaining cultures as before, and checked for correctness with digestion by XbaI/XhoI. The final expression construct was given the designation pDAB3222.

3.2—Construction of *Pseudomonas* Expression Vector

The AAD-12 (v2) open reading frame was initially cloned into the modified pET expression vector (Novagen), "pET280 S/S", as an XbaI-XhoI fragment. The resulting plasmid pDAB725 was confirmed with restriction enzyme digestion and sequencing reactions. The AAD-12 (v2) open reading frame from pDAB725 was transferred into the *Pseudomonas* expression vector, pMYC1803, as an XbaI-XhoI fragment. Positive colonies were confirmed via restriction enzyme digestion. The completed construct pDAB739 was transformed into the MB217 and MB324 *Pseudomonas* expression strains.

3.3—Completion of Binary Vectors.

The plant optimized gene AAD-12 (v1) was received from Picoscript (the gene rebuild design was completed (see above) and out-sourced to Picoscript for construction) and sequence verified (SEQ ID NO:3) internally, to confirm that no alterations of the expected sequence were present. The sequencing reactions were carried out with M13 Forward (SEQ ID NO:6) and M13 Reverse (SEQ ID NO:7) primers using the Beckman Coulter "Dye Terminator Cycle Sequencing with Quick Start Kit" reagents as before. Sequence data was analyzed and results indicated that no anomalies were present in the plant optimized AAD-12 (v1) DNA sequence. The AAD-12 (v1) gene was cloned into pDAB726 as an Nco I-Sac I fragment. The resulting construct was designated pDAB723, containing: [AtUbi10 promoter: Nt OSM 5'UTR: AAD-12 (v1): Nt OSM3'UTR: ORF1 polyA 3'UTR] (verified with a PvuII and a Not I restriction digests). A Not I-Not I fragment containing the described cassette was then cloned into the Not I site of the binary vector pDAB3038. The resulting binary vector, pDAB724, containing the following cassette [AtUbi10 promoter Nt OSM5'UTR: AAD-12 (v1): Nt OSM 3'UTR: ORF1 polyA 3'UTR: CsVMV promoter PAT: ORF25/26 3'UTR] was restriction digested (with Bam HI, Nco I, Not I, SacI, and Xmn I) for verification of the correct orientation. The verified completed construct (pDAB724) was used for transformation into *Agrobacterium* (see section 7.2).

3.4—Cloning of Additional Transformation Constructs.

All other constructs created for transformation into appropriate plant species were built using similar procedures as previously described herein, and other standard molecular cloning methods (Maniatis et al., 1982). Table 8 lists all the transformation constructs used with appropriate promoters and features defined, as well as the crop transformed.

TABLE 8

Binary constructs used in transformation of various plant species.

| pDAB # | pDAS # | Species Transformed into | Gene of interest (GOI) | Promoter | Feature 1 | Feature 2 | GOI 2 | Promoter | Bacterial Selection gene | Bacterial Selection gene 2 | Plant Selection gene | Promoter | Trxn Method |
|---|---|---|---|---|---|---|---|---|---|---|---|---|---|
| 724 | — | A, Ct, S | AAD12 v1 | AtUbi10 | NtOsm | — | — | — | Erythromycin | — | pat | CsVMV | Agro binary |
| 3274 | — | A | AAD12 v1 | AtUbi10 | NtOsm | RB7 Mar v2 | — | — | Spectinomycin | — | — | — | Agro binary |
| 3278 | 1580 | T | AAD12 v1 | CsVMV | NtOsm | RB7 Mar v2 | — | — | Spectinomycin | — | pat | AtUbi10 | Agro binary |
| 3285 | — | A | AAD12 v1 | CsVMV | NtOsm | RB7 Mar v2 | — | — | Spectinomycin | — | pat | AtUbi10 | Agro binary |
| 3759 | — | A, Ca, S | AAD12 v1 | CsVMV | NtOsm | RB7 Mar v2 | EPSPS | AtUbi10 | Spectinomycin | — | pat | AtUbi10 | Agro binary |
| 4101 | 1863 | Cn, R | AAD12 v1 | ZmUbi1 | — | RB7 Mar v2 | — | — | Ampicillin | — | AHAS v3 | OsAct1 | Whiskers/Gun |
| 4464 | — | S | AAD12 v1 | CsVMV | — | RB7 Mar v2 | — | — | Spectinomycin | — | pat | CsVMV | Agro binary |
| 4468 | — | S | AAD12 v1 | AtUbi10 | — | RB7 Mar v2 | — | — | Spectinomycin | — | pat | CsVMV | Agro binary |
| 4472 | — | S | AAD12 v1 | AtUbi3 | — | RB7 Mar v2 | — | — | Spectinomycin | — | pat | CsVMV | Agro binary |
| 4476 | — | S | AAD12 v1 | ZmUbi1 | — | RB7 Mar v2 | — | — | Spectinomycin | — | pat | CsVMV | Agro binary |
| 4480 | — | S | AAD12 v1 | AtAct2 | — | RB7 Mar v2 | — | — | Spectinomycin | — | pat | CsVMV | Agro binary |

\* A = *Arabidopsis* CsVMV = Cassava Vein Mosaic Virus Promoter ZmUbi1 = *Zea mays* Ubiquitin 1 Promoter T = Tobacco AtUbi10 = *Arabidopsis thaliana* Ubiquitin 10 Promoter HptII = hygromycin phosphotransferase S = Soybean Atubi3 = *Arabidopsis thaliana* Ubiquitin 3 Promoter Ct = Cotton AtAct2 = *Arabidopsis thaliana* Actin 2 Promoter R = Rice RB7 Mar v2 = *Nicotiana tabacum* matrix associated region (MAR) Cn = Corn Nt Osm = *Nicotiana tabacum* Osmotin 5' Untranslated Reaion and the *Nicotiana tabacum* Osmotin 3' Untranslated Region Ca = Canola Example 4—Recombinant AAD-12 (v2' Expression and Purification in *Pseudomonas fluorescens*

4.1—*Pseudomonas fluorescens* Fermentation

For shake flask experiment, 200 µl of *Pseudomonas fluorescens* strain MB324 glycerol stock carried AAD-12 (v2) construct pDAB739 (sec 3.2) was used to inoculate 50 ml fresh LB media supplemented with 30 µg/ml tetracycline/HCl. The culture (in a 250 ml baffled Erlenmeyer flask) was incubated on a shaker (New Brunswick Scientific Model Innova 44) at 300 rpm and 30° C. for 16 hrs. 20 ml of seed culture was transferred into 1 L *Pseudomonas fluorescens* culture media (Yeast extract, 5 g/L; $K_2HPO_4$, 5 g/L; $(NH_4)_2PO_4$, 7.5 g/L; $(NH_4)_2SO_4$; $MgSO_4$-$7H_2O$, 1 g/L; KCl, 0.5 g/L; $CaCl_2$-$2H_2O$, 0.5 g/L; NaCitrate-$2H_2O$, 15 g/L; Glycerol, 95 g/L; Trace element solution, 10 ml/L; Trace element solution: $FeCl_3$-$6H_2O$, 5.4 g/L; $MnCl_2$-$4H_2O$, 1 g/L; $ZnSO_4$-$7H_2O$, 1.45 g/L; $CuSO_4$-$5H_2O$, 0.25 g/L; $H_3BO_3$, 0.1 g/L; $(NH_4)_6MO_7O_{24}$, 0.1 g/L; concentrated HCl, 13 ml/L) supplemented with 20 µg/ml tetracycline/HCl and 250 µl of Pluronic L61(anti-foam) in a 2.8 L baffled Erlenmeyer flask. The cultures were incubated at 30° C. and 300 rpm for 24 hrs. Isopropyl β-D-1-thiogalacto-pyranoside (IPTG) was added to 1 mM final in the cultures and continued to incubate for approximately 48 hrs at 25° C. Cells were harvested by centrifugation at 7 krpm at 4° C. for 15 min, and cell paste was stored at −80° C. or immediately processed for purification.

For tank experiments, 1 ml each of the glycerol stock was inoculated a 1 L baffled flask containing 200 ml of LB media supplemented with 30 µg/ml tetracycline/HCl at 300 rpm and 32° C. for 16-24 hrs. The combined culture from three flasks (600 ml) was then aseptically transferred to a 20 L fermentor (B. Braun Bioreactor Systems) containing 10 L of Dow proprietary defined medium (through Teknova, Hollister, Calif.) designed to support high cell density growth. Growth temperature was maintained at 32° C. and the pH was controlled at the desired set-point through the addition of aqueous ammonia. Dissolved oxygen was maintained at a positive level in the liquid culture by regulating the sparged air flow and the agitation rates. The fed-batch fermentation process was carried out for approximately 24 hrs till cell density reached 170-200 $OD_{575}$. IPTG was added to 1 mM to induce the recombinant protein expression and the temperature was reduced and maintained to 25° C. using circulation of cold-water supply. The induction phase of the fermentation was allowed to continue for another 24 hrs. Samples (30 ml) were collected for various analyses to determine cell density and protein expression level at 6, 12, and 18 hrs post-induction time points. At the end of a fermentation run, cells were harvested by centrifugation at 10 krpm for 30 min. The cell pellets were frozen at −80° C. for further processing.

4.2—Purification of AAD-12 (v2) for Biochemical Characterization and Antibody Production Approximately 100-200 g of frozen (or fresh) *Pseudomonas* cells were thawed and resuspended in 1-2 L of extraction buffer containing 20 mM Tris-HCl, pH 8.5, and 25 ml of Protease inhibitor cocktail (Sigma cat#P8465). The cells were disrupted using Microfluidizer (model M110L or 110Y) (Microfluidics, Newton, Mass.) on ice with one pass at 11,000-12,000 psi. The lysate was centrifuged at 24,000 rpm for 20 min. The supernatant was transferred and dialyzed against 10 volumes of 20 mM Tris-HCl, pH 8.5 overnight at 4° C., or diafiltrated with this buffer and filtered through a 0.45 µm membrane before applying to the column separations. All subsequent protein separations were performed using Pharmacia AKTA Explorer 100 and operated at 4° C. Prior to loading, a Q Sepharose Fast Flow column (Pharmacia XK 50/00, 500 ml bed size) was equilibrated with 20 mM Tris-HCl, pH 8.5 buffer. The sample was applied to the column at 15 ml/min and then washed with this buffer until the eluate $OD_{280}$ returned to baseline. Proteins were eluted with 2 L of linear gradient from 0 to 0.3 M NaCl at a flow rate of 15 ml/min, while 45 ml fractions were collected. Fractions containing AAD-12 activity as determined by the colorimetric enzyme assay and also corresponding to the predicted molecular weight of AAD-12 protein (about 32 kDa band on SDS-PAGE) were pooled. Solid ammonium sulfate to final 0.5 M was added to the sample, and then applied to a Phenyl HP column (Pharmacia XK 50/20, 250 ml bed size) equilibrated in 0.5 M ammonium sulfate in 20 mM Tris-HCl, pH 8.0. This column was washed with the binding buffer at 10 ml/min until the $OD_{280}$ of the eluate returned to baseline, proteins were eluted within 2 column volumes at 10 ml/min by a linear gradient from 0.5 M to 0 Ammonium sulfate in 20 mM Tris-HCl, pH 8.0, and 12.5 ml fractions were collected. The main peak fractions containing AAD-12 were pooled, and if necessary, concentrated using a MWCO 10 kDa cut-off membrane centrifugal filter device (Millipore). In some cases the sample was further applied to a Superdex 75 gel filtration column (Pharmacia XK 16/60, 110 ml bed size) with PBS buffer at a flow rate of 1 ml/min. Peak fractions containing pure AAD-12 were pooled and stored at −80° C. In most cases, AAD-12 protein purity is approaching or above 99% after sequential ion-exchange column and hydrophobic interaction column two-step separation. A typical yield for purified AAD-12 is 12-18 mg/g of wet cells. Bulk protein sample was formulated in 20 mM Tris-HCl, pH 8.0, 0.1 M NaCl, 2 mM DTT, and 1% Trehalose by diafiltration, and lyophilized on the Virtis Freezemobile Model 25EL (Virtis, Cardiner, N.Y.) for long-term storage.

Protein concentration was initially measured by Bradford assay using Bio-Rad Protein assay kit (cat#500-0006) with bovine serum albumin as standard. When needed, more accurate protein concentration was determined by using total amino acid hydrolysis. The sample was analyzed in Agilent 1100 HPLC system (Agilent Technologies, Santa Clara, Calif.) with amino acid calibration standards (cat#PN5061-3330) purchased from Agilent.

AAD-12 activity was determined through out the processes to ensure no loss of the enzyme activity by each treatment and manipulation, as described in the Example 5 below. Protein purity was monitored by using SDS-PAGE and analytical size exclusion chromatography. Purified protein sample was further verified and confirmed by N-terminal amino acid sequencing, and shown consisting of expected AQTTLQITPT residues at its N-terminus. Short and long-term protein stability was tested by enzymatic activity and by native-PAGE and SDS-PAGE gel analysis under both non-reducing and reducing conditions. And it was noticed that AAD-12 is prone to oligomerization via disulfide bond formation, therefore typically 2 mM DTT was used for protein storage. Phosphate-buffer saline (PBS) and Tris-buffer saline (TBS) were tested for protein lyophilization, with and without the presence of 1% trehalose. Additionally, the endotoxin and DNA contaminant context from purified sample were measured respectively, and the integrity of the AAD-12 protein was also assessed by isoelectric focusing (IEF) analysis.

Ten milligrams of purified AAD-12 (v2) was delivered to Zymed Laboratories, Inc. (South San Francisco, Calif.) for rabbit polyclonal antibody production. The rabbit received 5 injections in the period of 5 weeks with each injection containing 0.5 mg of the purified protein suspended in 1 ml of complete Freund's Adjuvant. Sera were tested in both ELISA and Western blotting experiments to confirm specificity and affinity before affinity purification, and horseradish peroxidase (HRP) conjugation (Zymed Lab Inc).

Example 5—In Vitro Assays of AAD-12 Activity 5.1—Assay Via Colorimetric Phenol Detection.

Enzyme activity was measured by colorimetric detection of the product phenol using a protocol modified from that of Fukumori and Hausinger (1993) (*J. Biol. Chem.* 268: 24311-24317) to enable deployment in a 96-well microplate format. The colorimetric assay has been described for use in measuring the activity of dioxygenases cleaving 2,4-D and dichlorprop to release the product 2,4-dichlorophenol. The color yield from several phenols was compared to that of 2,4-dichlorophenol using the detection method previously described to ascertain which phenol products could be readily detected. Phenols and phenol analogs were tested at a final concentration of 100 µM in 0.15 ml 20 mM MOPS pH 6.75 containing 200 µM $NH_4(FeSO_4)_2$, 200 µM sodium ascorbate. Pyridinols derived from fluroxypyr and triclopyr produced no significant color. The color yield of 2,4-dichlorophenol was linear and proportional to the concentration of phenol in the assay up to ~500 µM. A calibration curve performed under standard assay conditions (160 µl final assay volume) indicated that an absorbance at 510 nm of 0.1 was obtained from 17.2 µM phenol.

Enzyme assays were performed in a total volume of 0.16 ml 20 mM MOPS pH 6.75 containing 200 µM $NH_4FeSO_4$, 200 µM sodium ascorbate, 1 mM α-ketoglutarate, the appropriate substrate (added from a 100 mM stock made up in DMSO), and enzyme. Assays were initiated by addition of the aryloxyalkanoate substrate, enzyme or α-ketoglutarate at time zero. After 5 minutes of incubation at 25° C., the reaction was terminated by addition of 30 µl of a 1:1:1 mix of 50 mM Na EDTA; pH 10 buffer (3.09 g boric acid+3.73 g KCl+44 ml 1 N KOH) and 0.2% 4-aminoantipyrine. Then 10 µl 0.8% potassium ferricyanide was added and after 5 or 10 min, the absorbance at 510 nm was recorded in a spectrophotometric microplate reader. Blanks contained all reagents except for enzyme to account for the occasional slight contamination of some of the substrates by small amounts of phenols.

5.2—Assay Via Detection of Chloropyridinol

AAD-12 action on potential substrates such as the herbicide triclopyr containing a substituted pyridine (rather than benzene rings) will release a pyridinol on cleavage of the aryloxyalkanoate bond. Pyridinols were not detected using the aminoantipyrine/ferricyanide phenol detection described in the preceding section. However, it was found that product chloropyridinols absorb strongly in the near UV with $\lambda_{max}$ of 325 nm at pH 7 (extinction coefficient ~8,400 $M^{-1} \cdot cm^{-1}$). This was used to create a continuous microplate-based spectrophotometric assay. Assays were performed in a total volume of 0.2 ml 20 mM MOPS pH 6.75 containing 200 µM NH₄FeSO₄, 200 µM sodium ascorbate, 1 mM α-ketoglutarate, the appropriate substrate (added from a 100 mM stock made up in DMSO), and enzyme. Assays were initiated by addition of the aryloxyalkanoate substrate, enzyme or α-ketoglutarate at time zero and the increase in absorbance followed for 10 minutes at 325 nm in a microplate reader. The first 2 minutes of the reaction was used to determine initial rates. A calibration curve performed under standard assay conditions (200 µl final assay volume) indicated that an absorbance at 510 nm of 0.1 was obtained from 11.9 µM chloropyridinol.

5.3—Colorimetric Assay Using 2-(2-chloro,4-nitrophenoxy)propionate

A convenient assay of AAD-12 was devised using 2-(2-chloro,4-nitrophenoxy)propionate (CNPP) as substrate. Cleavage of CNPP by AAD-12 releases 2-chloro,4-nitrophenol. This phenol has a bright yellow absorbance at 410 nm at pH 7 enabling the reaction to be followed continuously or by endpoint analysis. The presence of AAD-12 activity can be monitored visually without the need for addition of further reagents. Microplate-based spectrophotometric assays were performed in a total volume of 0.2 ml 20 mM MOPS pH 6.75 containing 200 µM NH₄FeSO₄, 200 µM sodium ascorbate, 1 mM α-ketoglutarate, the appropriate amount of CNPP (added from a 10 mM stock made up in DMSO), and enzyme. Assays were initiated by addition of CNPP, enzyme, or α-ketoglutarate at time zero and the increase in absorbance followed for 10 min at 410 nm in a microplate reader. The first 2 min of the reaction was used to determine initial rates. A calibration curve performed under standard assay conditions (200 µl final assay volume) indicated that an absorbance at 410 nm of 0.1 was obtained from 25.1 µM 2-chloro, 4-nitrophenol. Using this assay, the kinetic constants for CNPP as a substrate were determined to be $K_m=31\pm5.5$ µM and $k=16.2\pm0.79$ min$^{-1}$.

Figure 3:
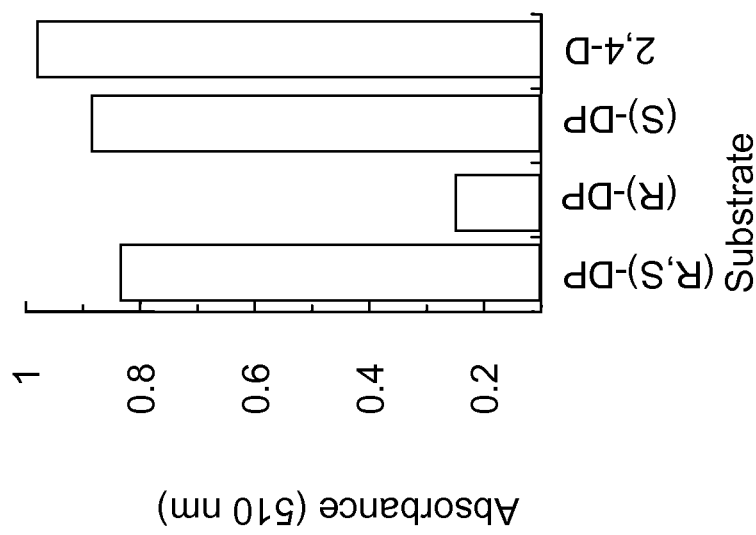
FIG. 3 illustrates activity of AAD-12 (v2) on 2,4-D and enantiomers of dichlorprop.

Example 6—In Vitro Activity of AAD-12 on Various Substrates 6.1—AAD-12 (v2) activity on (R,S)-dichlorprop, (R)-dichlorprop, (S)-dichlorprop and 2,4-D Using the phenol detection assay described in Example 5.1, four phenoxyalkanoates were assayed in a reaction mix containing 4.4 µg purified AAD-12 (v2). (R,S)-dichlorprop (R,S-DP) was tested at 1 mM and (R)-dichlorprop, (S)-dichlorprop and 2,4-D were tested at 0.5 mM. The results are shown in FIG. 3, which illustrates activity of AAD-12 (v2) on 2,4-D and enantiomers of dichlorprop. 4.4 µg AAD-12 (v2) was incubated with 0.5 mM substrate (1 mM for (R,S)-dichlorprop) and the reaction initiated by addition of α-ketoglutarate. After 5 minutes, the reaction was quenched, and the absorbance at 510 nm determined after addition of colorimetric detection reagents. The background value without enzyme was subtracted.

AAD-12 (v2) has excellent activity on (R,S)-dichlorprop and (S)-dichlorprop and has minimal activity on (R)-dichlorprop. This indicates that AAD-12 (v2) has a clear (S)-enantiomeric preference. The activity of AAD-12 (v2) on 2,4-D was equivalent to that on (S)-dichlorprop indicating that the enzyme can process oxypropionate and oxyacetates effectively.

6.2—AAD-12 (v2) Activity on Pyridyloxyalkanoates

Using the pyridinol assay described in Example 5.2, five pyridyloxyalkanoates were assayed at 1 mM in a reaction mix containing 6.8 µg purified AAD-12 (v2). The rates of each reaction were monitored and are presented in Table 9.

All five pyridyloxyalkanoates were cleaved to release pyridinols by AAD-12 (v2). The rates for the oxypropionate substrates 116844 and 91767 were somewhat faster than those for the corresponding acetates (triclopyr and 93833 respectively) indicating a preference of AAD-12 (v2) for oxypropionate over oxyacetate side chains. These data show that AAD-12 (v2) is able to effectively degrade pyridyloxyalkanoate herbicides such as triclopyr.

TABLE 9

Rates of pyridyloxyalkanoate cleavage by AAD-12 (v2). 6.8 µg AAD-12 (v2) was incubated with 1 mM substrate, the reaction initiated by addition of α-ketoglutarate and the subsequent increase in absorbance monitored at 325 nm. The background rate of 1.4 mAU/min without α-ketoglutarate was subtracted from the rates with substrate.

| STRUCTURE | ID | Rate (mAU/min) | Rate relative to triclopyr |
|---|---|---|---|
| 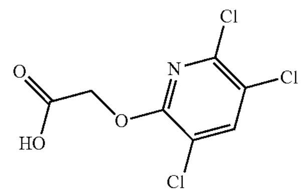 [SMILES: O=C(O)COc1nc(Cl)c(Cl)cc1Cl] | triclopyr | 97 | 1 |
| 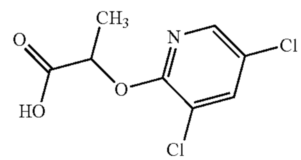 | 66357 | 225 | 2.3 |
| 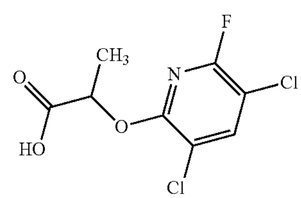 | 91767 | 190 | 0.8 |
| 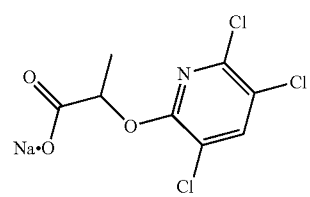 | 116844 | 257 | 1.4 |
| 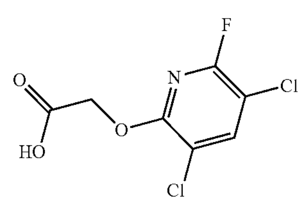 [SMILES: O=C(O)COc1nc(F)c(Cl)cc1Cl] | 93833 | 118 | 0.5 |

6.3—Kinetic Constants of AAD-12 (v2) for 2,4-D, (R,S)-DCP and Triclopyr

The $K_m$ and $k_{cat}$ values of purified AAD-12 (v2) for the herbicides 2,4-D, (R,S)-dichlorprop and triclopyr were determined using the appropriate assay method. Substrate inhibition occurred at high concentrations (>1 mM) of 2,4-D and (R,S)-DCP so concentrations below this were used to fit the data to the Michaelis-Menten equation using Grafit 4.0 (Erithacus Software, UK). No substrate inhibition was noted for triclopyr up to 2 mM. The kinetic constants are summarized in Table 10. From these data, the rate of AAD-12 (v2) cleavage of triclopyr is ~5% that of 2,4-D, under maximal velocity conditions.

TABLE 10

Kinetic constants of AAD-12 (v2) for three herbicide substrates

| Substrate | $K_m$, µM (±SE) | $k_{cat}$, min$^{-1}$ (±SE) | Assay method | Substrate inhibition at 2 mM |
|---|---|---|---|---|
| 2,4-D | 102 (±18.4) | 54.1 (±3.1) | Phenol detection | 55% |
| (R,S)-dichlorprop | 122 (±2.7)* | 63.4 (±0.5) | Phenol detection | 55% |
| Triclopyr | 241 (±30) | 2.6 (±0.1) | ΔA325 nm | 0% |

*Because of the (S)-enantiomeric preference of AAD-12, the $K_m$ value was calculated assuming 50% of the racemic mixture was available as a substrate Example 7—Transformation into *Arabidopsis* and Selection 7.1—*Arabidopsis thaliana* Growth Conditions.

Wildtype *Arabidopsis* seed was suspended in a 0.1% Agarose (Sigma Chemical Co., St. Louis, Mo.) solution. The suspended seed was stored at 4° C. for 2 days to complete dormancy requirements and ensure synchronous seed germination (stratification).

Sunshine Mix LP5 (Sun Gro Horticulture, Bellevue, Wash.) was covered with fine vermiculite and sub-irrigated with Hoagland's solution until wet. The soil mix was allowed to drain for 24 hours. Stratified seed was sown onto the vermiculite and covered with humidity domes (KORD Products, Bramalea, Ontario, Canada) for 7 days.

Seeds were germinated and plants were grown in a Conviron (models CMP4030 and CMP3244, Controlled Environments Limited, Winnipeg, Manitoba, Canada) under long day conditions (16 hours light/8 hours dark) at a light intensity of 120-150 pmol/m$^2$ sec under constant temperature (22° C.) and humidity (40-50%). Plants were initially watered with Hoagland's solution and subsequently with deionized water to keep the soil moist but not wet.

7.2—*Agrobacterium* Transformation.

An LB+agar plate with erythromycin (Sigma Chemical Co., St. Louis, Mo.) (200 mg/L) or spectinomycin (100 mg/L) containing a streaked DH5α colony was used to provide a colony to inoculate 4 ml mini prep cultures (liquid LB+erythromycin). The cultures were incubated overnight at 37° C. with constant agitation. Qiagen (Valencia, Calif.) Spin Mini Preps, performed per manufacturer's instructions, were used to purify the plasmid DNA.

Electro-competent *Agrobacterium tumefaciens* (strains Z707s, EHA101s, and LBA4404s) cells were prepared using a protocol from Weigel and Glazebrook (2002). The competent *Agrobacterium* cells were transformed using an electroporation method adapted from Weigel and Glazebrook (2002). 50 µl of competent agro cells were thawed on ice and 10-25 ng of the desired plasmid was added to the cells. The DNA and cell mix was added to pre-chilled electroporation cuvettes (2 mm). An Eppendorf Electroporator 2510 was used for the transformation with the following conditions, Voltage: 2.4 kV, Pulse length: 5 msec.

After electroporation, 1 ml of YEP broth (per liter: 10 g yeast extract, 10 g Bacto-peptone, 5 g NaCl) was added to the cuvette, and the cell-YEP suspension was transferred to a 15 ml culture tube. The cells were incubated at 28° C. in a water bath with constant agitation for 4 hours. After incubation, the culture was plated on YEP+agar with erythromycin (200 mg/L) or spectinomycin (100 mg/L) and streptomycin (Sigma Chemical Co., St. Louis, Mo.) (250 mg/L). The plates were incubated for 2-4 days at 28° C.

Colonies were selected and streaked onto fresh YEP+agar with erythromycin (200 mg/L) or spectinomycin (100 mg/L) and streptomycin (250 mg/L) plates and incubated at 28° C. for 1-3 days. Colonies were selected for PCR analysis to verify the presence of the gene insert by using vector specific primers. Qiagen Spin Mini Preps, performed per manufacturer's instructions, were used to purify the plasmid DNA from selected *Agrobacterium* colonies with the following exception: 4 ml aliquots of a 15 ml overnight mini prep culture (liquid YEP+erythromycin (200 mg/L) or spectinomycin (100 mg/L)) and streptomycin (250 mg/L)) were used for the DNA purification. An alternative to using Qiagen Spin Mini Prep DNA was lysing the transformed *Agrobacterium* cells, suspended in 10 µl of water, at 100° C. for 5 minutes. Plasmid DNA from the binary vector used in the *Agrobacterium* transformation was included as a control. The PCR reaction was completed using Taq DNA polymerase from Takara Mirus Bio Inc. (Madison, Wis.) per manufacturer's instructions at 0.5× concentrations. PCR reactions were carried out in a MJ Research Peltier Thermal Cycler programmed with the following conditions; 1) 94° C. for 3 minutes, 2) 94° C. for 45 seconds, 3) 55° C. for 30 seconds, 4) 72° C. for 1 minute, for 29 cycles then 1 cycle of 72° C. for 10 minutes. The reaction was maintained at 4° C. after cycling. The amplification was analyzed by 1% agarose gel electrophoresis and visualized by ethidium bromide staining. A colony was selected whose PCR product was identical to the plasmid control.

7.3—*Arabidopsis* Transformation.

*Arabidopsis* was transformed using the floral dip method. The selected colony was used to inoculate one or more 15-30 ml pre-cultures of YEP broth containing erythromycin (200 mg/L) or spectinomycin (100 mg/L) and streptomycin (250 mg/L). The culture(s) was incubated overnight at 28° C. with constant agitation at 220 rpm. Each pre-culture was used to inoculate two 500 ml cultures of YEP broth containing erythromycin (200 mg/L) or spectinomycin (100 mg/L) and streptomycin (250 mg/L) and the cultures were incubated overnight at 28° C. with constant agitation. The cells were then pelleted at approx. 8700×g for 10 minutes at room temperature, and the resulting supernatant discarded. The cell pellet was gently resuspended in 500 ml infiltration media containing: ½× Murashige and Skoog salts/Gamborg's B5 vitamins, 10% (w/v) sucrose, 0.044 µM benzylamino purine (10 µl/liter of 1 mg/ml stock in DMSO) and 300 µl/liter Silwet L-77. Plants approximately 1 month old were dipped into the media for 15 seconds, being sure to submerge the newest inflorescence. The plants were then laid down on their sides and covered (transparent or opaque) for 24 hours, then washed with water, and placed upright. The plants were grown at 22° C., with a 16-hour light/8-hour dark photoperiod. Approximately 4 weeks after dipping, the seeds were harvested.

7.4—Selection of Transformed Plants.

Freshly harvested $T_1$ seed [AAD-12 (v1) gene] was allowed to dry for 7 days at room temperature. $T_1$ seed was sown in 26.5×51-cm germination trays (T.O. Plastics Inc., Clearwater, Minn.), each receiving a 200 mg aliquots of stratified $T_1$ seed (~10,000 seed) that had previously been suspended in 40 ml of 0.1% agarose solution and stored at 4° C. for 2 days to complete dormancy requirements and ensure synchronous seed germination.

Sunshine Mix LP5 (Sun Gro Horticulture Inc., Bellevue, Wash.) was covered with fine vermiculite and subirrigated with Hoagland's solution until wet, then allowed to gravity drain. Each 40 ml aliquot of stratified seed was sown evenly onto the vermiculite with a pipette and covered with humidity domes (KORD Products, Bramalea, Ontario, Canada) for 4-5 days. Domes were removed 1 day prior to initial transformant selection using glufosinate postemergence spray (selecting for the co-transformed PAT gene).

Seven days after planting (DAP) and again 11 DAP, $T_1$ plants (cotyledon and 2-4-1f stage, respectively) were sprayed with a 0.2% solution of Liberty herbicide (200 g ai/L glufosinate, Bayer Crop Sciences, Kansas City, Mo.) at a spray volume of 10 ml/tray (703 L/ha) using a DeVilbiss compressed air spray tip to deliver an effective rate of 280 g ai/ha glufosinate per application. Survivors (plants actively growing) were identified 4-7 days after the final spraying and transplanted individually into 3-inch pots prepared with potting media (Metro Mix 360). Transplanted plants were covered with humidity domes for 3-4 days and placed in a 22° C. growth chamber as before or moved to directly to the greenhouse. Domes were subsequently removed and plants reared in the greenhouse ($22 \pm 5°$ C., $50 \pm 30\%$ RH, 14 h light:10 dark, minimum 500 $\mu E/m^2 s^1$ natural+supplemental light) at least 1 day prior to testing for the ability of AAD-12 (v1) (plant optimized gene) to provide phenoxy auxin herbicide resistance.

$T_1$ plants were then randomly assigned to various rates of 2,4-D. For *Arabidopsis*, 50 g ae/ha 2,4-D is an effective dose to distinguish sensitive plants from ones with meaningful levels of resistance. Elevated rates were also applied to determine relative levels of resistance (50, 200, 800, or 3200 g ae/ha). Tables 10 and 11 show comparisons drawn to an aryloxyalkanoate herbicide resistance gene (AAD-1 (v3)) previously described in PCT/US2005/014737.

All auxin herbicide applications were made using the DeVilbiss sprayer as described above to apply 703 L/ha spray volume (0.4 ml solution/3-inch pot) or applied by track sprayer in a 187 L/ha spray volume. 2,4-D used was either technical grade (Sigma, St. Louis, Mo.) dissolved in DMSO and diluted in water (<1% DMSO final concentration) or the commercial dimethylamine salt formulation (456 g ae/L, NuFarm, St Joseph, Mo.). Dichlorprop used was commercial grade formulated as potassium salt of R-dichlorprop (600 g ai/L, AH Marks). As herbicide rates increased beyond 800 g ae/ha, the pH of the spray solution became exceedingly acidic, burning the leaves of young, tender *Arabidopsis* plants and complicating evaluation of the primary effects of the herbicides. It became standard practice to apply these high rates of herbicides in 200 mM HEPES buffer, pH 7.5.

Some $T_1$ individuals were subjected to alternative commercial herbicides instead of a phenoxy auxin. One point of interest was determining whether the pyridyloxyacetate auxin herbicides, triclopyr and fluroxypyr, could be effectively degraded in planta. Herbicides were applied to $T_1$ plants with use of a track sparyer in a 187 L/ha spray volume. $T_1$ plants that exhibited tolerance to 2,4-D DMA were further accessed in the $T_2$ generation.

7.5—Results of Selection of Transformed Plants.

The first *Arabidopsis* transformations were conducted using AAD-12 (v1) (plant optimized gene). $T_1$ transformants were first selected from the background of untransformed seed using a glufosinate selection scheme. Over 300,000 $T_1$ seed were screened and 316 glufosinate resistant plants were identified (PAT gene), equating to a transformation/selection frequency of 0.10% which lies in the normal range of selection frequency of constructs where PAT+Liberty are used for selection. $T_1$ plants selected above were subsequently transplanted to individual pots and sprayed with various rates of commercial aryloxyalkanoate herbicides. Table 11 compares the response of AAD-12 (v1) and control genes to impart 2,4-D resistance to *Arabidopsis* $T_1$ transformants. Response is presented in terms of % visual injury 2 WAT. Data are presented as a histogram of individuals exhibiting little or no injury (<20%), moderate injury (20-400/), or severe injury (>40%). Since each $T_1$ is an independent transformation event, one can expect significant variation of individual $T_1$ responses within a given rate. An arithmetic mean and standard deviation is presented for each treatment. The range in individual response is also indicated in the last column for each rate and transformation. PAT/Cry1F-transformed *Arabidopsis* served as an auxin-sensitive transformed control. The AAD-12 (v1) gene imparted herbicide resistance to individual $T_1$ *Arabidopsis* plants. Within a given treatment, the level of plant response varied greatly and can be attributed to the fact each plant represents an independent transformation event. Of important note, at each 2,4-D rate tested, there were individuals that were unaffected while some were severely affected. An overall population injury average by rate is presented in Table 11 simply to demonstrate the significant difference between the plants transformed with AAD-12 (v1) versus the wildtype or PAT/Cry1F-transformed controls. Injury levels tend to be greater and the frequency of uninjured plants was lower at elevated rates up to 3,200 g ae/ha (or 6x field rate). Also at these high rates, the spray solution becomes highly acidic unless buffered. *Arabidopsis* grown mostly in the growth chamber has a very thin cuticle and severe burning effects can complicate testing at these elevated rates. Nonetheless, many individuals have survived 3,200 g ae/ha 2,4-D with little or no injury.

TABLE 11

AAD-12 (v1) transformed $T_1$ *Arabidopsis* response to a range of 2,4-D rates applied postemergence, compared to an AAD-1 v3 ($T_4$) homozygous resistant population, or a Pat-Cry1F transformed, auxin-sensitive control.

| | % Injury | | | % Injury | Std |
|---|---|---|---|---|---|
| | <20% | 20-40% | >40% | Ave | Dev |
| AAD-12 (v1) gene $T_1$ transformants Averages | | | | | |
| Untreated control-buffer | 6 | 0 | 0 | 0 | 0 |
| 50 g ae/ha 2,4-D | 6 | 0 | 2 | 16 | 24 |
| 200 g ae/ha 2,4-D | 6 | 1 | 1 | 11 | 18 |
| 800 g ae/ha 2,4-D | 5 | 2 | 1 | 15 | 20 |
| 3200 g ae/ha 2,4-D | 8 | 0 | 0 | 6 | 6 |
| PAT/Cry1F (transformed control) Averages | | | | | |
| Untreated control-buffer | 10 | 0 | 0 | 0 | 0 |
| 50 g ae/ha 2,4-D | 4 | 1 | 5 | 31 | 16 |
| 200 g ae/ha 2,4-D | 0 | 0 | 10 | 70 | 2 |
| 800 g ae/ha 2,4-D | 0 | 0 | 10 | 81 | 8 |
| 3200 g ae/ha 2,4-D | 0 | 0 | 10 | 91 | 2 |
| Homozygous AAD-1 (v3) gene $T_4$ plants Averages | | | | | |
| Untreated control-buffer | 10 | 0 | 0 | 0 | 0 |
| 50 g ae/ha 2,4-D | 10 | 0 | 0 | 0 | 0 |
| 200 g ae/ha 2,4-D | 10 | 0 | 0 | 0 | 0 |
| 800 g ae/ha 2,4-D | 10 | 0 | 0 | 0 | 0 |
| 3200 g ae/ha 2,4-D | 9 | 1 | 0 | 2 | 6 |

Table 12 shows a similarly conducted dose response of $T_1$ *Arabidopsis* to the phenoxypropionic acid, dichlorprop. The data shows that the herbicidally active (R-) isomer of dichlorprop does not serve as a suitable substrate for AAD-12 (v1). The fact that AAD-1 will metabolize R-dichlorprop well enough to impart commercially acceptable tolerance is one distinguishing characteristic that separates the two genes. (Table 12). AAD-1 and AAD-12 are considered R- and S-specific α-ketoglutarate dioxygenases, respectively.

TABLE 12

$T_1$ *Arabidopsis* response to a range of R-dichlorprop rates applied postemergence.

| | % Injury | | | % Injury | |
|---|---|---|---|---|---|
| | <20% | 20-40% | >40% | Ave | Std Dev |
| AAD-12 v1 gene Averages | | | | | |
| Untreated control | 6 | 0 | 0 | 0 | 0 |
| 50 g ae/ha R-dichlorprop | 0 | 0 | 8 | 63 | 7 |
| 200 g ae/ha R-dichlorprop | 0 | 0 | 8 | 85 | 10 |
| 800 g ae/ha R-dichlorprop | 0 | 0 | 8 | 96 | 4 |
| 3200 g ae/ha R-dichlorprop | 0 | 0 | 8 | 98 | 2 |
| PAT/Cry1F Averages | | | | | |
| Untreated control | 10 | 0 | 0 | 0 | 0 |
| 50 g ae/ha R-dichlorprop | 0 | 10 | 0 | 27 | 2 |
| 200 g ae/ha R-dichlorprop | 0 | 0 | 10 | 69 | 3 |
| 800 g ae/ha R-dichlorprop | 0 | 0 | 10 | 83 | 6 |
| 3200 g ae/ha R-dichlorprop | 0 | 0 | 10 | 90 | 2 |
| Homozygous AAD-1 (v3) gene $T_4$ plants | | | | | |
| Untreated control | 10 | 0 | 0 | 0 | 0 |
| 50 g ae/ha R-dichlorprop | 10 | 0 | 0 | 0 | 0 |
| 200 g ae/ha R-dichlorprop | 10 | 0 | 0 | 0 | 0 |
| 800 g ae/ha R-dichlorprop | 10 | 0 | 0 | 0 | 0 |
| 3200 g ae/ha R-dichlorprop | 10 | 0 | 0 | 0 | 0 |

7.6—AAD-12 (v1) as a Selectable Marker.

The ability to use AAD-12 (v1) as a selectable marker using 2,4-D as the selection agent was analyzed initially with *Arabidopsis* transformed as described above. Approximately 50 $T_4$ generation *Arabidopsis* seed (homozygous for AAD-12 (v1)) were spiked into approximately 5,000 wild-type (sensitive) seed. Several treatments were compared, each tray of plants receiving either one or two application timings of 2,4-D in one of the following treatment schemes: 7 DAP, 11 DAP, or 7 followed by 11 DAP. Since all individuals also contained the PAT gene in the same transformation vector, AAD-12 selected with 2,4-D could be directly compared to PAT selected with glufosinate.

Treatments were applied with a DeVilbiss spray tip as previously described. Plants were identified as Resistant or Sensitive 17 DAP. The optimum treatment was 75 g ae/ha 2,4-D applied 7 and 11 days after planting (DAP), was equally effective in selection frequency, and resulted in less herbicidal injury to the transformed individuals than the Liberty selection scheme. These results indicate AAD-12 (v1) can be effectively used as an alternative selectable marker for a population of transformed *Arabidopsis*.

7.7—Heritability.

A variety of $T_1$ events were self-pollinated to produce $T_2$ seed. These seed were progeny tested by applying 2,4-D (200 g ae/ha) to 100 random $T_2$ siblings. Each individual $T_2$ plant was transplanted to 7.5-cm square pots prior to spray application (track sprayer at 187 L/ha applications rate). Seventy-five percent of the $T_1$ families ($T_2$ plants) segregated in the anticipated 3 Resistant:1 Sensitive model for a dominantly inherited single locus with Mendelian inheritance as determined by Chi square analysis (P>0.05).

Seed were collected from 12 to 20 $T_2$ individuals ($T_3$ seed). Twenty-five $T_3$ siblings from each of eight randomly-selected $T_2$ families were progeny tested as previously described. Approximately one-third of the $T_2$ families anticipated to be homozygous (non-segregating populations) have been identified in each line. These data show AAD-12 (v1) is stably integrated and inherited in a Mendelian fashion to at least three generations.

7.8—Additional Foliar Applications Herbicide Resistance in AAD-12 *Arabidopsis*.

The ability of AAD-12 (v1) to provide resistance to other aryloxyalkanoate auxin herbicides in transgenic *Arabidopsis* was determined by foliar application of various substrates. $T_2$ generation *Arabidopsis* seed was stratified, and sown into selection trays much like that of *Arabidopsis* (Example 6.4). A transformed-control line containing PAT and the insect resistance gene Cry1F was planted in a similar manner. Seedlings were transferred to individual 3-inch pots in the greenhouse. All plants were sprayed with the use of a track sprayer set at 187 L/ha. The plants were sprayed with a range of pyridyloxyacetate herbicides: 280-2240 g ae/ha triclopyr (Garlon 3A, Dow AgroSciences) and 280-2240 g ae/ha fluroxypyr (Starane, Dow AgroSciences); and the 2,4-D metabolite resulting from AAD-12 activity, 2,4-dichlorophenol (DCP, Sigma) (at a molar equivalent to 280-2240 g ae/ha of 2,4-D, technical grade DCP was used). All applications were formulated in water. Each treatment was replicated 3-4 times. Plants were evaluated at 3 and 14 days after treatment.

There is no effect of the 2,4-D metabolite, 2,4-dichlorophenol (DCP), on transgenic non-AAD-12 control *Arabidopsis* (Pat/Cry1F). AAD-12-transformed plants were also clearly protected from the triclopyr and fluroxypyr herbicide injury that was seen in the transformed non-resistant controls (see Table 13). These results confirm that AAD-12 (v1) in *Arabidopsis* provides resistance to the pyridyloxyacetic auxins tested. This is the first report of an enzyme with significant activity on pyridyloxyacetic acid herbicides. No other 2,4-D degrading enzyme has been reported with similar activity.

TABLE 13

Comparison of $T_2$ AAD-12 (v1) and transformed control *Arabidopsis* plant response to various foliar-applied auxinic herbicides.

| | Ave % Injury 14DAT | |
|---|---|---|
| Herbicide Treatment | Segregating $T_2$ AAD-12 (v1)plants (pDAB724.01.120) | Pat/Cry1f-Control |
| Pyridyloxyacetic auxins | | |
| 280 g ae/ha Triclopyr | 0 | 52 |
| 560 g ae/ha Triclopyr | 3 | 58 |
| 1120 g ae/ha Triclopyr | 0 | 75* |
| 2240 g ae/ha Triclopyr | 3 | 75* |
| 280 g ae/ha Fluroxypyr | 0 | 75* |
| 560 g ae/ha Fluroxypyr | 2 | 75* |
| 1120 g ae/ha Fluroxypyr | 3 | 75* |
| 2240 g ae/ha Fluroxypyr | 5 | 75* |
| Inactive DCP metabolite | | |
| 280 g ae/ha 2,4-DCP | 0 | 0 |
| 560 g ae/ha 2,4-DCP | 0 | 0 |

TABLE 13-continued

Comparison of $T_2$ AAD-12 (v1) and transformed control Arabidopsis plant response to various foliar-applied auxinic herbicides.

| | Ave % Injury 14DAT | |
|---|---|---|
| Herbicide Treatment | Segregating $T_2$ AAD-12 (v1)plants (pDAB724.01.120) | Pat/Cry1F-Control |
| 1120 g ae/ha 2,4-DCP | 0 | 0 |
| 2240 g ae/ha 2,4-DCP | 0 | 0 |

*Plants in this experiment were stunted and severely epinastic, but remained green and did not receive injury ratings >75%.

7.9—Molecular Analysis of AAD-12 (v1) Arabidopsis.

Invader Assay (methods of Third Wave Agbio Kit Procedures) for PAT gene copy number analysis was performed with total DNA obtained from Qiagen DNeasy kit on multiple AAD-12 (v1) homozygous lines to determine stable integration of the plant transformation unit containing PAT and AAD-12 (v1). Analysis assumed direct physical linkage of these genes as they were contained on the same plasmid.

Results showed that all 2,4-D resistant plants assayed, contained PAT (and thus by inference, AAD-12 (v1)). Copy number analysis showed total inserts ranged from 1 to 5 copies. This correlates, too, with the AAD-12 (v1) protein expression data indicating that the presence of the enzyme yields significantly high levels of resistance to all commercially available phenoxyacetic and pyridyloxyacetic acids.

7.10—Arabidopsis Transformed with Molecular Stack of AAD-12 (v1) and a Glyphosate Resistance Gene.

$T_1$ Arabidopsis seed was produced, as previously described, containing the pDAB3759 plasmid (AAD-12 (v1)+EPSPS) which encodes a putative glyphosate resistance trait. $T_1$ transformants were selected using AAD-12 (v1) as the selectable marker as described in example 7.6. $T_1$ plants (individually transformed events) were recovered from the first selection attempt and transferred to three-inch pots in the greenhouse as previously described. Three different control Arabidopsis lines were also tested: wildtype Columbia-0, AAD-12 (v1)+PAT $T_4$ homozygous lines (pDAB724-transformed), and PAT+Cry1F homozygous line (transformed control). The pDAB3759 and pDAB724 transformed plants were pre-selected at the seedling stage for 2,4-D tolerance. Four days after transplanting, plants were evenly divided for foliar treatment by track sprayer as previously described with 0, 26.25, 105, 420, or 1680 g ae/ha glyphosate (Glyphomax Plus, Dow AgroSciences) in water. All treatments were replicated 5 to 20 times. Plants were evaluated 7 and 14 days after treatment.

Initial resistance assessment indicated plants tolerant to 2,4-D were subsequently tolerant to glyphosate when compared to the response of the three control lines. These results indicate that resistance can be imparted to plants to two herbicides with differening modes of action, including 2,4-D and glyphosate tolerance, allowing application of both herbicides postemergence. Additionally, AAD-12+2,4-D was used effectively as a selectable marker for a true resistance selection.

TABLE 14

$T_1$ Arabidopsis response to a range of glyphosate rates applied postemergence (14 DAT).

| | % Injury | | | % Injury | |
|---|---|---|---|---|---|
| | <20% | 20-40% | >40% | Ave | Std Dev |
| AAD-12 v1 gene + EPSPS + HptII (pDAB3759) (Averages) | | | | | |
| Untreated control | 5 | 0 | 0 | 0 | 0 |
| 26.25 g ae/ha glyphosate | 13 | 2 | 1 | 11 | 16 |
| 105 g ae/ha glyphosate | 10 | 1 | 5 | 34 | 38 |
| 420 g ae/ha glyphosate | 5 | 6 | 5 | 44 | 37 |
| 1680 g ae/ha glyphosate | 0 | 0 | 16 | 85 | 9 |
| PAT/Cry1F Averages | | | | | |
| Untreated control | 5 | 0 | 0 | 0 | 0 |
| 26.25 g ae/ha glyphosate | 0 | 0 | 5 | 67 | 7 |
| 105 g ae/ha glyphosate | 0 | 0 | 5 | 100 | 0 |
| 420 g ae/ha glyphosate | 0 | 0 | 5 | 100 | 0 |
| 1680 g ae/ha glyphosate | 0 | 0 | 5 | 100 | 0 |
| Wildtype (Col-0) Averages | | | | | |
| Untreated control | 5 | 0 | 0 | 0 | 0 |
| 26.25 g ae/ha glyphosate | 0 | 0 | 5 | 75 | 13 |
| 105 g ae/ha glyphosate | 0 | 0 | 5 | 100 | 0 |
| 420 g ae/ha glyphosate | 0 | 0 | 5 | 100 | 0 |
| 1680 g ae/ha glyphosate | 0 | 0 | 5 | 100 | 0 |
| pDAB724 $T_4$ (PAT + AAD-12) Averages | | | | | |
| Untreated control | 5 | 0 | 0 | 0 | 0 |
| 26.25 g ae/ha glyphosate | 0 | 0 | 5 | 66 | 8 |
| 105 g ae/ha glyphosate | 0 | 0 | 5 | 100 | 0 |
| 420 g ae/ha glyphosate | 0 | 0 | 5 | 100 | 0 |
| 1680 g ae/ha glyphosate | 0 | 0 | 5 | 100 | 0 |

7.11—AAD-12 Arabidopsis Genetically Stacked with AAD-1 to Give Wider Spectrum of Herbicide Tolerance.

AAD-12 (v1) (pDAB724) and AAD-1 (v3) (pDAB721) plants were reciprocally crossed and $F_1$ seed was collected. Eight $F_1$ seeds were planted and allowed to grow to produce seed. Tissue samples were taken from the eight $F_1$ plants and subjected to Western analysis to confirm the presence of both genes. It was concluded that all 8 plants tested expressed both AAD-1 and AAD-12 proteins. The seed was bulked and allowed to dry for a week before planting.

One hundred $F_2$ seeds were sown and 280 g ai/ha glufosinate was applied. Ninety-six $F_2$ plants survived glufosinate selection fitting an expected segregation ration for two independently assorting loci for glufosinate resistance (15R: 1S). Glufosinate resistant plants were then treated with 560 g ae/ha R-dichlorprop+560 g ae/ha triclopyr, applied to the plants under the same spray regimen as used for the other testing. Plants were graded at 3 and 14 DAT. Sixty-three of the 96 plants that survived glufosinate selection also survived the herbicide application. These data are consistent with an expected segregation pattern (9R: 6S) of two independently assorting dominant traits where each gene gives resistance to only one of the auxinic herbicides (either R-dichloroprop or triclopyr). The results indicate that AAD-12 (pDAB724) can be successfully stacked with AAD-1 (pDAB721), thus increasing the spectrum herbicides that may be applied to the crop of interest [(2,4-D+R-dichlorprop) and (2,4-D+fluroxypyr+triclopyr), respectively]. This could be useful to bring 2,4-D tolerance to a very sensitive species through conventional stacking of two separate 2,4-D resistance genes. Additionally, if either gene were used as a selectable marker for a third and fourth gene of interest through independent transformation activities, then each gene pair could be brought together through conventional breeding activities and subsequently selected in the $F_1$ generation through paired sprays with herbicides that are exclusive between the AAD-1 and AAD-12 enzymes (as shown with R-dichlorprop and triclopyr for AAD-1 and AAD-12, respectively, above).

Other AAD stacks are also within the scope of the subject invention. The TfdA protein discussed elsewhere herein (Streber et al.), for example, can be used together with the subject AAD-12 genes to impart nover spectrums of herbicide resistance in transgenic plants of the subject invention.

Example 8—WHISKERS-Mediated Transformation of Corn Using Imazethapyr Selection 8.1—Cloning of AAD-12 (v1).

The AAD-12 (v1) gene was cut out of the intermediate vector pDAB3283 as an Nco1/Sac1 fragment. This was ligated directionally into the similarly cut pDAB3403 vector containing the ZmUbi1 monocot promoter. The two fragments were ligated together using T4 DNA ligase and transformed into DH5α cells. Minipreps were performed on the resulting colonies using Qiagen's QIA Spin mini prep kit, and the colonies were digested to check for orientation. This first intermediate construct (pDAB4100) contains the ZmUbi1:AAD-12 (v1) cassette. This construct was digested with Not1 and Pvu1 to liberate the gene cassette and digest the unwanted backbone. This was ligated to Not1 cut pDAB2212, which contains the AHAS selectable marker driven by the Rice Actin promoter OsAct1. The final construct was designated pDAB4101 or pDAS1863, and contains ZmUbi1/AAD-12 (v1)/ZmPer5::OsAct1/AHAS/LZm-Lip.

8.2—Callus/Suspension Initiation.

To obtain immature embryos for callus culture initiation, $F_1$ crosses between greenhouse-grown Hi-II parents A and B (Armstrong et al. 1991) were performed. When embryos were 1.0-1.2 mm in size (approximately 9-10 days post-pollination), ears were harvested and surface sterilized by scrubbing with Liqui-Nox® soap, immersed in 70% ethanol for 2-3 minutes, then immersed in 20% commercial bleach (0.1% sodium hypochlorite) for 30 minutes.

Ears were rinsed in sterile, distilled water, and immature zygotic embryos were aseptically excised and cultured on 15Ag10 medium (N6 Medium (Chu et al., 1975), 1.0 mg/L 2,4-D, 20 g/L sucrose, 100 mg/L casein hydrolysate (enzymatic digest), 25 mM L-proline, 10 mg/L $AgNO_3$, 2.5 g/L Gelrite, pH 5.8) for 2-3 weeks with the scutellum facing away from the medium. Tissue showing the proper morphology (Welter et al., 1995) was selectively transferred at biweekly intervals onto fresh 15Ag10 medium for about 6 weeks, then transferred to 4 medium (N6 Medium, 1.0 mg/L 2,4-D, 20 g/L sucrose, 100 mg/L casein hydrolysate (enzymatic digest), 6 mM L-proline, 2.5 g/L Gelrite, pH 5.8) at bi-weekly intervals for approximately 2 months.

To initiate embryogenic suspension cultures, approximately 3 ml packed cell volume (PCV) of callus tissue originating from a single embryo was added to approximately 30 ml of H9CP+ liquid medium (MS basal salt mixture (Murashige and Skoog, 1962), modified MS Vitamins containing 10-fold less nicotinic acid and 5-fold higher thiamine-HCl, 2.0 mg/L 2,4-D, 2.0 mg/L α-naphthaleneacetic acid (NAA), 30 g/L sucrose, 200 mg/L casein hydrolysate (acid digest), 100 mg/L myo-inositol, 6 mM L-proline, 5% v/v coconut water (added just before subculture), pH 6.0). Suspension cultures were maintained under dark conditions in 125 ml Erlenmeyer flasks in a temperature-controlled shaker set at 125 rpm at 28° C. Cell lines typically became established within 2 to 3 months after initiation. During establishment, suspensions were subcultured every 3.5 days by adding 3 ml PCV of cells and 7 ml of conditioned medium to 20 ml of fresh H9CP+liquid medium using a wide-bore pipette. Once the tissue started doubling in growth, suspensions were scaled-up and maintained in 500 ml flasks whereby 12 ml PCV of cells and 28 ml conditioned medium was transferred into 80 ml H9CP+ medium. Once the suspensions were fully established, they were cryopreserved for future use.

8.3—Cryopreservation and Thawing of Suspensions.

Two days post-subculture, 4 ml PCV of suspension cells and 4 ml of conditioned medium were added to 8 ml of cryoprotectant (dissolved in H9CP+ medium without coconut water, 1 M glycerol, 1 M DMSO, 2 M sucrose, filter sterilized) and allowed to shake at 125 rpm at 4° C. for 1 hour in a 125 ml flask. After 1 hour 4.5 ml was added to a chilled 5.0 ml Corning cryo vial. Once filled individual vials were held for 15 minutes at 4° C. in a controlled rate freezer, then allowed to freeze at a rate of −0.5° C./minute until reaching a final temperature of −40° C. After reaching the final temperature, vials were transferred to boxes within racks inside a Cryoplus 4 storage unit (Forma Scientific) filled with liquid nitrogen vapors.

For thawing, vials were removed from the storage unit and placed in a closed dry ice container, then plunged into a water bath held at 40-45° C. until "boiling" subsided. When thawed, contents were poured over a stack of ~8 sterile 70 mm Whatman filter papers (No. 4) in covered 100×25 mm Petri dishes. Liquid was allowed to absorb into the filters for several minutes, then the top filter containing the cells was transferred onto GN6 medium (N6 medium, 2.0 mg/L 2,4-D, 30 g/L sucrose, 2.5 g/L Gelrite, pH 5.8) for 1 week. After 1 week, only tissue with promising morphology was transferred off the filter paper directly onto fresh GN6 medium. This tissue was subcultured every 7-14 days until 1 to 3 grams was available for suspension initiation into approximately 30 ml H9CP+ medium in 125 ml Erlenmeyer flasks. Three milliliters PCV was subcultured into fresh H9CP+ medium every 3.5 days until a total of 12 ml PCV was obtained, at which point subculture took place as described previously.

8.4—Stable Transformation

Approximately 24 hours prior to transformation, 12 ml PCV of previously cryopreserved embryogenic maize suspension cells plus 28 ml of conditioned medium was subcultured into 80 ml of GN6 liquid medium (GN6 medium lacking Gelrite) in a 500 ml Erlenmeyer flask, and placed on a shaker at 125 rpm at 28° C. This was repeated 2 times using the same cell line such that a total of 36 ml PCV was distributed across 3 flasks. After 24 hours the GN6 liquid media was removed and replaced with 72 ml GN6 S/M osmotic medium (N6 Medium, 2.0 mg/L 2,4-D, 30 g/L sucrose, 45.5 g/L sorbitol, 45.5 g/L mannitol, 100 mg/L myo-inositol, pH 6.0) per flask in order to plasmolyze the cells. The flasks were placed on a shaker shaken at 125 RPM in the dark for 30-35 minutes at 28° C., and during this time a 50 mg/ml suspension of silicon carbide whiskers was prepared by adding the appropriate volume 8.1 ml of GN6 S/M liquid medium to ~405 mg of pre-autoclaved, sterile silicon carbide whiskers (Advanced Composite Materials, Inc.).

After incubation in GN6 S/M, the contents of each flask were pooled into a 250 ml centrifuge bottle. Once all cells settled to the bottom, all but ~14 ml of GN6 S/M liquid was drawn off and collected in a sterile 1-L flask for future use. The pre-wetted suspension of whiskers was vortexed for 60 seconds on maximum speed and 8.1 ml was then added to the bottle, to which 170 µg DNA was added as a last step. The bottle was immediately placed in a modified Red Devil 5400 commercial paint mixer and agitated for 10 seconds. After agitation, the cocktail of cells, media, whiskers and DNA was added to the contents of the 1-L flask along with 125 ml fresh GN6 liquid medium to reduce the osmoticant. The cells were allowed to recover on a shaker at 125 RPM for 2 hours at 28° C. before being filtered onto Whatman #4 filter paper (5.5 cm) using a glass cell collector unit that was connected to a house vacuum line.

Approximately 2 ml of dispersed suspension was pipetted onto the surface of the filter as the vacuum was drawn. Filters were placed onto 60×20 mm plates of GN6 medium. Plates were cultured for 1 week at 28° C. in a dark box.

After 1 week, filter papers were transferred to 60×20 mm plates of GN6 (3P) medium (N6 Medium, 2.0 mg/L 2,4-D, 30 g/L sucrose, 100 mg/L myo-inositol, 3 µM imazethapyr from Pursuit® DG, 2.5 g/L Gelrite, pH 5.8). Plates were placed in boxes and cultured for an additional week.

Two weeks post-transformation, the tissue was embedded by scraping all cells on the plate into 3.0 ml of melted GN6 agarose medium (N6 medium, 2.0 mg/L 2,4-D, 30 g/L sucrose, 100 mg/L myo-inositol, 7 g/L Sea Plaque agarose, pH 5.8, autoclaved for only 10 minutes at 121° C.) containing 3 µM imazethapyr from Pursuit® DG. The tissue was broken up and the 3 ml of agarose and tissue were evenly poured onto the surface of a 100×15 mm plate of GN6 (3P). This was repeated for all remaining plates. Once embedded, plates were individually sealed with Nescofilm® or Parafilm M®, and then cultured until putative isolates appeared.

8.4.1—Protocol for Isolate Recovery and Regeneration.

Putatively transformed events were isolated off the Pursuit®-containing embedded plates approximately 9 weeks post-transformation by transferring to fresh selection medium of the same concentration in 60×20 mm plates. If sustained growth was evident after approximately 2-3 weeks, the event was deemed to be resistant and was submitted for molecular analysis.

Regeneration was initiated by transferring callus tissue to a cytokinin-based induction medium, 28 (3P), containing 3 µM imazethapyr from Pursuit® DG, MS salts and vitamins, 30.0 g/L sucrose, 5 mg/L BAP, 0.25 mg/L 2,4-D, 2.5 g/L Gelrite; pH 5.7. Cells were allowed to grow in low light (13 µEm$^{-2}$s$^{-1}$) for one week, then higher light (40 µEm$^{-2}$s$^{-1}$) for another week, before being transferred to regeneration medium, 36 (3P), which was identical to 28 (3P) except that it lacked plant growth regulators. Small (3-5 cm) plantlets were removed and placed into 150×25-mm culture tubes containing selection-free SHGA medium (Schenk and Hildebrandt basal salts and vitamins, 1972; 1 g/L myo-inositol, 10 g/L sucrose, 2.0 g/L Gelrite, pH 5.8). Once plantlets developed a sufficient root and shoot system, they were transplanted to soil in the greenhouse.

From 4 experiments, full plantlets, comprised of a shoot and root, were formed in vitro on the embedded selection plates under dark conditions without undergoing a traditional callus phase. Leaf tissue from nine of these "early regenerators" were submitted for coding region PCR and Plant Transcription Unit (PTU) PCR for the AAD-12 gene and gene cassette, respectively. All had an intact AAD-12 coding region, while 3 did not have a full-length PTU (Table 15). These "early regenerators" were identified as 4101 events to differentiate them from the traditionally-derived events, which were identified as "1283" events. Plants from 19 additional events, obtained via standard selection and regeneration, were sent to the greenhouse, grown to maturity and cross-pollinated with a proprietary inbred line in order to produce T$_1$ seed. Some of the events appear to be clones of one another due to similar banding patterns following Southern blot, so only 14 unique events were represented. To plants from events were tolerant 70 g/ha imazethapyr. Invader analysis (AHAS gene) indicated insertion complexity ranging from 1 to >10 copies. Thirteen events contained the compete coding region for AAD-12; however, further analysis indicated the complete plant transformation unit had not been incorporated for nine events. None of the compromised 1863 events were advanced beyond the T1 stage and further characterization utilized the 4101 events.

8.5—Molecular Analysis: Maize Materials and Methods.

8.5.1—Tissue Harvesting DNA Isolation and Quantification.

Fresh tissue is placed into tubes and lyophilized at 4° C. for 2 days. After the tissue is fully dried, a tungsten bead (Valenite) is placed in the tube and the samples are subjected to 1 minute of dry grinding using a Kelco bead mill. The standard DNeasy DNA isolation procedure is then followed (Qiagen, DNeasy 69109). An aliquot of the extracted DNA is then stained with Pico Green (Molecular Probes P7589) and read in the fluorometer (BioTek) with known standards to obtain the concentration in ng/µl.

8.5.2—Invader Assay Analysis.

The DNA samples are diluted to 20 ng/µl then denatured by incubation in a thermocycler at 95° C. for 10 minutes. Signal Probe mix is then prepared using the provided oligo mix and MgCl$_2$ (Third Wave Technologies). An aliquot of 7.5 µl is placed in each well of the Invader assay plate followed by an aliquot of 7.5 µl of controls, standards, and 20 ng/µl diluted unknown samples. Each well is overlaid with 15 µl of mineral oil (Sigma). The plates are then incubated at 63° C. for 1 hour and read on the fluorometer (Biotek). Calculation of % signal over background for the target probe divided by the % signal over background internal control probe will calculate the ratio. The ratio of known copy standards developed and validated with Southern blot analysis is used to identify the estimated copy of the unknown events.

8.5.3—Polymerase Chain Reaction.

A total of 100 ng of total DNA is used as the template. 20 mM of each primer is used with the Takara Ex Taq PCR Polymerase kit (Mirus TAKRR001A). Primers for the AAD-12 (v1) PTU are Forward-GAACAGTTAGACATG-GTCTAAAGG (SEQ ID NO:8) and Reverse-GCTG-CAACACTGATAAATGCCAACTGG (SEQ ID NO:9). The PCR reaction is carried out in the 9700 Geneamp thermocycler (Applied Biosystems), by subjecting the samples to 94° C. for 3 minutes and 35 cycles of 94° C. for 30 seconds, 63° C. for 30 seconds, and 72° C. for 1 minute and 45 seconds followed by 72° C. for 10 minutes.

Primers for AAD-12 (v1) Coding Region PCR are Forward-ATGGCTCAGACCACTCTCCAAA (SEQ ID NO:10) and Reverse-AGCTGCATCCATGCCAGGGA (SEQ ID NO: 11). The PCR reaction is carried out in the 9700 Geneamp thermocycler (Applied Biosystems), by subjecting the samples to 94° C. for 3 minutes and 35 cycles of 94° C. for 30 seconds, 65° C. for 30 seconds, and 72° C. for 1 minute and 45 seconds followed by 72° C. for 10 minutes. PCR products are analyzed by electrophoresis on a 1% agarose gel stained with EtBr.

8.5.4—Southern Blot Analysis.

Southern blot analysis is performed with genomic DNA obtained from Qiagen DNeasy kit. A total of 2 µg of genomic leaf DNA or 10 µg of genomic callus DNA is subjected to an overnight digestion using BSM I and SWA I restriction enzymes to obtain PTU data.

After the overnight digestion an aliquot of ~100 ng is run on a 1% gel to ensure complete digestion. After this assurance the samples are run on a large 0.85% agarose gel overnight at 40 volts. The gel is then denatured in 0.2 M NaOH, 0.6 M NaCl for 30 minutes. The gel is then neutralized in 0.5 M Tris HCl, 1.5 M NaCl pH of 7.5 for 30 minutes. A gel apparatus containing 20×SSC is then set up to obtain a gravity gel to nylon membrane (Millipore INYC00010) transfer overnight. After the overnight transfer the membrane is then subjected to UV light via a crosslinker (Stratagene UV stratalinker 1800) at 1200×100 microjoules. The membrane is then washed in 0.1% SDS, 0.1 SSC for 45 minutes. After the 45 minute wash, the membrane is baked for 3 hours at 80° C. and then stored at 4° C. until hybridization. The hybridization template fragment is prepared using the above coding region PCR using plasmid DNA. The product is run on a 1% agarose gel and excised and then gel extracted using the Qiagen (28706) gel extraction procedure. The membrane is then subjected to a prehybridization at 60° C. step for 1 hour in Perfect Hyb buffer (Sigma H7033). The Prime it RmT dCTP-labeling rxn (Stratagene 300392) procedure is used to develop the p32 based probe (Perkin Elmer). The probe is cleaned up using the Probe Quant. G50 columns (Amersham 27-5335-01). Two million counts CPM are used to hybridize the southern blots overnight. After the overnight hybridization the blots are then subjected to two 20 minute washes at 65° C. in 0.1% SDS, 0.1 SSC. The blots are then exposed to film overnight, incubating at −80° C.

8.6—Postemergence Herbicide Tolerance in AAD-12 Transformed $T_0$ Corn.

Four $T_0$ events were allowed to acclimate in the greenhouse and were grown until 2-4 new, normal looking leaves had emerged from the whorl (i.e., plants had transitioned from tissue culture to greenhouse growing conditions). Plants were grown at 27° C. under 16 hour light:8 hour dark conditions in the greenhouse. Plants were then treated with commercial formulations of either Pursuit® (imazethapyr) or 2,4-D Amine 4. Pursuit® was sprayed to demonstrate the function of the selectable marker gene present within the events tested. Herbicide applications were made with a track sprayer at a spray volume of 187 L/ha, 50-cm spray height.

Plants were sprayed with either a lethal dose of imazethapyr (70 g ae/ha) or a rate of 2,4-D DMA salt capable of significant injury to untransformed corn lines (2240 g ae/ha). A lethal dose is defined as the rate that causes >95% injury to the Hi-II inbred. Hi-II is the genetic background of the transformants of the present invention.

Several individuals were safened from the herbicides to which the respective genes were to provide resistance. The individual clone '001' from event "001" (a.k.a., 4101(0)-001-001), however, did incur minor injury but recovered by 14 DAT. Three of the four events were moved forward and individuals were crossed with 5XH751 and taken to the next generation. Each herbicide tolerant plant was positive for the presence of the AAD-12 coding region (PCR assay) or the presence of the AHAS gene (Invader assay) for 2,4-D and imazethapyr-tolerant plants, respectively. AAD-12 protein was detected in all 2,4-D tolerant $T_0$ plants events containing an intact coding region. The copy number of the transgene(s) (AHAS, and by inference AAD-12) varied significantly from 1 to 15 copies. Individual $T_0$ plants were grown to maturity and cross-pollinated with a proprietary inbred line in order to produce $T_1$ seed.

TABLE 15

Characterization of $T_0$ corn plants transformed with AAD-12.

| Event | Spray Treatment | % Injury (14 DAT) | AAD-12 ELISA (ppm TSP) | AAD-12 PCR (Coding Region) | AAD12 PCR (PTU) | AHAS Copy # (Invader) |
|---|---|---|---|---|---|---|
| 4101(0)003.001 | 2240 g ae/ha 2,4-D | 0 | 146.9 | + | + | 1 |
| 4101(0)003.003 | 2240 g ae/ha 2,4-D | 0 | 153.5 | + | + | 1 |
| 4101(0)005.001 | 2240 g ae/ha 2,4-D | 0 | 539.7 | + | + | 9 |
| 4101(0)005.0012 | 0 g ae/ha 2,4-D | 0 | 562.9 | + | + | 7 |
| 4101(0)001.001 | 70 g ae/ha imazethapyr | 5 | 170.7 | + | + | 6 |
| 4101(0)002.001 | 0 g ae/ha imazethapyr | 0 | 105.6 | + | − | 2 |
| 4101(0)002.002 | 70 g ae/ha imazethapyr | 0 | 105.3 | + | − | 2 |
| 4101(0)003.002 | 70 g ae/ha imazethapyr | 0 | 0 | + | band smaller than expected | 15 |

8.7—Verification of High 2,4-D Tolerance in $T_1$ Corn.

$T_1$ AAD-12 (v1) seed were planted into 3-inch pots containing Metro Mix media and at 2 leaf stage were sprayed with 70 g ae/ha imazethapyr to eliminate nulls. Surviving plants were transplanted to 1-gallon pots containing Metro Mix media and placed in the same growth conditions as before. At V3-V4 stage the plants were sprayed in the track sprayer set to 187 L/ha at either 560 or 2240 g ae/ha 2,4-D DMA. Plants were graded at 3 and 14 DAT and compared to 5XH751×Hi II control plants. A grading scale of 0-10 (no injury to extreme auxin injury) was developed to distinguish brace root injury. Brace Root grades were taken on 14DAT to show 2,4-D tolerance. 2,4-D causes brace root malformation, and is a consistent indicator of auxinic herbicide injury in corn. Brace root data (as seen in the table below) demonstrates that 2 of the 3 events tested were robustly tolerant to 2240 g ae/ha 2,4-D DMA. Event "pDAB4101(0)001.001" was apparently unstable; however, the other two events were robustly tolerant to 2,4-D and 2,4-D+imazethapyr or 2,-4D+glyphosate (see Table 16).

TABLE 16

Brace Root injury of AAD-12 (v1) transformed $T_1$ plants and Untransformed control corn plants. A scale of 0-10, 10 being the highest, was used for grading the 2,4-D DMA injury. Results are a visual average of four replications per treatment.

| Herbicide | Untransformed Control | AAD-12 (v1) pDAB4101(0)003.003 | AAD-12 (v1) pDAB4101(0)001.001 | AAD-12 (v1) pDAB4101(0)005.001 |
|---|---|---|---|---|
| | | Average Brace Root Injury (0-10 Scale) | | |
| 0 g ae/ha 2,4-D DMA | 0 | 0 | 0 | 0 |
| 2240 g ae/ha 2,4-D DMA | 9 | 1 | 8 | 0 |

8.8—AAD-12 (v1) Heritability in Corn.

A progeny test was also conducted on seven AAD-12 (v1) $T_1$ families that had been crossed with 5XH751. The seeds were planted in three-inch pots as described above. At the 3 leaf stage all plants were sprayed with 70 g ae/ha imazethapyr in the track sprayer as previously described. After 14 DAT, resistant and sensitive plants were counted. Four out of the six lines tested segregated as a single locus, dominant Mendelian trait (1R:1S) as determined by Chi square analysis. Surviving plants were subsequently sprayed with 2,4-D and all plants were deemed tolerant to 2,4-D (rates≥560 g ae/ha). AAD-12 is heritable as a robust aryloxyalkanoate auxin resistance gene in multiple species when reciprocally crossed to a commercial hybrid.

8.9—Stacking of AAD-12 (v1) to Increase Herbicide Spectrum

AAD-12 (v1) (pDAB4101) and elite Roundup Ready inbred (BE1146RR) were reciprocally crossed and $F_1$ seed was collected. The seed from two $F_1$ lines were planted and treated with 70 g ae/ha imazethapyr at the V2 stage to eliminate nulls. To the surviving plants, reps were separated and either treated with 1120 g ae/ha 2,4-D DMA+70 g ae/ha imazethapyr (to confirm presence of AHAS gene) or 1120 g ae/ha 2,4-D DMA+1680 g ae/ha glyphosate (to confirm the presence of the Round Up Ready gene) in a track sprayer calibrated to 187 L/ha. Plants were graded 3 and 16 DAT. Spray data showed that AAD-12 (v1) can be conventionally stacked with a glyphosate tolerance gene (such as the Roundup CP4-EPSPS gene) or other herbicide tolerance genes to provide an increased spectrum of herbicides that may be applied safely to corn. Likewise imidazolinone+2, 4-D+glyphosate tolerance was observed in $F_1$ plants and showed no negative phenotype by the molecular or breeding stack combinations of these multiple transgenes.

TABLE 17

Data demonstrating increase herbicide tolerance spectrum resulting from an $F_1$ stack of AAD-12 (v1) and BE1146RR (an elite glyphosate tolerant inbred abbreviated as AF).

| Herbicide | Untransformed Control | 2P782 (Roundup Ready Control) | AAD-12 (v1) pDAB4101(0)003.R003.AF | AAD-12 (v1) pDAB4101(0)005.R001.AF |
|---|---|---|---|---|
| | | | Average % Injury 16DAT | |
| 0 g ae/ha 2,4-D DMA | 0 | 0 | 0 | 0 |
| 1120 g ae/ha 2,4-D DMA | 21 | 19 | 0 | 0 |
| 1120 g ae/ha 2,4-D DMA + 70 g ae/ha imazethapyr | 100 | 100 | 5 | 1 |
| 01120 g ae/ha 2,4-D DMA + 1680 g ae/ha glyphosate | 100 | 71 | 2 | 5 |

8.10—Field Tolerance of DDAB4101 Transformed Corn Plants to 2,4-D, Triclopyr and Fluroxypyr Herbicides.

Field level tolerance trials were conducted on two AAD-12 (v1) pDAB4101 events (4101(0)003.R.003.AF and 4101 (0)005.R001.AF) and one Roundup Ready (RR) control hybrid (2P782) at Fowler, Ind. and Wayside, Miss. Seeds were planted with cone planter on 40-inch row spacing at Wayside and 30 inch spacing at Fowler. The experimental design was a randomized complete block design with 3 replications. Herbicide treatments were 2,4-D (dimethylamine salt) at 1120, 2240 and 4480 g ae/ha, triclopyr at 840 g ae/ha, fluroxypyr at 280 g ae/ha and an untreated control. The AAD-12 (v1) events contained the AHAS gene as a selectable marker. The $F_2$ corn events were segregating so the AAD-12 (v1) plants were treated with imazethapyr at 70 g ae/ha to remove the null plants. Herbicide treatments were applied when corn reached the V6 stage using compressed air backpack sprayer delivering 187 L/ha carrier volume at 130-200 kpa pressure. Visual injury ratings were taken at 7, 14 and 21 days after treatment. Brace root injury ratings were taken at 28DAT on a scale of 0-10 with 0-1 being slight brace root fusing, 1-3 being moderate brace root swelling/wandering and root proliferation, 3-5 being moderate brace root fusing, 5-9 severe brace root fusing and malformation and 10 being total inhibition of brace roots.

AAD-12 (v1) event response to 2,4-D, triclopyr, and fluroxypyr at 14 days after treatment are shown in Table 18.

Crop injury was most severe at 14 DAT. The RR control corn (2P782) was severely injured (44% at 14 DAT) by 2,4-D at 4480 g ae/ha, which is 8 times (8×) the fnormal field use rate. The AAD-12 (v1) events all demonstrated excellent tolerance to 2,4-D at 14 DAT with 0% injury at the 1, 2 and 4× rates, respectively. The control corn (2P782) was severely injured (31% at 14 DAT) by the 2× rate of triclopyr (840 g ae/ha). AAD-12 (v1) events demonstrated tolerance at 2× rates of triclopyr with an average of 3% injury at 14 DAT across the two events. Fluroxypyr at 280 g ae/ha caused 11% visual injury to the wild-type corn at 14 DAT. AAD-12 (v1) events demonstrated increased tolerance with an average of 8% injury at 5 DAT.

Applications of auxinic herbicides to corn in the V6 growth stage can cause malformation of the brace roots. Table 18 shows the severity of the brace root injury caused by 2,4-D, triclopyr, and fluroxypyr. Triclopyr at 840 g ae/ha caused the most severe brace root fusing and malformation resulting in an average brace root injury score of 7 in the 2P782 control-type corn. Both AAD-12 (v1) corn events showed no brace root injury from the triclopyr treatment. Brace root injury in 2P782 corn increased with increasing rates of 2,4-D. At 4480 g ae/ha of 2,4-D, the AAD-12 events showed no brace root injury; whereas, severe brace root fusing and malformation was seen in the 2P782 hybrid. Fluroxypyr caused only moderate brace root swelling and wandering in the wild-type corn with the AAD-12 (v1) events showing no brace root injury.

This data clearly shows that AAD-12(v1) conveys high level tolerance in corn to 2,4-D, triclopyr and fluroxypyr at rates far exceeding those commercially used and that cause non-AAD-12 (v1) corn severe visual and brace root injury.

TABLE 18

Visual Injury of AAD-12 events and wild-type corn following foliar applications of 2,4-D, triclopyr and fluroxypyr under field conditions.

| Treatment | Rate (g ae/ha) | % Visual Injury 14 DAT | | |
|---|---|---|---|---|
| | | AAD-12 4101(0)003.-R.003.AF | AAD-12 4101(0)005.-001.AF | 2P782 control |
| Untreated | 0 | 0 | 0 | 0 |
| 2,4-D | 1120 | 0 | 0 | 9 |
| 2,4-D | 2240 | 0 | 1 | 20 |
| 2,4-D | 4480 | 0 | 1 | 34 |
| Fluroxypyr | 280 | 1 | 5 | 11 |
| Triclopyr | 840 | 3 | 4 | 31 |
| Dicamba | 840 | 8 | 8 | 11 |

TABLE 19

Brace root injury ratings for AAD-12 and wild-type corn plants in response to 2,4-D, triclopyr and fluroxypyr under field conditions.

| Treatment | Rate (g ae/ha) | Brace Root Injury Rating (0-10 scale) 28 DAT | | |
|---|---|---|---|---|
| | | AAD-12 event 4101(0)003.-R.003.AF | AAD-12 event 4101(0)005.-001.AF | Wild-type NK603 |
| Untreated | 0 | 0 | 0 | 0 |
| 2,4-D | 1120 | 0 | 0 | 3 |
| 2,4-D | 2240 | 0 | 0 | 5 |
| 2,4-D | 4480 | 0 | 0 | 6 |
| Fluroxypyr | 280 | 0 | 0 | 2 |
| Triclopyr | 840 | 0 | 0 | 7 |
| Dicamba | 840 | 1 | 1 | 1 |

Example 9—Protein Detection from Transformed Plants Via Antibody 9.1—Extracting AAD-12 (v1) from Plant Leaves.

Approximately 50 to 100 mg of leaf tissue was cut into small pieces (or 4 single-hole-punched leaf discs) and put into 2-ml cluster tubes containing 2 stainless steel BB beads (4.5 mm; Daisy Co., cat. #145462-000). Five hundred microliters of plant extraction buffer (PBS containing 0.05% Tween 20 and 1% Bovine serum albumin) was added to each sample. The tubes were capped and secured in the Geno/Grinder (Model 2000-115, Certiprep, Metuchen, N.J.) and shaken for 6 min with setting at 1× of 500 rpm. Tubes were centrifuged at 5000×g for 10 min and supernatant containing the soluble proteins were analyzed for AAD-12 (v1) using Western Blots and ELISA.

9.2—Enzyme Linked Immuno-Sorbent Assay (ELISA).

The assay was conducted at room temperature unless otherwise stated. One hundred micro-liter of purified anti-AAD-12 antibody (0.5 µg/ml) was coated on 96-well microtiter well and incubated at 4° C. for 16 hours. The plate was washed four times with washing buffer (100 mM phosphate buffered saline (PBS; pH 7.4) containing 0.05% Tween 20) using a plate washer, followed by blocking with 4% skim milk dissolved in PBS for 1 hour. After washing, 100 µL standard AAD-12 of known concentrations or plant extracts from different samples were incubated in the wells. For standard curve, purified AAD-12 was diluted 2-fold serially from 52 to 0.813 ng/ml in triplicates. Plant extracts were diluted 5, 10, 20, and 40-fold in PBS and analyzed in duplicates. After 1 hour incubation, the plate was washed as above. One hundred micro-liter anti-AAD-12 antibody-HRP conjugate (0.5 ug/ml) was incubated in each well for 1 hour before washing. One hundred micro-liter HRP substrate, 1-Step™ Ultra TMB-ELISA (Pierce, Rockford, Ill.), was incubated in each well for 10 minutes before the reaction was stopped by adding 100 µL 0.4N $H_2SO_4$. The OD of each well was measured using a microplate reader at 450 nm. To determine the concentrations of AAD-12 (v1) in plant extract, the OD value of duplicates were averaged and extrapolated from the standard curve using the Softmax® Pro ver. 4.0 (Molecular Devices).

For comparison, each sample was normalized with its fresh weight and percent expression was calculated.

9.3—Western Blotting Analysis.

Plant extracts or AAD-12 standards (5 and 0.5 µg/ml) were incubated with Laemmli sample buffer at 95° C. for 10 minutes and electrophoretically separated in 8-16% Tris-Glycine Precast gel. Proteins were then electro-transferred onto nitrocellulose membrane using standard protocol. After blocking in 4% skim milk in PBS, AAD-12 (v1) protein was detected by anti-AAD-12 antiserum followed by goat anti-rabbit/HRP conjugates. The detected protein was visualized by chemiluminescence substrate ECL Western Analysis Reagent (Amersham, NJ).

Example 10—Tobacco Transformation

Tobacco transformation with *Agrobacterium tumefaciens* was carried out by a method similar, but not identical, to published methods (Horsch et al., 1988). To provide source tissue for the transformation, tobacco seed (*Nicotiana tabacum* cv. KY160) was surface sterilized and planted on the surface of TOB-medium, which is a hormone-free Murashige and Skoog medium (Murashige and Skoog, 1962) solidified with agar. Plants were grown for 6-8 weeks in a lighted incubator room at 28-30° C. and leaves collected sterilely for use in the transformation protocol. Pieces of approximately one square centimeter were sterilely cut from these leaves, excluding the midrib. Cultures of the *Agrobacterium* strains (EHA101S containing pDAB3278, aka pDAS1580, AAD-12 (v1)+PAT), grown overnight in a flask on a shaker set at 250 rpm at 28° C., were pelleted in a centrifuge and resuspended in sterile Murashige & Skoog salts, and adjusted to a final optical density of 0.5 at 600 nm. Leaf pieces were dipped in this bacterial suspension for approximately 30 seconds, then blotted dry on sterile paper towels and placed right side up on TOB+ medium (Murashige and Skoog medium containing 1 mg/L indole acetic acid and 2.5 mg/L benzyladenine) and incubated in the dark at 28° C. Two days later the leaf pieces were moved to TOB+ medium containing 250 mg/L cefotaxime (Agri-Bio, North Miami, Fla.) and 5 mg/L glufosinate ammonium (active ingredient in Basta, Bayer Crop Sciences) and incubated at 28-30° C. in the light. Leaf pieces were moved to fresh TOB+ medium with cefotaxime and Basta twice per week for the first two weeks and once per week thereafter. Four to six weeks after the leaf pieces were treated with the bacteria, small plants arising from transformed foci were removed from this tissue preparation and planted into medium TOB-containing 250 mg/L cefotaxime and 10 mg/L Basta in Phytatray™ II vessels (Sigma). These plantlets were grown in a lighted incubator room. After 3 weeks, stem cuttings were taken and re-rooted in the same media. Plants were ready to send out to the greenhouse after 2-3 additional weeks.

Plants were moved into the greenhouse by washing the agar from the roots, transplanting into soil in 13.75 cm square pots, placing the pot into a Ziploc® bag (SC Johnson & Son, Inc.), placing tap water into the bottom of the bag, and placing in indirect light in a 30° C. greenhouse for one week. After 3-7 days, the bag was opened; the plants were fertilized and allowed to grow in the open bag until the plants were greenhouse-acclimated, at which time the bag was removed. Plants were grown under ordinary warm greenhouse conditions (30° C., 16 hour day, 8 hour night, minimum natural+supplemental light=500 $\mu E/m^2 s^1$).

Prior to propagation, $T_0$ plants were sampled for DNA analysis to determine the insert copy number. The PAT gene which was molecularly linked to AAD-12 (v1) was assayed for convenience. Fresh tissue was placed into tubes and lyophilized at 4° C. for 2 days. After the tissue was fully dried, a tungsten bead (Valenite) was placed in the tube and the samples were subjected to 1 minute of dry grinding using a Kelco bead mill. The standard DNeasy DNA isolation procedure was then followed (Qiagen, DNeasy 69109). An aliquot of the extracted DNA was then stained with Pico Green (Molecular Probes P7589) and read in the fluorometer (BioTek) with known standards to obtain the concentration in ng/µl.

The DNA samples were diluted to 9 ng/µl and then denatured by incubation in a thermocycler at 95° C. for 10 minutes. Signal Probe mix was then prepared using the provided oligo mix and $MgCl_2$ (Third Wave Technologies). An aliquot of 7.5 µl was placed in each well of the Invader assay plate followed by an aliquot of 7.5 µl of controls, standards, and 20 ng/µl diluted unknown samples. Each well was overlaid with 15 µl of mineral oil (Sigma). The plates were then incubated at 63° C. for 1.5 hours and read on the fluorometer (Biotek). Calculation of % signal over background for the target probe divided by the % signal over background internal control probe will calculate the ratio. The ratio of known copy standards developed and validated with southern blot analysis was used to identify the estimated copy of the unknown events.

All events were also assayed for the presence of the AAD-12 (v1) gene by PCR using the same extracted DNA samples. A total of 100 ng of total DNA was used as template. 20 mM of each primer was used with the Takara Ex Taq PCR Polymerase kit. Primers for the Plant Transcription Unit (PTU) PCR AAD-12 were (SdpacodF: ATG-GCTCA TGCTGCCCTCAGCC) (SEQ ID NO:12) and (SdpacodR: CGGGCAGGCCTAACTCCACC AA) (SEQ ID NO:13). The PCR reaction was carried out in the 9700 Geneamp thermocycler (Applied Biosystems), by subjecting the samples to 94° C. for 3 minutes and 35 cycles of 94° C. for 30 seconds, 64° C. for 30 seconds, and 72° C. for 1 minute and 45 seconds followed by 72° C. for 10 minutes. PCR products were analyzed by electrophoresis on a 1% agarose gel stained with EtBr. Four to 12 clonal lineages from each of 18 PCR positive events with 1-3 copies of PAT gene (and presumably AAD-12 (v1) since these genes are physically linked) were regenerated and moved to the greenhouse.

10.1 Postemergence Herbicide Tolerance in AAD-12 (v1) Transformed $T_0$ Tobacco $T_0$ plants from each of the 19 events were challenged with a wide range of 2,4-D, triclopyr, or fluroxypyr sprayed on plants that were 3-4 inches tall. Spray applications were made as previously described using a track sprayer at a spray volume of 187 L/ha. 2,4-D dimethylamine salt (Riverside Corp) was applied at 0, 140, 560, or 2240 g ae/ha to representative clones from each event mixed in deionized water. Fluroxypyr was likewise applied at 35, 140, or 560 g ae/ha. Triclopyr was applied at 70, 280, or 1120 g ae/ha. Each treatment was replicated 1-3 times. Injury ratings were recorded 3 and 14 DAT. Every event tested was more tolerant to 2,4-D than the untransformed control line KY160. In several events, some initial auxinic herbicide-related epinasty occurred at doses of 560 g ae/ha 2,4-D or less. Some events were uninjured at 2,4-D applied at 2240 g ae/ha (equivalent to 4× field rate). On the whole, AAD-12 (v1) events were more sensitive to fluroxypyr, followed by triclopyr, and least affected by 2,4-D. The quality of the events with respect to magnitude of resistance was discerned using $T_0$ plant responses to 560 g ae/ha fluroxypyr. Events were categorized into "low" (>40% injury 14 DAT), "medium" (20-40% injury), "high" (<20% injury). Some events were inconsistent in response among replicates and were deemed "variable."

TABLE 20

Tobacco T0 events transformed with pDAS1580 (AAD-12 (v1) + PAT)

| # Tube | Plant ID | Copy # PAT | PTU PCR AAD-12 | Full PTU and Under 2 | Full PTU and 1 copy | Relative Herbicide Tolerance[@] |
|---|---|---|---|---|---|---|
| 1 | 1580[1]-001 | 6 | + | | | Not tested |
| 2 | 1580[1]-002 | 8 | + | | | Not tested |
| 3 | 1580[1]-003 | 10 | + | | | Not tested |
| 4 | 1580[1]-004 | 1 | + | * | * | High |
| 5 | 1580[1]-005 | 2 | + | * | | Variable |
| 6 | 1580[1]-006 | 6 | + | | | Not tested |
| 7 | 1580[1]-007 | 4 | + | | | Not tested |
| 8 | 1580[1]-008 | 3 | + | | | Variable |
| 9 | 1580[1]-009 | 4 | + | | | Not tested |
| 10 | 1580[1]-010 | 8 | + | | | Not tested |
| 11 | 1580[1]-011 | 3 | + | | | High |
| 12 | 1580[1]-012 | 12 | + | | | Not tested |
| 13 | 1580[1]-013 | 13 | + | | | Not tested |
| 14 | 1580[1]-014 | 4 | + | | | Not tested |
| 15 | 1580[1]-015 | 2 | + | * | | High |
| 16 | 1580[1]-016 | 1 ? | + | * | * | High |
| 17 | 1580[1]-017 | 3 | + | | | High |
| 18 | 1580[1]-018 | 1 | + | * | * | Variable |
| 19 | 1580[1]-019 | 1 | + | * | * | Variable |
| 20 | 1580[1]-020 | 1 | + | * | * | Not tested |
| 21 | 1580[1]-021 | 1 | + | * | * | Not tested |
| 22 | 1580[1]-022 | 3 | + | | | Variable |
| 23 | 1580[1]-023 | 1 | + | * | * | Variable |
| 24 | 1580[1]-024 | 1 | + | * | * | Variable |
| 25 | 1580[1]-025 | 5 | + | | | Not tested |
| 26 | 1580[1]-026 | 3 | + | | | Variable |
| 27 | 1580[1]-027 | 3 | + | | | Low |
| 28 | 1580[1]-028 | 4 | + | | | Not tested |
| 29 | 1580[1]-029 | 3 | + | | | Variable |
| 30 | 1580[1]-030 | 1 | + | * | * | High |
| 31 | 1580[1]-031 | 1 | + | * | * | High |
| 32 | 1580[1]-032 | 2 | + | * | | High |

[@]Distinguishing herbicide tolerance performance of events required assessment of relative tolerance when treated with 560 g ae/ha fluroxypyr where tolerance was variable across events.

10.2 Verification of High 2,4-D Tolerance in $T_1$ Tobacco.

Two to four $T_0$ individuals surviving high rates of 2,4-D and fluroxypyr were saved from each event and allowed to self fertilize in the greenhouse to give rise to $T_1$ seed. The $T_1$ seed was stratified, and sown into selection trays much like that of *Arabidopsis* (Example 7.4), followed by selective removal of untransformed nulls in this segregating population with 560 g ai/ha glufosinate (PAT gene selection). Survivors were transferred to individual 3-inch pots in the greenhouse. These lines provided high levels of resistance to 2,4-D in the $T_0$ generation. Improved consistency of response is anticipated in $T_1$ plants not having come directly from tissue culture. These plants were compared against wildtype KY160 tobacco. All plants were sprayed with a track sprayer set at 187 L/ha. The plants were sprayed from a range of 140-2240 g ae/ha 2,4-D dimethylamine salt (DMA), 70-1120 g ae/ha triclopyr or 35-560 g ae/ha fluroxypyr. All applications were formulated in water. Each treatment was replicated 2-4 times. Plants were evaluated at 3 and 14 days after treatment. Plants were assigned injury rating with respect to stunting, chlorosis, and necrosis. The $T_1$ generation is segregating, so some variable response is expected due to difference in zygosity.

No injury was observed at 4× field rate (2240 g ae/ha) for 2,4-D or below. Some injury was observed with triclopyr treatments in one event line, but the greatest injury was observed with fluroxypyr. The fluroxypyr injury was short-lived and new growth on one event was nearly indistinguishable from the untreated control by 14 DAT (Table 21). It is important to note that untransformed tobacco is exceedingly sensitive to fluroxypyr. These results indicated commercial level 2,4-D tolerance can be provided by AAD-12 (v1), even in a very auxin-sensitive dicot crop like tobacco. These results also show resistance can be imparted to the pyridyloxyacetic acid herbicides, triclopyr and fluroxypyr. Having the ability to prescribe treatments in an herbicide tolerant crop protected by AAD-12 with various active ingredients having varying spectra of weed control is extremely useful to growers.

TABLE 21

Assessment of cross tolerance of AAD-12 (v1) $T_1$ tobacco plants' response to various phenoxy and pyridyloxy auxin herbicides.

| Herbicide | KY160-Wildtype | 1580(1)-004 (high tolerance in $T_0$ generation) | 1580(1)-018 (high tolerance in $T_0$ generation) |
|---|---|---|---|
| | Average % Injury of Replicates 14 DAT | | |
| 140 g ae/ha 2,4-D DMA | 45 | 0 | 0 |
| 560 g ae/ha 2,4-D DMA | 60 | 0 | 0 |
| 2240 g ae/ha 2,4-D DMA | 73 | 0 | 0 |
| 70 g ae/ha triclopyr | 40 | 0 | 5 |
| 280 g ae/ha triclopyr | 65 | 0 | 5 |
| 1120 g ae/ha triclopyr | 80 | 0 | 8 |
| 35 g ae/ha fluroxypyr | 85 | 0 | 8 |
| 140 g ae/ha fluroxypyr | 93 | 0 | 10 |
| 560 g ae/ha fluroxypyr | 100 | 3 | 18 |

10.3 AAD-12 (v1) Heritability in Tobacco

A 100 plant progeny test was also conducted on seven $T_1$ lines of AAD-12 (v1) lines. The seeds were stratified, sown, and transplanted with respect to the procedure above with the exception that null plants were not removed by Liberty selection. All plants were then sprayed with 560 g ae/ha 2,4-D DMA as previously described. After 14 DAT, resistant and sensitive plants were counted. Five out of the seven lines tested segregated as a single locus, dominant Mendelian trait (3R:1S) as determined by Chi square analysis. AAD-12 is heritable as a robust aryloxyalkanoate auxin resistance gene in multiple species.

10.4—Field Tolerance of pDAS1580 Tobacco Plants to 2,4-D, Dichloprop, Triclopyr and Fluroxypyr Herbicides.

Field level tolerance trials were conducted on three AAD-12 (v1) lines (events pDAS1580-[1]-018.001, pDAS1580-[1]-004.001 and pDAS1580-[1]-020.016) and one wild-type line (KY160) at field stations in Indiana and Mississippi. Tobacco transplants were grown in the greenhouse by planting $T_1$ seed in 72 well transplant flats (Hummert International) containing Metro 360 media according to growing conditions indicated above. The null plants were selectively removed by Liberty selection as previously described. The transplant plants were transported to the field stations and planted at either 14 or 24 inches apart using industrial vegetable planters. Drip irrigation at the Mississippi site and overhead irrigation at the Indiana site were used to keep plants growing vigorously.

The experimental design was a split plot design with 4 replications. The main plot was herbicide treatment and the sub-plot was tobacco line. The herbicide treatments were 2,4-D (dimethylamine salt) at 280, 560, 1120, 2240 and 4480 g ae/ha, triclopyr at 840 g ae/ha, fluroxypyr at 280 g ae/ha and an untreated control. Plots were one row by 25-30 ft. Herbicide treatments were applied 3-4 weeks after transplanting using compressed air backpack sprayer delivering 187 L/ha carrier volume at 130-200 kpa pressure. Visual rating of injury, growth inhibition, and epinasty were taken at 7, 14 and 21 days after treatment.

AAD-12 (v1) event response to 2,4-D, triclopyr, and fluroxypyr are shown in Table 22. The non-transformed tobacco line was severely injured (63% at 14 DAT) by 2,4-D at 560 g ae/ha which is considered the 1× field application rate. The AAD-12 (v1) lines all demonstrated excellent tolerance to 2,4-D at 14 DAT with average injury of 1, 4, and 4% injury observed at the 2, 4 and 8× rates, respectively. The non-transformed tobacco line was severely injured (53% at 14 DAT) by the 2× rate of triclopyr (840 g ae/ha); whereas, AAD-12 (v1) lines demonstrated tolerance with an average of 5% injury at 14 DAT across the three lines. Fluroxypyr at 280 g ae/ha caused severe injury (99%) to the non-transformed line at 14 DAT. AAD-12 (v1) lines demonstrated increased tolerance with an average of 11% injury at 14 DAT.

These results indicate that AAD-12 (v1) transformed event lines displayed a high level of tolerance to 2,4-D, triclopyr and fluroxypyr at multiples of commercial use rates that were lethal or caused severe epinastic malformations to non-transformed tobacco under representative field conditions.

TABLE 22

AAD-12 (v1) tobacco plants response to 2,4-D, triclopyr, and fluroxypyr under field conditions.

| Herbicide Treatment | | Average % Injury across locations at 14 DAT | | | |
|---|---|---|---|---|---|
| Active Ingredient | Rate | Wild type | pDAS1580-[1]-004.001 | pDAS1580-[1]-020.016 | pDAS1580-[1]-018.001 |
| 2,4-D | 280 GM AE/HA | 48 | 0 | 0 | 0 |
| 2,4-D | 560 GM AE/HA | 63 | 0 | 0 | 2 |
| 2,4-D | 1120 GM AE/HA | 78 | 1 | 1 | 2 |
| 2,4-D | 2240 GM AE/HA | 87 | 4 | 4 | 4 |
| 2,4-D | 4480 GM AE/HA | 92 | 4 | 4 | 4 |
| Triclopyr | 840 GM AE/HA | 53 | 5 | 5 | 4 |
| Fluroxypyr | 280 GM AE/HA | 99 | 11 | 11 | 12 |

10.5 AAD-12 (v1) Protection Against Elevated 2,4-D Rates

Results showing AAD-12 (v1) protection against elevated rates of 2,4-D DMA in the greenhouse are shown in Table 23. $T_1$ AAD-12 (v1) plants from an event segregating 3R:1S when selected with 560 g ai/ha Liberty using the same protocol as previously described. $T_1$ AAD-1 (v3) seed was also planted for transformed tobacco controls (see PCT/US2005/014737). Untransformed KY160 was served as the sensitive control. Plants were sprayed using a track sprayer set to 187 L/ha at 140, 560, 2240, 8960, and 35840 g ae/ha 2,4-D DMA and rated 3 and 14 DAT.

AAD-12 (v1) and AAD-1 (v3) both effectively protected tobacco against 2,4-D injury at doses up to 4× commercial use rates. AAD-12 (v1), however, clearly demonstrated a marked advantage over AAD-1 (v3) by protecting up to 64× the standard field rates.

TABLE 23

Results demonstrating protection provided by AAD-12 (v1) and AAD-1 (v3) against elevated rates of 2,4-D.

| Treatment | KY160 control | AAD-1 (v3) | AAD-12 (v1) |
|---|---|---|---|
| | Average % injury 14 DAT | | |
| 2240 g ae/ha 2,4-D | 95 | 4 | 0 |
| 8960 g ae/ha 2,4-D | 99 | 9 | 0 |
| 35840 g ae/ha 2,4-D | 100 | 32 | 4 |

10.6 Stacking of AAD-12 to Increase Herbicide Spectrum

Homozygous AAD-12 (v1) (pDAS1580) and AAD-1 (v3) (pDAB721) plants (see PCT/US2005/014737 for the latter) were both reciprocally crossed and $F_1$ seed was collected. The $F_1$ seed from two reciprocal crosses of each gene were stratified and treated 4 reps of each cross were treated under the same spray regimine as used for the other testing with one of the following treatments: 70, 140, 280 g ae/ha fluroxypyr (selective for the AAD-12 (v1) gene); 280, 560, 1120 g ae/ha R-dichloroprop (selective for the AAD-1 (v3) gene); or 560, 1120, 2240 g ae/ha 2,4-D DMA (to confirm 2,4-D tolerance). Homozygous $T_2$ plants of each gene were also planted for use as controls. Plants were graded at 3 and 14 DAT. Spray results are shown in Table 24.

The results confirm that AAD-12 (v1) can be successfully stacked with AAD-1 (v3), thus increasing the spectrum of herbicides that may be applied to the crop of interest (phenoxyactetic acids+phenoxypropionic acids vs penoxyacetic acids+pyridyloxyacetic acids for AAD-1 and AAD-12, respectively). The complementary nature of herbicide cross resistance patterns allows convenient use of these two genes as complementary and stackable field-selectable markers. In crops where tolerance with a single gene may be marginal, one skilled in the art recognizes that one can increase tolerance by stacking a second tolerance gene for the same herbicide. Such can be done using the same gene with the same or different promoters; however, as observed here, stacking and tracking two complementary traits can be facilitated by the distinguishing cross protection to phenoxypropionic acids [from AAD-1 (v3)] or pyidyloxyacetic acids [AAD-12 (v1)]

TABLE 24

Comparison of auxinic herbicide cross tolerance of AAD-12 (v1) (pDAS1580) and AAD-1 (v3) (pDAB721) T$_2$ plants compared to AAD-12 × AAD-1 F1 cross and to wildtype.

| Treatment | KY160 wildtype control | AAD-12 (v1) (pDAS1580) | AAD-1(v3) (pDAB721) | AAD-12 (v1) × AAD (v3) F$_1$ |
|---|---|---|---|---|
| | | Average % injury 14 DAT | | |
| 560 g ae/ha 2,4-D | 63 | 0 | 0 | 0 |
| 1120 g ae/ha 2,4-D | 80 | 0 | 4 | 0 |
| 2240 g ae/ha 2,4-D | 90 | 0 | 9 | 0 |
| 280 g ae/ha R-dichlorprop | 25 | 15 | 0 | 0 |
| 560 g ae/ha R-dichlorprop | 60 | 50 | 0 | 0 |
| 1120 g ae/ha R-dichlorprop | 80 | 70 | 3 | 0 |
| 70 g ae/ha fluroxypyr | 40 | 0 | 40 | 0 |
| 140 g ae/ha fluroxypyr | 65 | 0 | 60 | 0 |
| 280 g ae/ha fluroxypyr | 75 | 3 | 75 | 3 |

Example 11—Soybean Transformation

Soybean improvement via gene transfer techniques has been accomplished for such traits as herbicide tolerance (Padgette et al., 1995), amino acid modification (Falco et al., 1995), and insect resistance (Parrott et al., 1994). Introduction of foreign traits into crop species requires methods that will allow for routine production of transgenic lines using selectable marker sequences, containing simple inserts. The transgenes should be inherited as a single functional locus in order to simplify breeding. Delivery of foreign genes into cultivated soybean by microprojectile bombardment of zygotic embryo axes (McCabe et al., 1988) or somatic embryogenic cultures (Finer and McMullen, 1991), and Agrobacterium-mediated transformation of cotyledonary explants (Hinchee et al., 1988) or zygotic embryos (Chee et al., 1989) have been reported.

Transformants derived from Agrobacterium-mediated transformations tend to possess simple inserts with low copy number (Birch, 1991). There are benefits and disadvantages associated with each of the three target tissues investigated for gene transfer into soybean, zygotic embryonic axis (Chee et al., 1989; McCabe et al., 1988), cotyledon (Hinchee et al., 1988) and somatic embryogenic cultures (Finer and McMullen, 1991). The latter has been extensively investigated as a target tissue for direct gene transfer. Embryogenic cultures tend to be quite prolific and can be maintained over a prolonged period. However, sterility and chromosomal aberrations of the primary transformants have been associated with age of the embryogenic suspensions (Singh et al., 1998) and thus continuous initiation of new cultures appears to be necessary for soybean transformation systems utilizing this tissue. This system needs a high level of 2,4-D, 40 mg/L concentration, to initiate the embryogenic callus and this poses a fundamental problem in using the AAD-12 (v1) gene since the transformed locus could not be developed further with 2,4-D in the medium. So, the meristem based transformation is ideal for the development of 2,4-D resistant plant using AAD-12 (v1).

11.1 Gateway Cloning of Binary Constructs

The AAD-12 (v1) coding sequence was cloned into five different Gateway Donor vectors containing different plant promoters. The resulting AAD-12 (v1) plant expression cassettes were subsequently cloned into a Gateway Destination Binary vector via the LR Clonase reaction (Invitrogen Corporation, Carlsbad Ca, Cat #11791-019).

An NcoI-SacI fragment containing the AAD-12 (v1) coding sequence was digested from DASPICO12 and ligated into corresponding NcoI-SacI restriction sites within the following Gateway Donor vectors: pDAB3912 (attL1//CsVMV promoter//AtuORF23 3'UTR//attL2); pDAB3916 (attL1//AtUbi10 promoter//AtuORF23 3'UTR//attL2); pDAB4458 (attL1//AtUbi3 promoter//AtuORF23 3'UTR//attL2); pDAB4459 (attL1//ZmUbi1 promoter//AtuORF23 3'UTR//attL2); and pDAB4460 (attL1//AtAct2 promoter//AtuORF23 3'UTR//attL2). The resulting constructs containing the following plant expression cassettes were designated: pDAB4463 (attL1//CsVMV promoter//AAD-12 (v1)//AtuORF23 3'UTR//attL2); pDAB4467 (attL1//AtUbi10 promoter//AAD-12 (v1)//AtuORF23 3'UTR//attL2); pDAB4471 (attL1//AtUbi3 promoter//AAD-12 (v1)//AtuORF23 3'UTR//attL2); pDAB4475 (attL1//ZmUbi1 promoter//AAD-12 (v1)//AtuORF23 3'UTR//attL2); and pDAB4479 (attL1//AtAct2 promoter//AAD-12 (v1)//AtuORF23 3'UTR//attL2). These constructs were confirmed via restriction enzyme digestion and sequencing.

The plant expression cassettes were recombined into the Gateway Destination Binary vector pDAB4484 (RB7 MARv3//attR1-ccdB-chloramphenicol resistance-attR2//CsVMV promoter//PATv6//AtuORF1 3'UTR) via the Gateway LR Clonase reaction. Gateway Technology uses lambda phage-based site-specific recombination instead of restriction endonuclease and ligase to insert a gene of interest into an expression vector. Invitrogen Corporation, Gateway Technology: A Universal Technology to Clone DNA Sequences for Functional Analysis and Expression in multiple Systems, Technical Manual, Catalog #'s 12535-019 and 12535-027, Gateway Technology Version E, Sep. 22, 2003, #25-022. The DNA recombination sequences (attL, and attR,) and the LR Clonase enzyme mixture allows any DNA fragment flanked by a recombination site to be transferred into any vector containing a corresponding site. The attL1 site of the donor vector corresponds with attR1 of the binary vector. Likewise, the attL2 site of the donor vector corresponds with attR2 of the binary vector. Using the Gateway Technology the plant expression cassette (from the donor vector) which is flanked by the attL sites can be recombined into the attR sites of the binary vector. The resulting constructs containing the following plant expression cassettes were labeled as: pDAB4464 (RB7 MARv3//CsVMV promoter//AAD-12 (v1)//AtuORF23 3'UTR//CsVMV promoter//PATv6//AtuORF1 3'UTR); pDAB4468 (RB7 MARv3//AtUbi10 promoter//AAD-12 (v1)//AtuORF23 3'UTR//CsVMV promoter//PATv6//AtuORF1 3'UTR); pDAB4472 (RB7 MARv3//AtUbi3 promoter//AAD-12 (v1)//AtuORF23 3'UTR//CsVMV promoter//

PATv6//AtuORF1 3'UTR); pDAB4476 (RB7 MARv3// ZmUbi1 promoter//AAD-12 (v1)//AtuORF23 3'UTR// CsVMV promoter//PATv6//AtuORF1 3'UTR); and pDAB4480 (RB7 MARv3//AtAct2 promoter//AAD-12 (v1)//AtuORF23 3'UTR//CsVMV promoter//PATv6//AtuORF1 3'UTR) (see Table 8). These constructs were confirmed via restriction enzyme digestion and sequencing.

11.2 Transformation Method 1: Cotyledonary Node Transformation of Soybean Mediated by *Agrobacterium tumefaciens*.

The first reports of soybean transformation targeted meristematic cells in the cotyledonary node region (Hinchee et al., 1988) and shoot multiplication from apical meristems (McCabe et al., 1988). In the *A. tumefaciens*-based cotyledonary node method, explant preparation and culture media composition stimulate proliferation of auxiliary meristems in the node (Hinchee et al., 1988). It remains unclear whether a truly dedifferentiated, but totipotent, callus culture is initiated by these treatments. The recovery of multiple clones of a transformation event from a single explant and the infrequent recovery of chimeric plants (Clemente et al., 2000; Olhoft et al., 2003) indicates a single cell origin followed by multiplication of the transgenic cell to produce either a proliferating transgenic meristem culture or a uniformly transformed shoot that undergoes further shoot multiplication. The soybean shoot multiplication method, originally based on microprojectile bombardment (McCabe et al., 1988) and, more recently, adapted for *Agrobacterium*-mediated transformation (Martinell et al., 2002), apparently does not undergo the same level or type of dedifferentiation as the cotyledonary node method because the system is based on successful identification of germ line chimeras. The range of genotypes that have been transformed via the *Agrobacterium*-based cotyledonary node method is steadily growing (Olhoft and Somers, 2001). This de novo meristem and shoot multiplication method is less limited to specific genotypes. Also, this is a non 2,4-D based protocol which would be ideal for 2,4-D selection system. Thus, the cotyledonary node method may be the method of choice to develop 2,4-D resistant soybean cultivars. Though this method was described as early as 1988 (Hinchee et al., 1988), only very recently has it been optimized for routine high frequency transformation of several soybean genotypes (Zhang et al., 1999; Zeng et al., 2004).

11.2.1—Plant Transformation Production of AAD-12 (v1) Tolerant Phenotypes.

Seed derived explants of "Maverick" and the *Agrobacterium* mediated cot-node transformation protocol was used to produce AAD-12 (v1) transgenic plants.

11.2.2—*Agrobacterium* Preparation and Inoculation

*Agrobacterium* strain EHA101 (Hood et al. 1986), carrying each of five binary pDAB vectors (Table 8) was used to initiate transformation. Each binary vector contains the AAD-12 (v1) gene and a plant-selectable gene (PAT) cassette within the T-DNA region. Each gene is driven by the promoters listed in Table 8 and these plasmids were mobilized into the EHA101 strain of *Agrobacterium* by electroporation. The selected colonies were then analyzed for the integration of genes before the *Agrobacterium* treatment of the soybean explants. Maverick seeds were used in all transformation experiments and the seeds were obtained from University of Missouri, Columbia, Mo.

*Agrobacterium*-mediated transformation of soybean (*Glycine max*) using the PAT gene as a selectable marker coupled with the herbicide glufosinate as a selective agent was carried out followed a modified procedure of Zeng et al. (2004). The seeds were germinated on B5 basal medium (Gamborg et al. 1968) solidified with 3 g/L Phytagel (Sigma-Aldrich, St. Louis, Mo.); added 1-cysteine to the co-cultivation medium at 400 mg/L and co-cultivation lasted 5 days (Olhoft and Somers 2001); shoot initiation, shoot elongation, and rooting media were supplemented with 50 mg/L cefotaxime, 50 mg/L timentin, 50 mg/L vancomycin, and solidified with 3 g/L Phytagel. Selected shoots were then transferred to the rooting medium. The optimal selection scheme was the use of glufosinate at 8 mg/L across the first and second shoot initiation stages in the medium and 3-4 mg/L during shoot elongation in the medium.

Prior to transferring elongated shoots (3-5 cm) to rooting medium, the excised end of the internodes were dipped in 1 mg/L indole 3-butyric acid for 1-3 min to promote rooting (Khan et al. 1994). The shoots struck roots in 25×100 mm glass culture tubes containing rooting medium and then they were transferred to soil mix for acclimatization of plantlets in Metro-mix 200 (Hummert International, Earth City, Mo.) in open Magenta boxes in Convirons. Glufosinate, the active ingredient of Liberty herbicide (Bayer Crop Science), was used for selection during shoot initiation and elongation. The rooted plantlets were acclimated in open Magenta boxes for several weeks before they were screened and transferred to the greenhouse for further acclimation and establishment.

11.2.3—Assay of Putatively Transformed Plantlets, and Analyses Established $T_0$ Plants in the Greenhouse.

The terminal leaflets of selected leaves of these plantlets were leaf painted with 50 mg/L of glufosinate twice with a week interval to observe the results to screen for putative transformants. The screened plantlets were then transferred to the greenhouse and after acclimation the leaves were painted with glufosinate again to confirm the tolerance status of these plantlets in the GH and deemed to be putative transformants.

Plants that are transferred to the greenhouse can be assayed for the presence of an active PAT gene further with a non-destructive manner by painting a section of leaf of the $T_0$ primary transformant, or progeny thereof, with a glufosinate solution [0.05-2% v/v Liberty Herbicide, preferably 0.25-1.0% (v/v), =500-2000 ppm glufosinate, Bayer Crop Science]. Depending on the concentration used, assessment for glufosinate injury can be made 1-7 days after treatment. Plants can also be tested for 2,4-D tolerance in a non-destructive manner by selective application of a 2,4-D solution in water (0.25-1% v/v commercial 2,4-D dimethylamine salt formulation, preferably 0.5% v/v=2280 ppm 2,4-D ae) to the terminal leaflet of the newly expanding trifoliolate one or two, preferably two, nodes below the youngest emerging trifolioate. This assay allows assessment of 2,4-D sensitive plants 6 hours to several days after application by assessment of leaf flipping or rotation >90 degrees from the plane of the adjacent leaflets. Plants tolerant to 2,4-D will not respond to 2,4-D. $T_0$ plants will be allowed to self fertilize in the greenhouse to give rise to $T_1$ seed. $T_1$ plants (and to the extent enough $T_0$ plant clones are produced) will be sprayed with a range of herbicide doses to determine the level of herbicide protection afforded by AAD-12 (v1) and PAT genes in transgenic soybean. Rates of 2,4-D used on $T_0$ plants will typically comprise one or two selective rates in the range of 100-1120 g ae/ha using a track sprayer as previously described. $T_1$ plants will be treated with a wider herbicide dose ranging from 50-3200 g ae/ha 2,4-D. Likewise, $T_0$ and $T_1$ plants can be screened for glufosinate resistance by postemergence treatment with 200-800 and 50-3200 g ae/ha glufosinate, respectively. Glyphosate resistance (in plants transformed with constructs that contain EPSPS) or another glyphosate tolerance gene can be assessed in the $T_1$ generation by postemergence applications of glyphosate with a dose range from 280-2240 g ae/ha glyphosate. Analysis of protein expression will occur as described in below. Individual $T_0$ plants were assessed for the presence of the coding region of the gene of interest (AAD-12 (v1) or PAT v6) and copy number. Determination of the inheritance of AAD-12 (v1) will be made using $T_1$ and $T_2$ progeny segregation with respect to herbicide tolerance as described in previous examples.

A subset of the initial transformants were assessed in the $T_0$ generation according to the methods above. Any plant confirmed as having the AAD-12 (v1) coding region, regardless of the promoter driving the gene did not respond to the 2,4-D leaf painting whereas wildtype Maverick soybeans did (Table Sec 11.2.3). PAT-only transformed plants responded the same at wildtype plants to leaf paint applications of 2,4-D 2,4-D was applied to a subset of the plants that were of similar size to the wildtype control plants with either 560 or 1120 g ae 2,4-D. All AAD-12 (v1)-containing plants were clearly resistant to the herbicide application versus the wildtype Maverick soybeans. A slight level of injury (2 DAT) was observed for two AAD-12 (v1) plants, however, injury was temporary and no injury was observed 7 DAT. Wildtype control plants were severely injured 7-14 DAT at 560 g ae/ha 2,4-D and killed at 1120 g ae/ha. These data are consistent with the fact that AAD-12 (v1) can impart high tolerance (>2x field rates) to a sensitive crop like soybeans. The screened plants were then sampled for molecular and biochemical analyses for the confirmation of the AAD12 (v1) genes integration, copy number, and their gene expression levels as described below and reported in Table 25.

11.2.4—Molecular Analyses: Soybean 11.2.4.1—Tissue Harvesting DNA Isolation and Quantification.

Fresh tissue is placed into tubes and lyophilized at 4° C. for 2 days. After the tissue is fully dried, a tungsten bead (Valenite) is placed in the tube and the samples are subjected to 1 minute of dry grinding using a Kelco bead mill. The standard DNeasy DNA isolation procedure is then followed (Qiagen, DNeasy 69109). An aliquot of the extracted DNA is then stained with Pico Green (Molecular Probes P7589) and read in the fluorometer (BioTek) with known standards to obtain the concentration in ng/µL.

11.2.4.2—Polymerase Chain Reaction.

A total of 100 ng of total DNA is used as the template. 20 mM of each primer is used with the Takara Ex Taq PCR Polymerase kit (Mirus TAKRR001A). Primers for the AAD-12 (v1) PTU are (Forward-ATAATGCCAGC CTGT-TAAACGCC) (SEQ ID NO:8) and (Reverse-CT-CAAGCATATGAATGACCT CGA) (SEQ ID NO:9). The PCR reaction is carried out in the 9700 Geneamp thermocycler (Applied Biosystems), by subjecting the samples to 94° C. for 3 minutes and 35 cycles of 94° C. for 30 seconds, 63° C. for 30 seconds, and 72° C. for 1 minute and 45 seconds followed by 72° C. for 10 minutes. Primers for Coding Region PCR AAD-12 (v1) are (Forward-ATGGCT-CATGCTGCCCTCAGCC) (SEQ ID NO:10) and (Reverse-CGGGC AGGCCTAACTCCACCAA) (SEQ ID NO: 11). The PCR reaction is carried out in the 9700 Geneamp thermocycler (Applied Biosystems), by subjecting the samples to 94° C. for 3 minutes and 35 cycles of 94° C. for 30 seconds, 65° C. for 30 seconds, and 72° C. for 1 minute

TABLE 25

$T_0$ soybean response to 2,4-D leaf paint and 2,4-D spray application.

| | | | | Leaf flip assay NODE 2,4-D @ (18 HAT) | | | | | | | | | |
|---|---|---|---|---|---|---|---|---|---|---|---|---|---|
| Construct | | | | LEAF PAINT- | Node | | Spray POST over the top with 2,4-D | Stage at appl (# | ELISA] | Southern Copy | PCR coding | % injury 2 | % injury 7 | % injury 14 |
| (pDAB#) | Gene | Promoter | Event | ED | N-1 | N-2 | (g ae/ha) | nodes) | (ng/ML) | Number | region | DAT | DAT | DAT |
| 4464 | AAD-12 | CsVMV | D-1-14 | N-1 | 0 | | 0 | >10 | 5246.83 | 2 | + | X | X | 0 |
| 4464 | AAD-12 | CsVMV | D-2-9 | N-2 | | 0 | 0 | >10 | 204.27 | 1 | + | X | X | 0 |
| 4468 | AAD-12 | AtUbi10 | D-3-7 | N-2 | | 0 | 0 | >10 | 4.65 | 1 | + | 0 | 0 | 0 |
| 4468 | AAD-12 | AtUbi10 | D-4-11B | N-2 | | 0 | 0 | 8 | 1452.84 | 2 | + | 0 | 0 | 0 |
| 4468 | AAD-12 | AtUbi10 | D-4-16 | N-2 | | 0 | 0 | >10 | 653.21 | 2 | + | X | X | 0 |
| 4480 | AAD-12 | AtAct2 | D-9-1 | N-2 | | 0 | 0 | >10 | 248.33 | 3 or 4 | + | X | X | 0 |
| 4464 | AAD-12 | CsVMV | D-2-14 | N-2 | | 0 | 560 | 7 | 4917.43 | 2 | + | 0 | 0 | 0 |
| 4468 | AAD-12 | AtUbi10 | D-3-5 | N-2 | | 0 | 560 | 8 | 365.75 | 1 | + | 0 | 0 | 0 |
| 4468 | AAD-12 | AtUbi10 | D-3-6 | N-1 | 0 | | 560 | 5 | 714.79 | 3 | + | 0 | 0 | 0 |
| 4472 | AAD-12 | AtUbi3 | D-5-2 | N-1 | 0 | | 560 | 6 | 0.58 | 1 | + | 5 | 0 | 0 |
| 4468 | AAD-12 | AtUbi10 | D-3-9 | N-2 | | 0 | 1120 | 6 | 2657.26 | 3 | + | 0 | 0 | 0 |
| 4468 | AAD-12 | AtUbi10 | D-4-17 | N-2 | | 0 | 1120 | 7 | 286.14 | 5 | + | 5 | 0 | 0 |
| 4499 | PAT | CsVMV | D-2-3 | N-2 | 1 | | 0 | >10 | 2.36 | 5 | + | X | X | 0 |
| Maverick | WT | | WT-10 | NT | 1 | | ND | ND | ND | ND | ND | ND | ND | ND |
| Maverick | WT | | WT-2 | NT | 1 | | ND | ND | ND | ND | ND | ND | ND | ND |
| Maverick | WT | | WT-3 | NT | | | 0 | 4 | ND | ND | ND | 0 | 0 | 0 |
| Maverick | WT | | WT-4 | NT | | | 0 | 4 | ND | ND | ND | 0 | 0 | 0 |
| Maverick | WT | | WT-5 | NT | | | 560 | 4 | ND | ND | ND | 50 | 60 | 60 |
| Maverick | WT | | WT-6 | NT | | | 560 | 4 | ND | ND | ND | 70 | 90 | 80 |
| Maverick | WT | | WT-7 | NT | | | 560 | 4 | ND | ND | ND | 70 | 80 | 80 |
| Maverick | WT | | WT-10 | NT | | | 1120 | 4 | ND | ND | ND | 70 | 90 | 100 |
| Maverick | WT | | WT-8 | NT | | | 1120 | 4 | ND | ND | ND | 70 | 95 | 100 |
| Maverick | WT | | WT-9 | NT | | | 1120 | 4 | ND | ND | ND | 70 | 95 | 100 |

1 = Flip 0 = No Flip
ND = Not determined and 45 seconds followed by 72° C. for 10 minutes. PCR products are analyzed by electrophoresis on a 1% agarose gel stained with EtBr.

11.2.4.3—Southern Blot Analysis.

Southern blot analysis is performed with total DNA obtained from Qiagen DNeasy kit. A total of 10 µg of genomic DNA is subjected to an overnight digestion to obtain integration data. After the overnight digestion an aliquot of ~100 ng is run on a 1% gel to ensure complete digestion. After this assurance the samples are run on a large 0.85% agarose gel overnight at 40 volts. The gel is then denatured in 0.2 M NaOH, 0.6 M NaCl for 30 minutes. The gel is then neutralized in 0.5 M Tris HCl, 1.5 M NaCl pH of 7.5 for 30 minutes. A gel apparatus containing 20×SSC is then set up to obtain a gravity gel to nylon membrane (Millipore INYC00010) transfer overnight. After the overnight transfer the membrane is then subjected to UV light via a crosslinker (Stratagene UV stratalinker 1800) at 1200×100 microjoules. The membrane is then washed in 0.1% SDS, 0.1 SSC for 45 minutes. After the 45 minute wash, the membrane is baked for 3 hours at 80° C. and then stored at 4° C. until hybridization. The hybridization template fragment is prepared using the above coding region PCR using plasmid DNA. The product is run on a 1% agarose gel and excised and then gel extracted using the Qiagen (28706) gel extraction procedure. The membrane is then subjected to a pre-hybridization at 60° C. step for 1 hour in Perfect Hyb buffer (Sigma H7033). The Prime it RmT dCTP-labeling rxn (Stratagene 300392) procedure is used to develop the p32 based probe (Perkin Elmer). The probe is cleaned up using the Probe Quant. G50 columns (Amersham 27-5335-01). Two million counts CPM are used to hybridize the southern blots overnight. After the overnight hybridization the blots are then subjected to two 20 minute washes at 65° C. in 0.1% SDS, 0.1 SSC. The blots are then exposed to film overnight, incubating at −80° C.

11.2.5—Biochemical Analyses: Soybean 11.2.5.1—Tissue Sampling and Extracting AAD-12 (v1) Protein from Soybean Leaves.

Approximately 50 to 100 mg of leaf tissue was sampled from the N-2 leaves that were 2,4-D leaf painted, but after 1 DAT. The terminal N-2 leaflet was removed and either cut into small pieces or 2-single-hole-punched leaf discs (~0).5 cm in diameter) and were frozen on dry ice instantly. Further protein analysis (ELISA and Western analysis) was completed according to methods described in Example 9.

11.2.6—$T_1$ Progeny Evaluation.

$T_0$ plants will be allowed to self fertilize to derive $T_1$ families. Progeny testing (segregation analysis) will be assayed using glufosinate at 560 g ai/ha as the selection agent applied at the V1-V2 growth stage. Surving plants will be further assayed for 2,4-D tolerance at one or more growth stages from V2-V6. Seed will be produced through self fertilization to allow broader herbicide testing on the transgenic soybean.

AAD-12 (v1) transgenic Maverick soybean plants have been generated through *Agrobacterium*-mediated cot-node transformation system. The $T_0$ plants obtained tolerated up to 2× levels of 2,4-D field applications and developed fertile seeds. The frequency of fertile transgenic soybean plants was up to 5.9%. The integration of the AAD1-12 (v1) gene into the soybean genome was confirmed by Southern blot analysis. This analysis indicated that most of the transgenic plants contained a low copy number. The plants screened with AAD-12 (v1) antibodies showed positive for ELISA and the appropriate band in Western analysis.

11.3 Transformation Method 2: Aerosol-Beam Mediated Transformation of Embryogenic Soybean Callus Tissue.

Culture of embryogenic soybean callus tissue and subsequent beaming can be accomplished as described in U.S. Pat. No. 6,809,232 (Held et al.) to create transformants using one or more constructs in Table 8.

11.4 Transformation Method 3. Biolistic Bombardment of Soybean

This can be accomplished using mature seed derived embryonic axes meristem (McCabe et al. (1988)). Following established methods of biolistic bombardment, one can expect recovery of transformed soybean plants. Once plants are regenerated and evaluation of events could occur as described in Example 11.2.

11.5 Transformation Method 4. Whiskers Mediated Transformation.

Whisker preparation and whisker transformation can anticipated according to methods described previously by Terakawa et al. (2005)). Following established methods of biolistic bombardment, one can expect recovery of transformed soybean plants. Once plants are regenerated and evaluation of events could occur as described in Example 11.2.

Maverick seeds were surface-sterilized in 70% ethanol for 1 min followed by immersion in 1% sodium hypochlorite for 20 min. and then rinsed three times in sterile distilled water. The seeds were soaked in distilled water for 18-20 h. The embryonic axes were excised from seeds, and the apical meristems were exposed by removing the primary leaves. The embryonic axes were positioned in the bombardment medium [BM: MS (Murashige and Skoog 1962) basal salts medium, 3% sucrose and 0.8% phytagel Sigma, pH 5.7] with the apical region directed upwards in 5-cm culture dishes containing 12 ml culture medium.

11.6 Transformation Method 5.

Particle bombardment-mediated transformation for embryogenic callus tissue can be optimized for according to previous methods (Khalafalla et al., 2005; El-Shemy et al., 2004, 2006). Regenerated plants can also be assessed according to Example 11.2.

Example 12—AAD-12 (v1) in Cotton 12.1—Cotton Transformation Protocol.

Cotton seeds (Co310 genotype) are surface-sterilized in 95% ethanol for 1 minute, rinsed, sterilized with 50% commercial bleach for twenty minutes, and then rinsed 3 times with sterile distilled water before being germinated on G-media (Table 26) in Magenta GA-7 vessels and maintained under high light intensity of 40-60 µE/m2, with the photoperiod set at 16 hours of light and 8 hours dark at 28° C.

Cotyledon segments (~5 mm) square are isolated from 7-10 day old seedlings into liquid M liquid media (Table 26) in Petri plates (Nunc, item #0875728). Cut segments are treated with an *Agrobacterium* solution (for 30 minutes) then transferred to semi-solid M-media (Table 26) and undergo co-cultivation for 2-3 days. Following co-cultivation, segments are transferred to MG media (Table 26). Carbenicillin is the antibiotic used to kill the *Agrobacterium* and glufosinate-ammonium is the selection agent that would allow growth of only those cells that contain the transferred gene.

*Agrobacterium* Preparation.

Inoculate 35 ml of Y media (Table 26) (containing streptomycin (100 mg/ml stock) and erythromycin (100 mg/ml stock)), with one loop of bacteria to grow overnight in the dark at 28° C., while shaking at 150 rpm. The next day, pour the *Agrobacterium* solution into a sterile oakridge tube (Nalge-Nunc, 3139-0050), and centrifuge for in Beckman J2-21 at 8,000 rpm for 5 minutes. Pour off the supernatant and resuspend the pellet in 25 ml of M liquid (Table 26) and vortex. Place an aliquot into a glass culture tube (Fisher, 14-961-27) for Klett reading (Klett-Summerson, model 800-

Larger, well-developed embryos are isolated and transferred to DK media (Table 26) for embryo development. After 3 weeks (or when the embryos have developed), germinated embryos are transferred to fresh media for shoot and root development. After 4-8 weeks, any well-developed plants are transferred into soil and grown to maturity. Following a couple of months, the plant has grown to a point that it can be sprayed to determine if it has resistance to 2,4-D.

TABLE 26

Media for Cotton Transformation

| Ingredients in 1 liter | G | M liquid | M | MG | D | DK | Y |
|---|---|---|---|---|---|---|---|
| LS Salts (5x) | 200 ml | 200 ml | 200 ml | 200 ml | | | |
| Glucose | | 30 grams | 30 grams | 30 grams | 20 grams | | |
| modified B5 vit (1000x) | 1 ml | 1 ml | 1 ml | 1 ml | 10 ml | 1 ml | |
| kinetin (1 mM) | | 1 ml | 1 ml | 1 ml | | 0.5 ml | |
| 2,4-D (1 mM) | | 1 ml | 1 ml | 1 ml | | | |
| Agar | 8 grams | | 8 grams | 8 grams | 8 grams | 8 grams | |
| DKW salts (D190) | | | | | 1 package | 1 package | |
| MYO-Inositol (100x) | | | | | 1 ml | 10 ml | |
| Sucrose 3% | 30 grams | | | | | 30 grams | 10 grams |
| NAA | | | | | | | |
| Carbenicillin (250 mg/ml) | | | | 2 ml | | | |
| GLA (10 mg/ml) | | | | 0.5 ml | | | |
| Peptone | | | | | | | 10 grams |
| Yeast Extract | | | | | | | 10 grams |
| NaCl | | | | | | | 5 grams |

3). Dilute the new suspension using M liquid media to a Klett-meter reading of $10^8$ colony forming units per ml with a total volume of 40 ml.

After three weeks, callus from the cotyledon segments is isolated and transferred to fresh MG media. The callus is transferred for an additional 3 weeks on MG media. In a side-by-side comparison, MG media can be supplemented with dichlorprop (added to the media at a concentration of 0.01 and 0.05 mg/L) to supplement for the degradation of the 2,4-D, since dichlorprop is not a substrate for to the AAD-12 enzyme, however dichlorprop is more active on cotton than 2,4-D. In a separate comparison, segments which were plated on MG media containing no growth regulator compared to standard MG media, showed reduced callusing, but there still is callus growth. Callus is then transferred to CG-media (Table 26), and transferred again to fresh selection medium after three weeks. After another three weeks the callus tissue is transferred to D media (Table 26) lacking plant growth regulators for embryogenic callus induction. After 4-8 weeks on this media, embryogenic callus is formed, and can be distinguished from the non-embryogenic callus by its yellowish-white color and granular cells. Embryos start to regenerate soon after and are distinct green in color. Cotton can take time to regenerate and form embryos, one of the ways to speed up this process is to stress the tissue. Dessication is a common way to accomplish this, via changes in the microenvironment of the tissue and plate, by using less culture media and/or adopting various modes of plate enclosure (taping versus parafilm).

12.2—Cell Transformation.

7 Several experiments were initiated in which cotyledon segments were treated with *Agrobacterium* containing pDAB724. Over 2000 of the resulting segments were treated using various auxin options for the proliferation of pDAB724 cotton callus, either: 0.1 or 0.5 mg/L R-dichlorprop, standard 2,4-D concentration and no auxin treatment. The callus was selected on glufosinate-ammonium, due to the inclusion of the PAT gene in the construct. Callus line analysis in the form of PCR and Invader will be used to determine if and to be sure the gene was present at the callus stage; then callus lines that are embryogenic will be sent for Western analysis, essentially as described in section 11.2.3. Embryogenic cotton callus was stressed using dessication techniques to improve the quality and quantity of the tissue recovered.

Almost 200 callus events have been screened for intact PTU and expression using Western analysis for the AAD-12 (v1) gene. Below is a subset of the data for some of the cotton callus that has been tested.

TABLE 26.b

| Construct | Line Number | AAD-12 PTU | AAD-12 Invader | AAD-12 ng/ml |
|---|---|---|---|---|
| pDAB724 | 1 | + | + | 79.89 |
| pDAB724 | 2 | + | + | 17.34 |
| pDAB724 | 3 | + | + | 544.80 |

TABLE 26.b-continued

| Construct | Line Number | AAD-12 PTU | AAD-12 Invader | AAD-12 ng/ml |
|---|---|---|---|---|
| pDAB724 | 4 | + | + | 32.63 |
| pDAB724 | 5 | + | + | 82.77 |
| pDAB724 | 83 | + | + | 795.50 |
| pDAB724 | 84 | + | + | 613.35 |
| pDAB724 | 85 | + | + | 1077.75 |
| pDAB724 | 86 | + | + | 437.74 |
| pDAB724 | 87 | + | + | 286.51 |
| pDAB724 | 88 | + | + | 517.59 |
| pDAB724 | 89 | + | + | 1250.70 |

12.3—Plant Regeneration.

AAD-12 (v1) cotton lines that have produced plants according to the above protocol will be sent to the greenhouse. To demonstrate the AAD-12 (v1) gene provides resistance to 2,4-D in cotton, both the AAD-12 (v1) cotton plant and wild-type cotton plants will be sprayed with a track sprayer delivering 560 g ae/ha 2,4-D at a spray volume of 187 L/ha. The plants will be evaluated at 3 and 14 days after treatment. Plants surviving a selective rate of 2,4-D will be self pollinated to create $T_1$ seed or outcrossed with an elite cotton line to produce $F_1$ seed. The subsequent seed produced will be planted and evaluated for herbicide resistance as previously described. AAD-12 (v1) events can be combined with other desired HT or IR trants as described in experiments 18, 19, 22, and 23.

Example 13—Agrobacterium Transformation of Other Crops

In light of the subject disclosure, additional crops can be transformed according to the subject invention using techniques that are known in the art. For *Agrobacterium*-mediated trans-formation of rye, see, e.g., Popelka and Altpeter (2003). For *Agrobacterium*-mediated transformation of soybean, see, e.g., Hinchee et al., 1988. For *Agrobacterium*-mediated transformation of sorghum, see, e.g., Zhao et al., 2000. For *Agrobacterium*-mediated transformation of barley, see, e.g., Tingay et al., 1997. For *Agrobacterium*-mediated transformation of wheat, see, e.g., Cheng et al., 1997. For *Agrobacterium*-mediated transformation of rice, see, e.g., Hiei et al., 1997.

The Latin names for these and other plants are given below. It should be clear that these and other (non-*Agrobacterium*) transformation techniques can be used to transform AAD-12 (v1), for example, into these and other plants, including but not limited to Maize (*Zea mays*), Wheat (*Triticum* spp.), Rice (*Oryza* spp. and *Zizania* spp.), Barley (*Hordeum* spp.), Cotton (*Abroma augusta* and *Gossypium* spp.), Soybean (*Glycine max*), Sugar and table beets (*Beta* spp.), Sugar cane (*Arenga pinnata*), Tomato (*Lycopersicon esculentum* and other spp., *Physalis ixocarpa*, *Solanum incanum* and other spp., and *Cyphomandra betacea*), Potato (*Solanum tubersoum*), Sweet potato (*Ipomoea betatas*), Rye (*Secale* spp.), Peppers (*Capsicum annuum*, *sinense*, and *frutescens*), Lettuce (*Lactuca sativa*, *perennis*, and *pulchella*), Cabbage (*Brassica* spp), Celery (*Apium graveolens*), Eggplant (*Solanum melongena*), Peanut (*Arachis hypogea*), Sorghum (all *Sorghum* species), Alfalfa (*Medicago sativua*), Carrot (*Daucus carota*), Beans (*Phaseolus* spp. and other genera), Oats (*Avena sativa* and *strigosa*), Peas (*Pisum*, *Vigna*, and *Tetragonolobus* spp.), Sunflower (*Helianthus annuus*), Squash (*Cucurbita* spp.), Cucumber (*Cucumis sativa*), Tobacco (*Nicotiana* spp.), Arabidopsis (*Arabidopsis thaliana*), Turfgrass (*Lolium*, *Agrostis*, *Poa*, *Cynadon*, and other genera), Clover (*Tifolium*), Vetch (*Vicia*). Such plants, with AAD-12 (v1) genes, for example, are included in the subject invention.

AAD-12 (v1) has the potential to increase the applicability of key auxinic herbicides for in-season use in many deciduous and evergreen timber cropping systems. Triclopyr, 2,4-D, and/or fluroxypyr resistant timber species would increase the flexibility of over-the-top use of these herbicides without injury concerns. These species would include, but not limited to: Alder (*Alnus* spp.), ash (*Fraxinus* spp.), aspen and poplar species (*Populus* spp.), beech (*Fagus* spp.), birch (*Betula* spp.), cherry (*Prunus* spp.), eucalyptus (*Eucalyptus* spp.), hickory (*Carya* spp.), maple (*Acer* spp.), oak (*Quercus* spp), and pine (*Pinus* spp). Use of auxin resistance for the selective weed control in ornamental and fruit-bearing species is also within the scope of this invention. Examples could include, but not be limited to, rose (*Rosa* spp.), burning bush (*Euonymus* spp.), petunia (*Petunia* spp), begonia (*Begonia* spp.), rhododendron (*Rhododendron* spp), crabapple or apple (*Malus* spp.), pear (*Pyrus* spp.), peach (*Prunus* spp) and marigolds (*Tagetes* spp.).

Example 14—Further Evidence of Surprising Results: AAD-12 vs. AAD-2

14.1—AAD-2 (v1) Initial Cloning.

Another gene was identified from the NCBI database (see the ncbi.nlm.nih.gov website; accession #AP005940) as a homologue with only 44% amino acid identity to tfdA. This gene is referred to herein as AAD-2 (v1) for consistency. Percent identity was determined by first translating both the AAD-2 and tfdA DNA sequences (SEQ ID NO:12 of PCT/US2005/014737 and GENBANK Accession No. M16730, respectively) to proteins (SEQ ID NO:13 of PCT/US2005/014737 and GENBANK Accession No. M16730, respectively), then using ClustalW in the VectorNTI software package to perform the multiple sequence alignment.

The strain of *Bradyrhizobium japonicum* containing the AAD-2 (v1) gene was obtained from Northern Regional Research Laboratory (NRRL, strain #B4450). The lyophilized strain was revived according to NRRL protocol and stored at −80° C. in 20% glycerol for internal use as Dow Bacterial strain DB 663. From this freezer stock, a plate of Tryptic Soy Agar was then struck out with a loopful of cells for isolation, and incubated at 28° C. for 3 days. A single colony was used to inoculate 100 ml of Tryptic Soy Broth in a 500 ml tri-baffled flask, which was incubated overnight at 28° C. on a floor shaker at 150 rpm. From this, total DNA was isolated with the gram negative protocol of Qiagen's DNeasy kit (Qiagen cat. #69504). The following primers were designed to amplify the target gene from genomic DNA, Forward (SEQI ID NO:16): 5' ACT AGT AAC AAA GAA GGA GAT ATA CCA TGA CGA T 3' [(brjap 5'(speI) SEQ ID NO:14 of PCT/US2005/014737 (added Spe I restriction site and Ribosome Binding Site (RBS))] and Reverse (SEQ ID NO:17): 5' TTC TCG AGC TAT CAC TCC GCC GCC TGC TGC TGC 3' [(brjap 3' (xhoI) SEQ ID NO:15 of PCT/US2005/014737 (added a Xho I site)].

Fifty microliter reactions were set up as follows: Fail Safe Buffer 25 µl, ea. primer 1 µl (50 ng/µl), gDNA 1 µl (200 ng/µl), H₂O 21 µl, Taq polymerase 1 µl (2.5 units/µl). Three Fail Safe Buffers—A, B, and C—were used in three separate reactions. PCR was then carried out under the following conditions: 95° C. 3.0 minutes heat denature cycle; 95° C. 1.0 minute, 50° C. 1.0 minute, 72° C. 1.5 minutes, for 30 cycles; followed by a final cycle of 72° C. 5 minutes, using the FailSafe PCR System (Epicenter cat. #FS99100). The resulting ~1 kb PCR product was cloned into pCR 2.1 (Invitrogen cat. #K4550-40) following the included protocol, with chemically competent TOP10F' *E. coli* as the host strain, for verification of nucleotide sequence.

Ten of the resulting white colonies were picked into 3 µl Luria Broth+1000 µg/ml Ampicillin (LB Amp), and grown overnight at 37° C. with agitation. Plasmids were purified from each culture using Nucleospin Plus Plasmid Miniprep Kit (BD Biosciences cat. #K3063-2) and following included protocol. Restriction digestion of the isolated DNA's was completed to confirm the presence of the PCR product in the pCR2.1 vector. Plasmid DNA was digested with the restriction enzyme EcoRI (New England Biolabs cat. #R0101S). Sequencing was carried out with Beckman CEQ Quick Start Kit (Beckman Coulter cat. #608120) using M13 Forward [5' GTA AAA CGA CGG CCA G 3'](SEQ ID NO:6) and Reverse [5' CAG GAA ACA GCT ATG AC 3'](SEQ ID NO:7) primers, per manufacturers instructions. This gene sequence and its corresponding protein was given a new general designation AAD-2 (v1) for internal consistency.

14.2—Completion of AAD-2 (v1) Binary Vector.

The AAD-2 (v1) gene was PCR amplified from pDAB3202. During the PCR reaction alterations were made within the primers to introduce the AflIII and SacI restriction sites in the 5' primer and 3' primer, respectively. See PCT/US2005/014737. The primers "NcoI of Brady" [5' TAT ACC ACA TGT CGA TCG CCA TCC GGC AGC TT 3'](SEQ ID NO:14) and "SacI of Brady" [5' GAG CTC CTA TCA CTC CGC CGC CTG CTG CTG CAC 3'](SEQ ID NO:15) were used to amplify a DNA fragment using the Fail Safe PCR System (Epicentre). The PCR product was cloned into the pCR2.1 TOPO TA cloning vector (Invitrogen) and sequence verified with M13 Forward and M13 Reverse primers using the Beckman Coulter "Dye Terminator Cycle Sequencing with Quick Start Kit" sequencing reagents. Sequence data identified a clone with the correct sequence (pDAB716). The AflIII/SacI AAD-2 (v1) gene fragment was then cloned into the NcoI/SacI pDAB726 vector. The resulting construct (pDAB717); AtUbi10 promoter: Nt OSM 5'UTR: AAD-2 (v1): Nt OSM3'UTR: ORF1 polyA 3'UTR was verified with restriction digests (with NcoI/SacI). This construct was cloned into the binary pDAB3038 as a NotI-NotI DNA fragment. The resulting construct (pDAB767); AtUbi10 promoter: Nt OSM5'UTR: AAD-2 (v1): Nt OSM 3'UTR: ORF1 polyA 3'UTR: CsVMV promoter PAT: ORF25/26 3'UTR was restriction digested (with NotI, EcoRI, HinDIII, NcoI, PvuII, and SalI) for verification of the correct orientation. The completed construct (pDAB767) was then used for transformation into *Agrobacterium*.

14.3—Evaluation of Transformed *Arabidopsis*.

Freshly harvested $T_1$ seed transformed with a plant optimized AAD-12 (v1) or native AAD-2 (v1) gene were planted and selected for resistance to glufosinate as previously described Plants were then randomly assigned to various rates of 2,4-D (50-3200 g ae/ha). Herbicide applications were applied by track sprayer in a 187 L/ha spray volume. 2,4-D used was the commercial dimethylamine salt formulation (456 g ae/L, NuFarm, St Joseph, Mo.) mixed in 200 mM Tris buffer (pH 9.0) or 200 mM HEPES buffer (pH7.5).

AAD-12 (v1) and AAD-2 (v1) did provide detectable 2,4-D resistance versus the transformed and untransformed control lines; however, individual constructs were widely variable in their ability to impart 2,4-D resistance to individual $T_1$ *Arabidopsis* plants. Surprisingly, AAD-2 (v1) and AAD-2 (v2) transformants were far less resistant to 2,4-D than the AAD-12 (v1) gene, both from a frequency of highly tolerant plants as well as overall average injury. No plants transformed with AAD-2 (v1) survived 200 g ae/ha 2,4-D relatively uninjured (<20% visual injury), and overall population injury was about 83% (see PCT/US2005/014737). Conversely, AAD-12 (v1) had a population injury average of about 6% when treated with 3,200 g ae/ha 2,4-D (Table 11). Tolerance improved slightly for plant-optimized AAD-2 (v2) versus the native gene; however, comparison of both AAD-12 and AAD-2 plant optimized genes indicates a significant advantage for AAD-12 (v1) in planta.

These results are unexpected given that the in vitro comparison of AAD-2 (v1) (see PCT/US2005/014737) and AAD-12 (v2) indicated both were highly efficacious at degrading 2,4-D and both shared an S-type specificity with respect to chiral aryloxyalkanoate substrates. AAD-2 (v1) is expressed in individual $T_1$ plants to varying levels; however, little protection from 2,4-D injury is afforded by this expressed protein. No substantial difference was evident in protein expression level (in planta) for the native and plant optimized AAD-2 genes (see PCT/US2005/014737). These data corroborate earlier findings that make the functional expression of AAD-12 (v1) in planta, and resulting herbicide resistance to 2,4-D and pyridyloxyacetate herbicides, unexpected.

Example 15—Preplant Burndown Applications

This and the following Examples are specific examples of novel herbicide uses made possible by the subject AAD-12 invention.

Preplant burndown herbicide applications are intended to kill weeds that have emerged over winter or early spring prior to planting a given crop. Typically these applications are applied in no-till or reduced tillage management systems where physical removal of weeds is not completed prior to planting. An herbicide program, therefore, must control a very wide spectrum of broadleaf and grass weeds present at the time of planting. Glyphosate, gramoxone, and glufosinate are examples of non-selective, non-residual herbicides widely used for preplant burndown herbicide applications. Some weeds, however, are difficult to control at this time of the season due to one or more of the following: inherent insensitivity of the weed species or biotype to the herbicide, relatively large size of winter annual weeds, and cool weather conditions limiting herbicide uptake and activity. Several herbicide options are available to tankmix with these herbicides to increase spectrum and activity on weeds where the non-selective herbicides are weak. An example would be 2,4-D tankmix applications with glyphosate to assist in the control of *Conyza canadensis* (horseweed). Glyphosate can be used from 420 to 1680 g ae/ha, more typically 560 to 840 g ae/ha, for the preplant burndown control of most weeds present; however, 280-1120 g ae/ha of 2,4-D can be applied to aid in control of many broadleaf weed species (e.g., horseweed). 2,4-D is an herbicide of choice because it is effective on a very wide range of broadleaf weeds, effective even at low temperatures, and extremely inexpensive. However, if the subsequent crop is a sensitive dicot crop, 2,4-D residues in the soil (although short-lived) can negatively impact the crop. Soybeans are a sensitive crop and require a minimum time period of 7 days (for 280 g ae/ha 2,4-D rate) to at least 30 days (for 2,4-D applications of 1120 g ae/ha) to occur between burndown applications and planting. 2,4-D is prohibited as a burndown treatment prior to cotton planting (see federal labels, most are available through CPR, 2005 or online at cdms.net/manuf/manuf.asp). With AAD- 12 (v1) transformed cotton or soybeans, these crops should be able to survive 2,4-D residues in the soil from burndown applications applied right up to and even after planting before emergence of the crop. The increased flexibility and reduced cost of tankmix (or commercial premix) partners will improve weed control options and increase the robustness of burndown applications in important no-till and reduced tillage situations. This example is one of many options that will be available. Those skilled in the art of weed control will note a variety of other applications including, but not limited to gramoxone+2,4-D or glufosinate+2, 4-D by utilizing products described in federal herbicide labels (CPR, 2005) and uses described in Agriliance Crop Protection Guide (2005), as examples. Those skilled in the art will also recognize that the above example can be applied to any 2,4-D-sensitive (or other phenoxy auxin herbicide) crop that would be protected by the AAD-12 (v1) gene if stably transformed. Likewise, the unique attributes of AAD-12 allowing degradation of triclopyr and fluroxypyr increase utility by allowing substitution or tank mixes of 70-1120 or 35-560 g ae/ha of triclopyr and fluroxypyr, respectively, to increase spectrum and/or increase the ability to control perennial or viney weed species.

Example 16—In-Crop Use of Phenoxy Auxins Herbicides in Soybeans, Cotton, and Other Dicot Crops Transformed Only with AAD-12 (v1)

AAD-12 (v1) can enable the use of phenoxy auxin herbicides (e.g., 2,4-D and MCPA) and pyridyloxy auxins (triclopyr and fluroxypyr) for the control of a wide spectrum of broadleaf weeds directly in crops normally sensitive to 2,4-D. Application of 2,4-D at 280 to 2240 g ae/ha would control most broadleaf weed species present in agronomic environments. More typically, 560-1120 g ae/ha is used. For triclopyr, application rates would typically range from 70-1120 g ae/ha, more typically 140-420 g ae/ha. For fluroxypyr, application rates would typically range from 35-560 g ae/ha, more typically 70-280 ae/ha.

An advantage to this additional tool is the extremely low cost of the broadleaf herbicide component and potential short-lived residual weed control provided by higher rates of 2,4-D, triclopyr, and fluroxypyr when used at higher rates, whereas a non-residual herbicide like glyphosate would provide no control of later germinating weeds. This tool also provides a mechanism to combine herbicide modes of action with the convenience of HTC as an integrated herbicide resistance and weed shift management strategy.

A further advantage this tool provides is the ability to tankmix broad spectrum broadleaf weed control herbicides (e.g., 2,4-D, triclopyr and fluroxypyr) with commonly used residual weed control herbicides. These herbicides are typically applied prior to or at planting, but often are less effective on emerged, established weeds that may exist in the field prior to planting. By extending the utility of these aryloxy auxin herbicides to include at-plant, preemergence, or pre-plant applications, the flexibility of residual weed control programs increases. One skilled in the art would recognize the residual herbicide program will differ based on the crop of interest, but typical programs would include herbicides of the chloracetmide and dinitroaniline herbicide families, but also including herbicides such as clomazone, sulfentrazone, and a variety of ALS-inhibiting PPO-inhibiting, and HPPD-inhibiting herbicides.

Further benefits could include tolerance to 2,4-D, triclopyr or fluroxypyr required before planting following aryloxyacetic acid auxin herbicide application (see previous example); and fewer problems from contamination injury to dicot crops resulting from incompletely cleaned bulk tanks that had contained 2,4-D, triclopyr or fluroxypyr. Dicamba (and many other herbicides) can still be used for the subsequent control of AAD-12 (v1)-transformed dicot crop volunteers.

Those skilled in the art will also recognize that the above example can be applied to any 2,4-D-sensitive (or other aryloxy auxin herbicide) crop that would be protected by the AAD-12 (v1) gene if stably transformed. One skilled in the art of weed control will now recognize that use of various commercial phenoxy or pyridyloxy auxin herbicides alone or in combination with a herbicide is enabled by AAD-12 (v1) transformation. Specific rates of other herbicides representative of these chemistries can be determined by the herbicide labels compiled in the CPR (Crop Protection Reference) book or similar compilation or any commercial or academic crop protection references such as the Crop Protection Guide from Agriliance (2005). Each alternative herbicide enabled for use in HTCs by AAD-12 (v1), whether used alone, tank mixed, or sequentially, is considered within the scope of this invention.

Example 17—In-Crop Use of Phenoxy Auxin and Pyridyloxy Auxin Herbicides in AAD-12 (v1) Only Transformed Corn, Rice, and Other Monocot Species In an analogous fashion, transformation of grass species (such as, but not limited to, corn, rice, wheat, barley, or turf and pasture grasses) with AAD-12 (v1) would allow the use of highly efficacious phenoxy and pyridyloxy auxins in crops where normally selectivity is not certain. Most grass species have a natural tolerance to auxinic herbicides such as the phenoxy auxins (i.e., 2,4-D,). However, a relatively low level of crop selectivity has resulted in diminished utility in these crops due to a shortened window of application timing or unacceptable injury risk. AAD-12 (v1)-transformed monocot crops would, therefore, enable the use of a similar combination of treatments described for dicot crops such as the application of 2,4-D at 280 to 2240 g ae/ha to control most broadleaf weed species. More typically, 560-1120 g ae/ha is used. For triclopyr, application rates would typically range from 70-1120 g ae/ha, more typically 140-420 g ae/ha. For fluroxypyr, application rates would typically range from 35-560 g ae/ha, more typically 70-280 ae/ha.

An advantage to this additional tool is the extremely low cost of the broadleaf herbicide component and potential short-lived residual weed control provided by higher rates of 2,4-D, triclopyr, or fluroxypyr. In contrast, a non-residual herbicide like glyphosate would provide no control of later-germinating weeds. This tool would also provide a mechanism to rotate herbicide modes of action with the convenience of HTC as an integrated-herbicide-resistance and weed-shift-management strategy in a glyphosate tolerant crop/AAD-12 (v1) HTC combination strategy, whether one rotates crops species or not.

A further advantage this tool provides is the ability to tankmix broad spectrum broadleaf weed control herbicides (e.g., 2,4-D, triclopyr and fluroxypyr) with commonly used residual weed control herbicides. These herbicides are typically applied prior to or at planting, but often are less effective on emerged, established weeds that may exist in the field prior to planting. By extending the utility of these aryloxy auxin herbicides to include at-plant, preemergence, or pre-plant applications, the flexibility of residual weed control programs increases. One skilled in the art would recognize the residual herbicide program will differ based on the crop of interest, but typical programs would include herbicides of the chloracetmide and dinitroaniline herbicide families, but also including herbicides such as clomazone, sulfentrazone, and a variety of ALS-inhibiting PPO-inhibiting, and HPPD-inhibiting herbicides.

The increased tolerance of corn, rice, and other monocots to the phenoxy or pyridyloxy auxins shall enable use of these herbicides in-crop without growth stage restrictions or the potential for crop leaning, unfurling phenomena such as "rat-tailing," crop leaning, growth regulator-induced stalk brittleness in corn, or deformed brace roots. Each alternative herbicide enabled for use in HTCs by AAD-12 (v1), whether used alone, tank mixed, or sequentially, is considered within the scope of this invention.

Example 18—AAD-12 (v1) Stacked With Glyphosate Tolerance Trait in Any Crop

The vast majority of cotton, canola, corn, and soybean acres planted in North America contain a glyphosate tolerance (GT) trait, and adoption of GT corn is on the rise. Additional GT crops (e.g., wheat, rice, sugar beet, and turf) have been under development but have not been commercially released to date. Many other glyphosate resistant species are in experimental to development stage (e.g., alfalfa, sugar cane, sunflower, beets, peas, carrot, cucumber, lettuce, onion, strawberry, tomato, and tobacco; forestry species like poplar and sweetgum; and horticultural species like marigold, *petunia*, and begonias; isb.vt.edu/cfdocs/ fieldtests1.cfm, 2005 on the World Wide Web). GTC's are valuable tools for the sheer breadth of weeds controlled and convenience and cost effectiveness provided by this system. However, glyphosate's utility as a now-standard base treatment is selecting for glyphosate resistant weeds. Furthermore, weeds that glyphosate is inherently less efficacious on are shifting to the predominant species in fields where glyphosate-only chemical programs are being practiced. By stacking AAD-12 (v1) with a GT trait, either through conventional breeding or jointly as a novel transformation event, weed control efficacy, flexibility, and ability to manage weed shifts and herbicide resistance development could be improved. As mentioned in previous examples, by transforming crops with AAD-12 (v1), monocot crops will have a higher margin of phenoxy or pyridyloxy auxin safety, and phenoxy auxins can be selectively applied in dicot crops. Several scenarios for improved weed control options can be envisioned where AAD-12 (v1) and a GT trait are stacked in any monocot or dicot crop species:
  a) Glyphosate can be applied at a standard postemergent application rate (420 to 2160 g ae/ha, preferably 560 to 840 g ae/ha) for the control of most grass and broadleaf weed species. For the control of glyphosate resistant broadleaf weeds like *Conyza canadensis* or weeds inherently difficult to control with glyphosate (e.g., *Commelina* spp, *Ipomoea* spp, etc), 280-2240 g ae/ha (preferably 560-1120 g ae/ha) 2,4-D can be applied sequentially, tank mixed, or as a premix with glyphosate to provide effective control. For triclopyr, application rates would typically range from 70-1120 g ae/ha, more typically 140-420 g ae/ha. For fluroxypyr, application rates would typically range from 35-560 g ae/ha, more typically 70-280 ae/ha.
  b) Currently, glyphosate rates applied in GTC's generally range from 560 to 2240 g ae/ha per application timing. Glyphosate is far more efficacious on grass species than broadleaf weed species. AAD-12 (v1)+GT stacked traits would allow grass-effective rates of glyphosate (105-840 g ae/ha, more preferably 210-420 g ae/ha). 2,4-D (at 280-2240 g ae/ha, more preferably 560-1120 g ae/ha) could then be applied sequentially, tank mixed, or as a premix with grass-effective rates of glyphosate to provide necessary broadleaf weed control. Tricopyr and fluroxypyr at rates mentioned above would be acceptable components in the treatment regimin. The low rate of glyphosate would also provide some benefit to the broadleaf weed control; however, primary control would be from the 2,4-D, triclopyr, or fluroxypyr.

One skilled in the art of weed control will recognize that use of one or more commercial aryloxy auxin herbicides alone or in combination (sequentially or independently) is enabled by AAD-12 (v1) transformation into crops. Specific rates of other herbicides representative of these chemistries can be determined by the herbicide labels compiled in the CPR (Crop Protection Reference) book or similar compilation, labels compiled online (e.g., cdms.net/manuf/manuf.asp), or any commercial or academic crop protection guides such as the Crop Protection Guide from Agriliance (2005). Each alternative herbicide enabled for use in HTCs by AAD-12 (v1), whether used alone, tank mixed, or sequentially, is considered within the scope of this invention.

Example 19—AAD-12 (v1) Stacked with Glufosinate Tolerance Trait in any Crop

Glufosinate tolerance (PAT or bar) is currently present in a number of crops planted in North America either as a selectable marker for an input trait like insect resistance proteins or specifically as an HTC trait. Crops include, but are not limited to, glufosinate tolerant canola, corn, and cotton. Additional glufosinate tolerant crops (e.g., rice, sugar beet, soybeans, and turf) have been under development but have not been commercially released to date. Glufosinate, like glyphosate, is a relatively non-selective, broad spectrum grass and broadleaf herbicide. Glufosinate's mode of action differs from glyphosate. It is faster acting, resulting in desiccation and "burning" of treated leaves 24-48 hours after herbicide application. This is advantageous for the appearance of rapid weed control. However, this also limits translocation of glufosinate to meristematic regions of target plants resulting in poorer weed control as evidenced by relative weed control performance ratings of the two compounds in many species (Agriliance, 2005).

By stacking AAD-12 (v1) with a glufosinate tolerance trait, either through conventional breeding or jointly as a novel transformation event, weed control efficacy, flexibility, and ability to manage weed shifts and herbicide resistance development could be improved. Several scenarios for improved weed control options can be envisioned where AAD-12 (v1) and a glufosinate tolerance trait are stacked in any monocot or dicot crop species:
  a) Glufosinate can be applied at a standard postemergent application rate (200 to 1700 g ae/ha, preferably 350 to 500 g ae/ha) for the control of many grass and broadleaf weed species. To date, no glufosinate-resistant weeds have been confirmed; however, glufosinate has a greater number of weeds that are inherently more tolerant than does glyphosate.
    i) Inherently tolerant broadleaf weed species (e.g., *Cirsium arvensis Apocynum cannabinum*, and *Conyza canadensis*) could be controlled by tank mixing 280-2240 g ae/ha, more preferably 560-2240 g ae/ha, 2,4-D for effective control of these more difficult-to-control perennial species and to improve the robustness of control on annual broadleaf weed species. Triclopyr and fluroxypyr would be acceptable components to consider in the weed control regimen. For triclopyr, application rates would typically range from 70-1120 g ae/ha, more typically 140-420 g ae/ha. For fluroxypyr, application rates would typically range from 35-560 g ae/ha, more typically 70-280 ae/ha.

b) A multiple combination of glufosinate (200-500 g ae/ha)+/−2,4-D (280-1120 g ae/ha)+/−triclopyr or fluroxypyr (at rates listed above), for example, could provide more robust, overlapping weed control spectrum. Additionally, the overlapping spectrum provides an additional mechanism for the management or delay of herbicide resistant weeds.

One skilled in the art of weed control will recognize that use of one or more commercial aryloxyacetic auxin herbicides alone or in combination (sequentially or independently) is enabled by AAD-12 (v1) transformation into crops. Specific rates of other herbicides representative of these chemistries can be determined by the herbicide labels compiled in the CPR (Crop Protection Reference) book or similar compilation, labels compiled online (e.g., cdms.net/manuf/manuf.asp), or any commercial or academic crop protection guides such as the Crop Protection Guide from Agriliance (2005). Each alternative herbicide enabled for use in HTCs by AAD-12 (v1), whether used alone, tank mixed, or sequentially, is considered within the scope of this invention.

Example 20—AAD-12 (v1) Stacked with AHAS Trait in any Crop

Imidazolinone herbicide tolerance (AHAS, et al.) is currently present in a number of crops planted in North America including, but not limited to, corn, rice, and wheat. Additional imidazolinone tolerant crops (e.g., cotton and sugar beet) have been under development but have not been commercially released to date. Many imidazolinone herbicides (e.g., imazamox, imazethapyr, imazaquin, and imazapic) are currently used selectively in various conventional crops. The use of imazethapyr, imazamox, and the non-selective imazapyr has been enabled through imidazolinone tolerance traits like AHAS et al. This chemistry class also has significant soil residual activity, thus being able to provide weed control extended beyond the application timing, unlike glyphosate or glufosinate-based systems. However, the spectrum of weeds controlled by imidazolinone herbicides is not as broad as glyphosate (Agriliance, 2005). Additionally, imidazolinone herbicides have a mode of action (inhibition of acetolactate synthase, ALS) to which many weeds have developed resistance (Heap, 2005). By stacking AAD-12 (v1) with an imidazolinone tolerance trait, either through conventional breeding or jointly as a novel transformation event, weed control efficacy, flexibility, and ability to manage weed shifts and herbicide resistance development could be improved. As mentioned in previous examples, by transforming crops with AAD-12 (v1), monocot crops will have a higher margin of phenoxy or pyridyloxy auxin safety, and these auxins can be selectively applied in dicot crops. Several scenarios for improved weed control options can be envisioned where AAD-12 (v1) and an imidazolinone tolerance trait are stacked in any monocot or dicot crop species:

a) Imazethapyr can be applied at a standard postemergent application rate of (35 to 280 g ae/ha, preferably 70-140 g ae/ha) for the control of many grass and broadleaf weed species.
  i) ALS-inhibitor resistant broadleaf weeds like *Amaranthus rudis*, *Ambrosia trifida*, *Chenopodium album* (among others, Heap, 2005) could be controlled by tank mixing 280-2240 g ae/ha, more preferably 560-1120 g ae/ha, 2,4-D. For triclopyr, application rates would typically range from 70-1120 g ae/ha, more typically 140-420 g ae/ha. For fluroxypyr, application rates would typically range from 35-560 g ae/ha, more typically 70-280 ae/ha.
  ii) Inherently more tolerant broadleaf species to imidazolinone herbicides like *Ipomoea* spp. can also be controlled by tank mixing 280-2240 g ae/ha, more preferably 560-1120 g ae/ha, 2,4-D. See rates above for triclopyr or fluroxypyr.
b) A multiple combination of imazethapyr (35 to 280 g ae/ha, preferably 70-140 g ae/ha)+/−2,4-D (280-1120 g ae/ha)+/−triclopyr or fluroxypyr (at rates listed above), for example, could provide more robust, overlapping weed control spectrum. Additionally, the overlapping spectrum provides an additional mechanism for the management or delay of herbicide resistant weeds.

One skilled in the art of weed control will recognize that use of any of various commercial imidazolinone herbicides, phenoxyacetic or pyridyloxyacetic auxin herbicides, alone or in multiple combinations, is enabled by AAD-12 (v1) transformation and stacking with any imidazolinone tolerance trait either by conventional breeding or genetic engineering. Specific rates of other herbicides representative of these chemistries can be determined by the herbicide labels compiled in the CPR (Crop Protection Reference) book or similar compilation, labels compiled online (e.g., cdms.net/manuf/manuf.asp), or any commercial or academic crop protection guides such as the Crop Protection Guide from Agriliance (2005). Each alternative herbicide enabled for use in HTCs by AAD-12 (v1), whether used alone, tank mixed, or sequentially, is considered within the scope of this invention.

Example 21—AAD-12 (v1) in Rice 21.1—Media Description.

Culture media employed were adjusted to pH 5.8 with 1 M KOH and solidified with 2.5 g/L Phytagel (Sigma). Embryogenic calli were cultured in 100×20 mm Petri dishes containing 40 ml semi-solid medium. Rice plantlets were grown on 50 ml medium in Magenta boxes. Cell suspensions were maintained in 125-ml conical flasks containing 35 ml liquid medium and rotated at 125 rpm. Induction and maintenance of embryogenic cultures took place in the dark at 25-26° C., and plant regeneration and whole-plant culture took place in a 16-h photoperiod (Zhang et al. 1996).

Induction and maintenance of embryogenic callus took place on NB basal medium as described previously (Li et al. 1993), but adapted to contain 500 mg/L glutamine. Suspension cultures were initiated and maintained in SZ liquid medium (Zhang et al. 1998) with the inclusion of 30 g/L sucrose in place of maltose. Osmotic medium (NBO) consisted of NB medium with the addition of 0.256 M each of mannitol and sorbitol. Hygromycin-B-resistant callus was selected on NB medium supplemented with 50 mg/L hygromycin B for 3-4 weeks. Pre-regeneration took place on medium (PRH50) consisting of NB medium without 2,4-dichlorophenoxyacetic acid (2,4-D), but with the addition of 2 mg/L 6-benzylaminopurine (BAP), 1 mg/L α-naphthaleneacetic acid (NAA), 5 mg/L abscisic acid (ABA) and 50 mg/L hygromycin B for 1 week. Regeneration of plantlets followed via culture on regeneration medium (RNH50) comprising NB medium without 2,4-D, and supplemented with 3 mg/L BAP, 0.5 mg/L NAA, and 50 mg/L hygromycin B until shoots regenerated. Shoots were transferred to rooting medium with half-strength Murashige and Skoog basal salts and Gamborg's B5 vitamins, supplemented with 1% sucrose and 50 mg/L hygromycin B (½MSH50).

21.2—Tissue Culture Development.

Mature desiccated seeds of Oryza sativa L. japonica cv. Taipei 309 were sterilized as described in Zhang et al. 1996. Embryogenic tissues were induced by culturing sterile mature rice seeds on NB medium in the dark. The primary callus approximately 1 mm in diameter, was removed from the scutellum and used to initiate cell suspension in SZ liquid medium. Suspensions were then maintained as described in Zhang 1995. Suspension-derived embryogenic tissues were removed from liquid culture 3-5 days after the previous subculture and placed on NBO osmotic medium to form a circle about 2.5 cm across in a Petri dish and cultured for 4 h prior to bombardment. Sixteen to 20 h after bombardment, tissues were transferred from NBO medium onto NBH50 hygromycin B selection medium, ensuring that the bombarded surface was facing upward, and incubated in the dark for 14-17 days. Newly formed callus was then separated from the original bombarded explants and placed nearby on the same medium. Following an additional 8-12 days, relatively compact, opaque callus was visually identified, and transferred to PRH50 pre-regeneration medium for 7 days in the dark. Growing callus, which became more compact and opaque was then subcultured onto RNH50 regeneration medium for a period of 14-21 days under a 16-h photoperiod. Regenerating shoots were transferred to Magenta boxes containing ½ MSH50 medium. Multiple plants regenerated from a single explant are considered siblings and were treated as one independent plant line. A plant was scored as positive for the hph gene if it produced thick, white roots and grew vigorously on ½ MSH50 medium. Once plantlets had reached the top of Magenta boxes, they were transferred to soil in a 6-cm pot under 100% humidity for a week, then moved to a growth chamber with a 14-h light period at 30° C. and in the dark at 21° C. for 2-3 weeks before transplanting into 13-cm pots in the greenhouse. Seeds were collected and dried at 37° C. for one week. prior to storage.

21.3—Microprojectile Bombardment.

All bombardments were conducted with the Biolistic PDS-1000/He™ system (Bio-Rad, Laboratories, Inc.). Three milligrams of 1.0 micron diameter gold particles were washed once with 100% ethanol, twice with sterile distilled water and resuspended in 50 µl water in a siliconized Eppendorf tube. Five micrograms plasmid DNA representing a 1:6 molar ratio of pDOW3303(Hpt-containing vector) to pDAB4101 (AAD-12 (v1)+AHAS), 20 µl spermidine (0.1 M) and 50 µl calcium chloride (2.5 M) were added to the gold suspension. The mixture was incubated at room temperature for 10 min, pelleted at 10000 rpm for 10 s, resuspended in 60 µl cold 100% ethanol and 8-9 µl was distributed onto each macrocarrier. Tissue samples were bombarded at 1100 psi and 27 in of Hg vacuum as described by Zhang et al. (1996).

21.4—Postemergence Herbicide Tolerance in AAD-12 (v1) Transformed to Rice

Rice plantlets at the 3-5 leaf stage were sprayed with a lethal dose of 0.16% (v/v) solution of Pursuit (to confirm the presence of the AHAS gene) containing 1% Sunit II (v/v) and 1.25% UAN (v/v) using a track sprayer calibrated to 187 L/ha. Rating for sensitivity or resistance was performed at 36 days after treatment (DAT). Ten of the 33 events sent to the greenhouse were robustly tolerant to the Pursuit; others suffered varying levels of herbicide injury. Plants were sampled (according to section 21.7 below) and molecular characterization was performed as previously described in Example 8 that identified seven of these 10 events as containing both the AAD-12 (v1) PTU and the entire AHAS coding region.

21.5—Heritability of AAD-12 (v1) in $T_1$ Rice

A 100-plant progeny test was conducted on five $T_1$ lines of AAD-12 (v1) lines that contained both the AAD-12 (v1) PTU and AHAS coding region. The seeds were planted with respect to the procedure above and sprayed with 140 g ae/ha imazethapyr using a track sprayer as previously described. After 14 DAT, resistant and sensitive plants were counted. Two out of the five lines tested segregated as a single locus, dominant Mendelian trait (3R:1S) as determined by Chi square analysis. AAD-12 cosegregated with the AHAS selectable marker as determined by 2,4-D tolerance testing below.

21.6—Verification of High 2,4-D Tolerance in $T_1$ Rice.

The following $T_1$ AAD-12 (v1) single segregating locus lines were planted into 3-inch pots containing Metro Mix media: pDAB4101(20)003 and pDAB4101(27)002. At 2-3 leaf stage were sprayed with 140 g ae/ha imazethapyr. Nulls were eliminated and individuals were sprayed at V3-V4 stage in the track sprayer set to 187 L/ha at 1120, 2240 or 4480 g ae/ha 2,4-D DMA (2×, 4×, and 8× typical commercial use rates, respectively). Plants were graded at 7 and 14 DAT and compared to untransformed commercial rice cultivar, 'Lamont,' as negative control plants.

Injury data (Table 27) shows that the AAD-12 (v1)-transformed lines are more tolerant to high rates of 2,4-D DMA than the untransformed controls. The line pDAB4101(20)003 was more tolerant to high levels of 2,4-D than the line pDAB4101(27)002. The data also demonstrates that tolerance of 2,4-D is stable for at least two generations.

TABLE 27

$T_1$ AAD-12 (v1) and untransformed control respone to varying levels of 2,4-D DMA.

| Herbicide | Lemont Untransformed Control | pDAB4101(20)003 | pDAB4101(27)002 |
|---|---|---|---|
| | Average % Injury 14 DAT | | |
| 1120 g ae/ha 2,4-D DMA | 20 | 10 | 10 |
| 2240 g ae/ha 2,4-D DMA | 35 | 15 | 30 |
| 4480 g ae/ha 2,4-D DMA | 50 | 23 | 40 |

21.7—Tissue Harvesting, DNA Isolation and Quantification.

Fresh tissue was placed into tubes and lyophilized at 4° C. for 2 days. After the tissue was fully dried, a tungsten bead (Valenite) was placed in the tube and the samples were subjected to 1 minute of dry grinding using a Kelco bead mill. The standard DNeasy DNA isolation procedure was then followed (Qiagen, Dneasy 69109). An aliquot of the extracted DNA was then stained with Pico Green (Molecular Probes P7589) and scanned in the fluorometer (BioTek) with known standards to obtain the concentration in ng/µl.

21.8—AAD-12 (v1) Expression.

Sample preparation and analysis conditions were as described previously. All 33 $T_0$ transgenic rice lines and 1 non-transgenic control were analyzed for AAD-12 expression using ELISA blot. AAD-12 was detected in the clones of 20 lines, but not in line Taipai 309 control plant. Twelve of the 20 lines that had some of the clones tolerant to imazethapyr were expressing AAD-12 protein, were AAD-12 PCR PTU positive, and AHAS coding region positive. Expression levels ranged from 2.3 to 1092.4 ppm of total soluble protein.

21.9—Field Tolerance of DDAB4101 Rice Plants to 2,4-D and Triclopyr Herbicides.

A field level tolerance trial was conducted with AAD-12 (v1) event pDAB4101[20] and one wild-type rice (Clearfield 131) at Wayside, Miss. (a non-transgenic imidazolinone-resistant variety). The experimental design was a randomized complete block design with a single replication. Herbicide treatments were 2× rates of 2,4-D (dimethylamine salt) at 2240 g ae/ha and triclopyr at 560 g ae/ha plus an untreated control. Within each herbicide treatment, two rows of $T_1$ generation pDAB4101[20] and two rows of Clearfield rice were planted using a small plot drill with 8-inch row spacing. The pDAB4101[20] rice contained the AHAS gene as a selectable marker for the AAD-12(v1) gene. Imazethapyr was applied at the one leaf stage as selection agent to remove any AAD-12 (v1) null plants from the plots. Herbicide treatments were applied when the rice reached the 2 leaf stage using compressed air backpack sprayer delivering 187 L/ha carrier volume at 130-200 kpa pressure. Visual ratings of injury were taken at 7, 14 and 21 days after application.

AAD-12 (v1) event response to 2,4-D and triclopyr are shown in Table 28. The non-transformed rice line (Clearfield) was severely injured (30% at 7DAT and 35% at 15DAT) by 2,4-D at 2240 g ae/ha which is considered the 4× commercial use rate. The AAD-12 (v1) event demonstrated excellent tolerance to 2,4-D with no injury observed at 7 or 15DAT. The non-transformed rice was significantly injured (15% at 7DAT and 25% at 15DAT) by the 2× rate of triclopyr (560 g ae/ha). The AAD-12 (v1) event demonstrated excellence tolerance to the 2× rates of triclopyr with no injury observed at either 7 or 15DAT.

These results indicate that the AAD-12 (v1) transformed rice displayed a high level of resistance to 2,4-D and triclopyr at rates that caused severe visual injury to the Clearfield rice. It also demonstrates the ability to stack multiple herbicide tolerance genes with AAD-12 I multiple species to provide resistance to a wider spectrum of effective chemistries Example 22—AAD-12 (v1) in Canola 22.1—Canola Transformation.

The AAD-12 (v1) gene conferring resistance to 2,4-D was used to transform *Brassica napus* var. Nexera* 710 with *Agrobacterium*-mediated transformation and plasmid pDAB3759. The construct contained AAD-12 (v1) gene driven by CsVMV promoter and Pat gene driven by AtUbi10 promoter and the EPSPS glyphosate resistance trait driven by AtUbi 10 promoter (see section 2.4).

Seeds were surface-sterilized with 10% commercial bleach for 10 minutes and rinsed 3 times with sterile distilled water. The seeds were then placed on one half concentration of MS basal medium (Murashige and Skoog, 1962) and maintained under growth regime set at 25° C., and a photoperiod of 16 hrs light/8 hrs dark.

Hypocotyl segments (3-5 mm) were excised from 5-7 day old seedlings and placed on callus induction medium K1D1 (MS medium with 1 mg/L kinetin and 1 mg/L 2,4-D) for 3 days as pre-treatment. The segments were then transferred into a petri plate, treated with *Agrobacterium* Z707S or LBA4404 strain containing pDAB3759. The *Agrobacterium* was grown overnight at 28° C. in the dark on a shaker at 150 rpm and subsequently re-suspended in the culture medium.

After 30 min treatment of the hypocotyl segments with *Agrobacterium*, these were placed back on the callus induction medium for 3 days. Following co-cultivation, the segments were placed on K1D1TC (callus induction medium containing 250 mg/L Carbenicillin and 300 mg/L Timentin) for one week or two weeks of recovery. Alternately, the segments were placed directly on selection medium K1D1H1 (above medium with 1 mg/L Herbiace). Carbenicillin and Timentin were the antibiotics used to kill the *Agrobacterium*. The selection agent Herbiace allowed the growth of the transformed cells.

Callused hypocotyl segments were then placed on B3Z1H1 (MS medium, 3 mg/L benzylamino purine, 1 mg/L Zeatin, 0.5 gm/L MES [2-(N-morpholino)ethane sulfonic acid], 5 mg/L silver nitrate, 1 mg/L Herbiace, Carbenicillin and Timentin) shoot regeneration medium. After 2-3 weeks shoots started regenerating. Hypocotyl segments along with the shoots are transferred to B3Z1H3 medium (MS medium, 3 mg/L benzylamino purine, 1 mg/L Zeatin, 0.5 gm/L MES [2-(N-morpholino) ethane sulfonic acid], 5 mg/L silver nitrate, 3 mg/L Herbiace, Carbenicillin and Timentin) for another 2-3 weeks.

Shoots were excised from the hypocotyl segments and transferred to shoot elongation medium MESH5 or MES10 (MS, 0.5 gm/L MES, 5 or 10 mg/L Herbiace, Carbenicillin, Timentin) for 2-4 weeks. The elongated shoots are cultured for root induction on MSI.1 (MS with 0.1 mg/L Indolebu-

TABLE 28

AAD-12 $T_1$ generation rice plants response to 2,4-D and triclopyr under field conditions.

| Herbicide Treatment | | % Visual Injury | | |
|---|---|---|---|---|
| | | 7DAT | | 15DAT | |
| Active Ingredient | Rate | AAD-12 event pDAB4101[20] | Wild-type Clearfield | AAD-12 event pDAB4101[20] | Wild-type Clearfield |
| 2,4-D | 2240 GM AE/HA | 0 | 15 | 0 | 35 |
| Triclopyr | 840 GM AE/HA | 0 | 30 | 0 | 25 |
| Untreated | | 0 | 0 | 0 | 0 | tyric acid). Once the plants had a well established root system, these were transplanted into soil. The plants were acclimated under controlled environmental conditions in the Conviron for 1-2 weeks before transfer to the greenhouse.

22.2—Molecular Analysis: Canola Materials and Methods 22.2.1—Tissue Harvesting DNA Isolation and Quantification.

Fresh tissue was placed into tubes and lyophilized at 4° C. for 2 days. After the tissue was fully dried, a tungsten bead (Valenite) was placed in the tube and the samples were subjected to 1 minute of dry grinding using a Kelco bead mill. The standard DNeasy DNA isolation procedure was then followed (Qiagen, DNeasy 69109). An aliquot of the extracted DNA was then stained with Pico Green (Molecular Probes P7589) and read in the fluorometer (BioTek) with known standards to obtain the concentration in ng/ul.

22.2.2—Polymerase Chain Reaction.

A total of 100 ng of total DNA was used as the template. 20 mM of each primer was used with the Takara Ex Taq PCR Polymerase kit (Mirus TAKRR001A). Primers for Coding Region PCR AAD-12 (v1) were (SEQ ID NO:10) (forward) and (SEQ ID NO: 11) (reverse). The PCR reaction was carried out in the 9700 Geneamp thermocycler (Applied Biosystems), by subjecting the samples to 94° C. for 3 minutes and 35 cycles of 94° C. for 30 seconds, 65° C. for 30 seconds, and 72° C. for 2 minutes followed by 72° C. for 10 minutes. PCR products were analyzed by electrophoresis on a 1% agarose gel stained with EtBr. 35 samples from 35 plants with AAD-12 (v1) events tested positive. Three negative control samples tested negative.

22.2.3—ELISA.

Using established ELISA described in previous section, AAD-12 protein was detected in 5 different canola transformation plant events. Expression levels ranged from 14 to over 700 ppm of total soluble protein (TSP). Three different untransformed plant samples were tested in parallel with no signal detected, indicating that the antibodies used in the assay have minimal cross reactivity to the canola cell matrix. These samples were also confirmed positive by Western analysis. A summary of the results is presented in Table 29.

TABLE 29

Expression of AAD-12 (v1) in Canola plants

| Sample # | [TSP] (µg/ml) | [AAD-12] (ng/ml) | Expression (ppm TSP) (ELISA) | Western |
|---|---|---|---|---|
| 31 | 5614.96 | 1692.12 | 301.36 | ++++ |
| 33 | 4988.26 | 2121.52 | 425.30 | ++++ |
| 38 | 5372.25 | 3879.09 | 722.06 | ++++ |
| 39 | 2812.77 | 41.36 | 14.71 | + |
| 40 | 3691.48 | 468.74 | 126.98 | +++ |
| Control 1 | 2736.24 | 0.00 | 0.00 | − |
| Control 2 | 2176.06 | 0.00 | 0.00 | − |
| Control 3 | 3403.26 | 0.00 | 0.00 | − |

22.4—Postemergence Herbicide Tolerance in AAD-12 (v1) Transformed $T_0$ Canola.

Forty-five $T_0$ events from the transformed with the construct pDAB3759, were sent to the greenhouse over a period of time and were allowed to acclimate in the greenhouse. The plants were grown until 2-4 new, normal looking leaves had emerged (i.e., plants had transitioned from tissue culture to greenhouse growing conditions). Plants were then treated with a lethal dose of the commercial formulations of 2,4-D Amine 4 at a rate of 560 g ae/ha. Herbicide applications were made with a track sprayer at a spray volume of 187 L/ha, 50-cm spray height. A lethal dose is defined as the rate that causes >95% injury to the untransformed controls.

Twenty-four of the events were tolerant to the 2,4-D DMA herbicide application. Some events did incur minor injury but recovered by 14 DAT. Events were progressed to the $T_1$ (and $T_2$ generation) by selfpollination under controlled, bagged, conditions.

22.5—AAD-12 (v1) Heritability in Canola.

A 100 plant progeny test was also conducted on 11 $T_1$ lines of AAD-12 (v1). The seeds were sown and transplanted to 3-inch pots filled with Metro Mix media. All plants were then sprayed with 560 g ae/ha 2,4-D DMA as previously described. After 14 DAT, resistant and sensitive plants were counted. Seven out of the 11 lines tested segregated as a single locus, dominant Mendelian trait (3R:1S) as determined by Chi-square analysis. AAD-12 is heritable as a robust aryloxyalkanoate auxin resistance gene in multiple species and can be stacked with one or more additional herbicide resistance genes.

22.6—Verification of High 2,4-D Tolerance in $T_1$ Canola

For $T_1$ AAD-12 (v1), 5-6 mg of seed were stratified, sown, and a fine layer of Sunshine Mix #5 media was added as a top layer of soil. Emerging plants were selected with 560 g ae/ha 2,4-D at 7 and 13 days after planting.

Surviving plants were transplanted into 3-inch pots containing Metro Mix media. Surviving plants from T1 progenies, that were selected with 560 g ae/ha 2,4-D, were also transplanted into 3-inch pots filled with Metro Mix soil. At 2-4 leaf stage plants were sprayed with either 280, 560, 1120, or 2240 g ae/ha 2,4-D DMA. Plants were graded at 3 and 14 DAT and compared to untransformed control plants. A sampling of $T_1$ event injury data 14DAT may be seen in Table 30. Data suggests that multiple events are robustly resistant to 2240 g ae/ha 2,4-D, while other events demonstrated less robust tolerance up to 1120 g ae/ha 2,4-D. Surviving plants were transplanted to 5¼" pots containing Metro Mix media and placed in the same growth conditions as before and self-pollinated to produce only homozygous seed.

TABLE 30

$T_1$ AAD-12 (v1) and untransformed control response to varying rates postemergence 2,4-D DMA applications.

| Herbicide | Untransformed Control | pDAB3759(33) 013.001 | pDAB3759(18) 009.001 | pDAB3759(18) 022.001 | pDAB3759(18) 030.001 | pDAB3759(18) 023.001 |
|---|---|---|---|---|---|---|
| | | | Average % Injury 14DAT | | | |
| 280 g ae/ha 2,4-D DMA | 85 | 0 | 0 | 0 | 0 | 0 |
| 560 g ae/ha 2,4-D DMA | 85 | 0 | 0 | 0 | 0 | 0 |

TABLE 30-continued

T₁ AAD-12 (v1) and untransformed control response to varying rates postemergence 2,4-D DMA applications.

| Herbicide | Untransformed Control | pDAB3759(33) 013.001 | pDAB3759(18) 009.001 | pDAB3759(18) 022.001 | pDAB3759(18) 030.001 | pDAB3759(18) 023.001 |
|---|---|---|---|---|---|---|
| | | | Average % Injury 14DAT | | | |
| 1120 g ae/ha 2,4-D DMA | 90 | 0 | 0 | 13 | 5 | 3 |
| 2240 g ae/ha 2,4-D DMA | 95 | 1 | 5 | 83 | 31 | 6 |

22.7—Field Tolerance of pDAB3759 Canola Plants to 2,4-D, Dichloprop, Triclopyr and Fluroxypyr Herbicides.

Field level tolerance trial was conducted on two AAD-12 (v1) events 3759(20)018.001 and 3759(18)030.001 and a wild-type canola (Nex710) in Fowler, Ind. The experimental design was a randomized complete block design with 3 replications. Herbicide treatments were 2,4-D (dimethylamine salt) at 280, 560, 1120, 2240 and 4480 g ae/ha, triclopyr at 840 g ae/ha, fluroxypyr at 280 g ae/ha and an untreated control. Within each herbicide treatment, single 20 ft row/event for event 3759(18)030.0011, 3759(18)018.001 and wild-type line (Nex710) were planted with a 4 row drill on 8 inch row spacing. Herbicide treatments were applied when canola reached the 4-6 leaf stage using compressed air backpack sprayer delivering 187 L/ha carrier volume at 130-200 kpa pressure. Visual injury ratings were taken at 7, 14 and 21 days after application.

Canola response to 2,4-D, triclopyr, and fluroxypyr are shown in Table 31. The wild-type canola (Nex710) was severely injured (72% at 14DAT) by 2,4-D at 2240 g ae/ha which is considered the 4× rate. The AAD-12 (v1) events all demonstrated excellent tolerance to 2,4-D at 14DAT with an average injury of 2, 3 and 2% observed at the 1, 2 and 4× rates, respectively. The wild-type canola was severely injured (25% at 14DAT) by the 2× rate of triclopyr (840 g ae/ha). AAD-12 (v1) events demonstrated tolerance at 2× rates of triclopyr with an average of 6% injury at 14DAT across the two events. Fluroxypyr at 280 g ae/ha caused severe injury (37%) to the non-transformed line at 14DAA. AAD-12 (v1) events demonstrated increased tolerance with an average of 8% injury at 5DAT.

These results indicate that AAD-12 (v1) transformed events displayed a high level of resistance to 2,4-D, triclopyr and fluroxypyr at rates that were lethal or caused severe epinastic malformations to non-transformed canola. AAD-12 has been shown to have relative efficacy of 2,4-D>triclopyr>fluroxypyr.

Example 23—AAD-12 (v1) Stacked with Insect Resistance (IR) or Other Input Traits in any Insect resistance in crops supplied by a transgenic trait is prevelant in corn and cotton production in North America and across the globe. Commercial products having combined IR and HT traits have been developed by multiple seed companies. These include Bt IR traits (e.g. Bt toxins listed at the website lifesci.sussex.ac.uk, 2006) and any or all of the HTC traits mentioned above. The value this offering brings is the ability to control multiple pest problems through genetic means in a single offering. The convenience of this offering will be restricted if weed control and insect control are accomplished independent of each other. AAD-12 (v1) alone or stacked with one or more additional HTC traits can be stacked with one or more additional input traits (e.g., insect resistance, fungal resistance, or stress tolerance, et al.) (isb.vt.edu/cfdocs/fieldtests1.cfm, 2005) either through conventional breeding or jointly as a novel transformation event. Benefits include the convenience and flexibility described in Examples 15-20 above, together with the ability to manage insect pests and/or other agronomic stresses in addition to the improved weed control offered by AAD-12 and associated herbicide tolerance. Thus, the subject invention can be used to provide a complete agronomic package of improved crop quality with the ability to flexibly and cost effectively control any number of agronomic issues.

Combined traits of IR and HT have application in most agronomic and horticultural/ornamental crops and forestry. The combination of AAD-12 and its commensurate herbicide tolerance and insect resistance afforded by any of the number of Bt or non-Bt IR genes are can be applied to the crop species listed (but not limited to) in Example 13. One skilled in the art of weed control will recognize that use of any of various commercial herbicides described in Examples 18-20, phenoxyacetic or pyridyloxyacetic auxin herbicides, alone or in multiple combinations, is enabled by AAD-12 (v1) transformation and stacking with the corresponding HT trait or IR trait either by conventional breeding or genetic

TABLE 31

AAD-12 (pDAB3759) canola plants response to 2,4-D, triclopyr, and fluroxypyr under field conditions.

| Herbicide Treatment | | % Visual Injury at 14 DAT | | |
|---|---|---|---|---|
| Active Ingredient | Rate | AAD-12 event 3759(20)018.001 | AAD-12 event 3759(18)030.001 | Wild Type (Nex710) |
| 2,4-D | 280 GM AE/HA | 0 a | 0 b | 0 e |
| 2,4-D | 560 GM AE/HA | 0 a | 0 b | 15 d |
| 2,4-D | 1120 GM AE/HA | 2 a | 2 ab | 33 bc |
| 2,4-D | 2240 GM AE/HA | 3 a | 3 ab | 48 a |
| Triclopyr | 840 GM AE/HA | 6 a | 6 ab | 25 cd |
| Fluroxypyr | 280 GM AE/HA | 7 a | 8 a | 37 ab |

Means with a column with different letters are significantly different as defined by LSD (p = 0.05).

engineering. Specific rates of other herbicides representative of these chemistries can be determined by the herbicide labels compiled in the CPR (Crop Protection Reference) book or similar compilation, labels compiled online (e.g., cdms.net/manuf/manuf.asp), or any commercial or academic crop protection guides such as the Crop Protection Guide from Agriliance (2005). Each alternative herbicide enabled for use in HTCs by AAD-12 (v1), whether used alone, tank mixed, or sequentially, is considered within the scope of this invention.

Example 24—AAD-12 (v1) as an In Vitro Dicot Selectable Marker

Genetic engineering of plant cell, tissue, organ, and plant or organelle such as plastid starts with the process of inserting genes of interest into plant cells using a suitable delivery method. However, when a gene is delivered to plant cells, only an extremely small percentage of cells integrate the heterogeneous gene into their genome. In order to select those few cells that have incorporated the gene of interest, researchers link a selectable or screenable "marker gene" to the gene of interest (GOI) in the vector. Cells that contain these markers are identified from the whole population of cells/tissue to which the DNA plasmid vector was delivered. By selecting those cells that express the marker gene, researchers are able to identify those few cells that may have incorporated the GOI into their genome.

There are a variety of selectable markers available to enable this selection process to obtain transgenic cells, callus, embryos, shoots and plantlets. The preferred selectable markers by the Ag-industry are herbicide markers that allow the ease of spraying compounds in the field to select the right transgenic progenies during the process of event sorting in the field situation. AAD-12 (v1) has been shown to efficiently serve as a selectable marker for whole plants transformed with the gene in the greenhouse and growth chamber (Example 7) with 2,4-D as the selection agent. Field selection is possible as well using 2,4-D in combination with the AAD-12 (v1) gene (Example 11, 22), but use in vitro for cell-level selection is complicated by the fact 2,4-D is used almost ubiquitously as a plant growth regulator in the plant tissue culture systems. Degradation of this important hormone by AAD-12 (v1) can impact he ability to use this gene as an in vitro selectable marker. Success of developing 2,4-D as a marker gene depends on identifying the right alternate plant growth regulator that can mimic the effect of 2,4-D in the respective culture system and at the same time possess the ability to be stable and not be degraded by the AAD-12 enzyme when expressed in the transgenic cells. R-dichlorprop is a close analog to 2,4-D that is not a substrate for AAD-12 (v1) and is used a non-metabolizable auxin substitute in tobacco cell cultures allowing 2,4-D to be used at high rates as a selection agent. This fact was used in exemplifying AAD-12 (v1) could be used as a selectable marker in vitro.

24.1—(Cell Culture-Alternative Auxins.

AAD-12 (v1) degrades 2,4-D, but not R-2,4-dichlorophenoxypropionic acid (R-dichlorprop), which has at the same time the structural requirement of an auxinic growth regulator. Other non-metabolizable plant auxin mimics that may be used in cell culture include NAA (naphthalene acetic acid), IAA (indole acetic acid), dicamba, picloram, and R-mecoprop. It was investigated if it was possible to substitute R-dichlorprop and successfully maintain two different tobacco cell cultures PHL (Petite Havanna) and BY2 suspensions. Conversely, for cotton explants R-dichlorprop, dicamba, and picloram were tested as alternative auxins and the embryogenic callus induction response in comparison to the standard growth regulator, 2,4-D was evaluated. Petite Havana tobacco (PHL) and Coker cotton cotyledons were used in their experiments.

24.1.1—Tobacco Cell Suspension-2,4-D as Selection Agent.

A dose response study was conducted with both the R-dichlorprop habituated PHL cells and the R-dichlorprop habituated BY2 cells where R-dichlorprop was substituted directly for 2,4-D in culture media. Though the focus was on PHL, a dose response was also done with BY2 in case of possible future studies, as well as to help predict the dose response for PHL. For the dichlorprop habituated PHL dose response, the levels of 2,4-D used (on LSBY2C medium with R-dichlorprop) were 0 (the control), 1, 2, 3, 5, 8, 10, 12, 15, 18, 20, 40, 60, 80, 10, 110, 120 mg/L 2,4-D. There were four replications per concentration. For the R-dichlorprop habituated BY2 dose response, the levels of 2,4-D used (on LSBY2C medium) were 0 (the control), 1, 2, 3, 5, 8, 10, 20, 30, 40, mg/L 2,4-D.

The dose response was carried out showed that all the concentration of 2,4-D tested were lethal above 10 mg/L concentrations. However, there was growth in all the concentrations up to 10-mg/L 2,4-D where a slight growth of PHL suspension was observed. The growth of the suspension colonies from 1-8 mg/L 2,4-D concentrations was comparable to the growth in control treatments. The observation made in BY2 suspension cells were similar except the concentration at 10 mg/L was found to be lethal and the sub lethal concentration was 8 mg/L concentration.

24.1.2—Tobacco Cell Transformation with AAD-12 (v1) and 2,4-D Selection.

For tobacco transformation experiment, there were 11 treatments altogether: a control set plated on LS-BY2C+ dichlorprop medium, and 10 sets of LSBY2C+dichlorprop+ 2,4-D at varying concentration levels (1, 2, 3, 5, 8, 10, 12, 15, 18, 20 mg/L). There were four replications per treatment. The plasmid DNA vector used was pDAB724, and the vector used for transformation was EHA101S strain of *Agrobacterium tumefaciens*. Four ml of PHL suspension at 0.6 OD$^{660}$ were mixed with 100 ul of *Agrobacterium* (either EHA101 or LBA4404 strains) suspension at 1.0 OD$^{660}$ in a sterile Petri plate and were mixed thoroughly and co-cultivated together in a non-shake condition at a dark growth chamber for 3 days at 25° C. After the co-cultivation period 1.5 ml of the Agro-tobacco suspension mixture was plated to the 11 set of plates above. The experiment was repeated with 13 treatments: a control of LS-BY2C+dichlorprop media (no 2,4-D), and LS-BY2C+dichlorprop+2,4-D (1, 2, 3, 5, 8, 10, 12, 15, 18, 20 mg/L); LSBY2C+1 mg/L 2,4-D+B10 (Bialophos); LSBY2C+10 2,4-D+B10+R-dichlorprop. Again, there were four replicates per treatment, as well as a positive and negative control. All media contain 500 mg/L Carbenicillin (C) to control to contain *Agrobacterium* growth in the selection media.

The plasmid used in these experiments is pDAB724 and it has PAT selectable marker as well. So, control transformation experiments were initiated using R-dichlorprop habituated PHL in the presence of 10 mg/L bialophos following the standard protocol described above. The treatments were done side by side with 4 replicates to see if the bialophos selection in these suspension is normal.

There was little growth observed in all selection concentrations of 2,4D tested above 10 mg/L; however several fast growing colonies were found in 2, 5, an 8 mg/L 2,4-D concentration and representative sample was transferred to fresh selection at 10 mg/L selection to bulk the callus. Also, several putative colonies were selected in from 12, 15, 18 and 20 mg/L 2,4-D, but when compared to 10 mg/L there were only few colonies in these selection plate. Control treatment conducted with bialophos selection showed normal colony development. It appears that 10 mg/L 2,4-D is the sub-lethal and above this concentration 2,4-D appears to be lethal to the non-transformed cells. All the identified colonies were transferred to fresh medium with 10 mg/L selection and were probed for the presence of transgene by PCR as described in Example 10. The colonies selected and bulked had the transgenes as determined by PCR and expression of the genes as established by the Western analyses (as described in example 10). Several colonies were identified as actively growing and transferred to fresh selection medium with 10 mg/L 2,4-D to bulk the callus.

The bulked calluses were then transferred to higher level of 2,4-D to test the tolerance level in vitro. The levels of 2,4-D used were 20, 40, 60, 80, 100, and 120 mg/L 2,4-D. However the callus did not grow beyond 20 mg/L 2, 4-D concentrations indicating a threshold concentration higher than 20 mg/L may exist.

24.2.1—Cotton Explants-Auxin Alternatives

A dose response study was initiated to test multiple auxin alternatives as a substitute for the use of 2,4-D as a growth regulator in cotton. The alternative auxin tested were 2,4-dichlorprop, dicamba, and picloram. These compounds were tested at 0.2, 2.0, and 20.0 uM concentrations respectively. 2,4-D was used as the control treatment at 0.02 uM concentration. The medium used is the base medium for cotton callus induction (Example 12). Beyond the initial phase of culture, auxin is removed from the medium to prod the tissue toward the regeneration process.

R-dichlorprop was not effective in callus induction of cotyledonary segments and appears toxic to cotton cells at the lowest concentration tested (0.02 uM). Dicamba effectively induces callus growth at all concentrations tested (0.02-20 uM) and has no apparent toxic effects in this concentration range. Callus induction with picloram increased up to a maximum when explants were treated with 0.2 uM to 20 uM. Quality of the callus was consistent with the standard 2,4-D treatment at the 2 uM picloram concentration. At the highest concentration (20 uM) 2,4-D was also inhibitory to cotton callus generation and growth.

Cotton has shown initial ability to respond effectively to alternative auxins (to 2,4-D) in culture. At high enough concentrations, 2,4-D is toxic to cotton cotyldeonary explants. R-dichlorprop is surprisingly significantly more toxic to cotton than 2,4-D or other auxins. 2,4-D may be used as a selection agent and in combination with AAD-12 (v1) as the selectable marker gene. Other non-metabolizable auxin surrogates (e.g., dicamba, picloram, R-mecoprop, NAA, or IAA) would allow the use of AAD-12 as a selectable marker in dicots with 2,4-D as the selection agent.

REFERENCES

Adang, M. J., M. J. Staver, T. A. Rocheleau, J. Leighton, R. F. Barker, and D. V. Thompson. 1985. Characterized full-length and truncated plasmid clones of the crystal protein of *Bacillus thuringiensis* subsp *kurstaki* HD-73 and their toxicity to *Manduca sexta*. Gene 36:289-300.

Agriliance Crop Protection Guide. 2005. Agriliance, LLC. St Paul, Minn. 614 p.

Altschul, S. F., W. Gish, W. Miller, E. W. Myers, and DJ. Lipman. 1990. Basic local alignment search tool. J. Mol. Biol. 215:403-410.

Altschul, S. F., T. L. Madden, A. A. Schaffer, J. Zhang, Z, Zhang, W. Miller, and DJ. Lipman. 1997. Gapped BLAST and PSIBLAST: a new generation of protein databasesearch programs. Nucl. Acids Res. 25:3389-3402.

An, G., B. D. Watson, S. Stachel, M. P. Gordon, E. W. Nester. 1985. New cloning vehicles for transformation of higher plants. EMBO J. 4:277-284.

Armstrong C. L., C. E. Green, R. L. Phillips. 1991. Development and availability of germplasm with high Type II culture formation response. Maize Genet Coop News Lett 65:92-93.

Beltz, G. A., K. A. Jacobs, T. H. Eickbush, P. T. Cherbas, and F. C. Kafatos. 1983 Methods of Enzymology, R. Wu, L. Grossman and K. Moldave [eds.] Academic Press, New York 100:266-285

Birch R. G. and T. Franks. 1991. Development and optimization of microprojectile systems for plant genetic transformation. Aust. J. Plant Physiol. 18:453-469.

CDMS. Crop Data Management Systems Labels and MSDS. Online. Internet. Mar. 13, 2004. Available at net/manuf/manuf.asp.

Chee P. P., K. A. Fober, J. L. Slightom. 1989. Transformation of soybean (*Glycine max*) by infecting germinating seeds with *Agrobacterium tumefaciens*. Plant Physiol. 91:1212-1218.

Cheng M., J. E. Fry, S. Pang, H. Zhou, C. M. Hironaka, D. R. Duncan, T. W. Conner, and Y. Wan. 1997. Genetic transformation of wheat mediated by *Agrobacterium tumefaciens*. Plant Physiol 115: 971-980.

Chu C. C., C. C. Wang, C. S. Sun, C. Hsu, K. C. Yin, C. Y. Chu, F. Y. Bi 1975.

Establishment of an efficient medium for anther culture of rice through comparative experiments on the nitrogen sources. Sci. Sinica 18:659-668.

Clemente T. E., B. J. LaVallee, A. R. Howe, D. Conner-Ward, R. J. Rozman, P. E. Hunter, D. L. Broyles, D. S. Kasten, M. A. Hinchee. 2000. Progeny analysis of glyphosate selected transgenic soybeans derived from *Agrobacterium*-mediated transformation. Crop Sci 40: 797-803.

CPR: Crop Protection Reference. 2005 Chemical and Pharmaceutical Press, New York, N.Y. 2647 p.

Devine, M. D. 2005. Why are there not more herbicide-tolerant crops?Pest Manag. Sci. 61:312-317.

Dietrich, Gabriele Elfriede (1998) Imidazolinone resistant AHAS mutants. U.S. Pat. No. 5,731,180.

Didierjean L, L. Gondet, R. Perkins, S. M. Lau, H. Schaller, D. P. O'Keefe, D. Werck-Reichhart. 2002. Engineering Herbicide Metabolism in Tobacco and *Arabidopsis* with CYP76B1, a Cytochrome P450 Enzyme from Jerusalem Artichoke. Plant Physiol 2002, 130:179-189.

Ditta, G. S. Stranfield, D. Corbin, and D. R. Helinski. 1980. Broad host range DNA cloning system for Gram-negative bacteria: Construction of a gene bank of *Rhizobium leliloti*. PNAS 77:7347-7351.

Edwards, R. A., L. H. Keller, and D. M. Schifferli. 1998. Improved allelic exchange vectors and their use to analyze 987P fimbria gene expression. Gene 207:149-157.

El-Shemy A, M. Teraishi, M. Khalafalla, T. Katsube-Tanaka, S. Utsumi, M. Ishimoto. 2004. Isolation of soybean plants with stable transgene expression by visual selection based on green fluorescent protein Molecular Breeding 14: 227-238.

El-Shemy A, M. Khalafalla, K. Fujita, M. Ishimoto. 2006. Molecular control of gene co-suppression of transgenic soybean. J. Biochem. and Mole. Biol. 39: 61-67.

Falco S. C., T. Guida, M. Locke, J. Mauvais, C. Sanders, R. T. Ward, P. Webber. 1995. Transgenic canola and soybean seeds with increased lysine. Bio/Technology 13:577-582.

Finer J. and M. McMullen. 1991. Transformation of soybean via particle bombardment of embryogenic suspension culture tissue. In Vitro Cell. Dev. Biol. 27P: 175-182.

Fraley, R. T., D. G. Rogers, and R. B. Horsch. 1986. Genetic transformation in higher plants. Crit. Rev. Plant Sci. 4:1-46.

Frame B. R., P. R. Drayton, S. V. Bagnall, C. J. Lewnau, W. P. Bullock, H. M. Wilson, J. M. Dunwell, J. A. Thompson, and K. Wang. 1994. Production of fertile maize plants by silicon carbide whisker-mediated transformation. Plant J. 6:941-948.

Fukumori, F., and R. P. Hausinger. 1993. Purification and characterization of 2,4-dichlorophenoxyacetate/α-ketoglutarate dioxygenase. J. Biol. Chem. 268: 24311-24317.

Gamborg, O. L., R. A. Miller, and K. Ojima. 1968. Nutrient requirements of suspensions of cultures of soybean root cells. Exp. Cell Res. 50:151-158.

Gay, P., D. Le Coq, M. Steinmetz, E. Ferrari, and J. A. Hoch. 1983. Cloning structural gene sacB, which codes for exoenzyme levansucrase of *Bacillus subtilis*: expression of the gene in *Eschericia coli*. J. Bacteriol. 153:1424-1431.

Gianessi, L. R. 2005 Economic and herbicide use impacts of glyphosate-resistant crops. Pest. Manag. Sci. 61:241-245.

Heap, I. The International Survey of Herbicide Resistant Weeds. Online. Internet. Mar. 18, 2005. Available at weedscience.com.

Hiei Y., T. Komari, and T. Kubo. 1997. Transformation of rice mediated by *Agrobacterium tumefaciens*, Plant Mol. Biol. 35:205-218.

Hiei, Y., T. Komari (1997) Method for Transforming Monocotyledons. U.S. Pat. No. 5,591,616.

Hinchee M. A. W., D. V. Conner-Ward, C. A. Newell, R. E. McDonnell, S. J. Sato, C. S. Gasser, D. A. Fischhoff, D. B. Re, R. T. Fraley, R. B. Horsch. 1988. Production of transgenic soybean plants using *Agrobacterium*-mediated DNA transfer. Bio/Technology 6:915-922.

Höfte, H. and H. R. Whiteley. 1989. Insecticidal cristal proteins of *Bacillus thuringiensis*. 1989. Microbiol. Rev. 53:242-255.

Hoekema, A. 1985. In: The Binary Plant Vector System, Offset-durkkerij Kanters B.V., Alblasserdam, Chapter 5.

Hogan, D. A.; S. R. Smith, E. A. Saari, J. McCracken, R. P. Hausinger. 2000. Site-directed mutagenesis of 2,4-dichlorophenoxyacetic acid/α-ketoglutarate dioxygenase. Identification of residues involved in metallocenter formation and substrate binding. J. Biol. Chem. 275:12400-12409.

Holsters, M., D. De Waele, A. Depicker, E. Messens, M. Van Montagu, and J. Schell. 1978. Transfection and transformation of *Agrobacterium tumefaciens*. Mol Gen. Genet. 163:181-187.

Horsch, R., J. Fry, N. Hoffman, J. Neidermeyer, S. Rogers, and R. Fraley. 1988. In Plant Molecular Biology Manual, S. Gelvin et al., eds., Kluwer Academic Publishers, Boston Horvath, M., G. Ditzelmüller, M. Lodl, and F. Streichsbier. 1990. Isolation and characterization of a 2-(2,4-dichlorophenoxyl)propionic acid-degrading soil bacterium. Appl. Microbiol Biotechnol. 33:213-216.

Jefferson, R. A. M. Bevan, and T. Kavanagh. 1987. The use of *Escherichia coli* β-glucuronidase gene as a gene fusion marker for studies of gene expression in higher plants. Biochem. Soc. Trans. 15: 17-19.

Karlin, S. and S. F. Altschul. 1990. Methods for assessing the statistical significance of molecular sequence features by using general scoring schemes. PNAS 87:2264-2268.

Karlin, S. and S. F. Altschul. 1993. Applications and statistics for multiple high-scoring segments in molecular sequences. PNAS 90:5873-5877

Keller, G. H., and M. M. Manak. 1987. DNA Probes. Stockton Press, New York, N.Y., pp. 169-170.

Khalafalla M, S. Rahman, H. El-Shemy, Y. Nakamoto, K. Wakasa, M. Ishimoto. 2005. Optimization of particle bombardment conditions by monitoring of transient sGFP (S65T) expression in transformed soybean. Breeding Sci. 55:257-263.

Khan M, L. Table, L. Heath, D. Spencer, T. Higgins. 1994. *Agrobacterium*-mediated transformation of subterranean clover (*Trifolium subterraneum* L.). Plant Physiol 105: 81-88.

Kohler, H. P. E. 1999. *Delftia acidovorans* MH: a versatile phenoxyalkanoic acid herbicide degrader. J. Ind Microbiol and Biotech. 23:336-340.

Li L, Qu R, Kochko A de, Fauquet C M, Beachy R N (1993) An improved rice transformation system using the biolistic method. Plant Cell Rep 12:250-255

Linsmaier, E. M. and F. Skoog (1965) Organic growth factor requirements of tobacco tissue cultures. Physiol. Plant. 18:100-127.

Lorraine-Colwill, D. F., S. B. Powles, T. R. Hoawkes, P. H. Hollingshead, S. A. J. Arner, and C. Preston. 2003. Investigations into the mechanism of glyphosate resistance in *Lolium rigidum*. Pestic. Biochem. Physiol. 74:62-73.

Luo, H., Q. Hu, K. Nelson, C. Longo, A. P. Kausch, J. M. Chandlee, J. K. Wipff and C. R. Fricker. 2004. *Agrobacterium tumefaciens*-mediated creeping bentgrass (*Agrostis stolonifera* L.) transformation using phosphinothricin selection results in a high frequency of single-copy transgene integration. Plant Cell Reports 22: 645-652.

Lyon, B. R., D. J. Llewellyn, J. L. Huppatz, E. S. Dennis, and W. J. Peacock. 1989. Expression of a bacterial gene in transgenic tobacco confers resistance to the herbicide 2,4-dichlorophenoxyacetic acid. Plant Mol. Bio. 13:533-540.

Lyon, B. R., Y. L. Cousins, D. J. Llewellyn, and E. S. Dennis. 1993. Cotton plants transformed with a bacterial degradation gene are protected from accidental spray drift damage by the herbicide 2,4-dichlorophenoxyacetic acid. Transgenic Res. 2: 166-169.

Maniatis, T., E. F. Fritsch, J. Sambrook. 1982. *Molecular Cloning: A Laboratory Manual*, Cold Spring Harbor Laboratory, Cold Spring Harbor, N.Y.

Martin, J. R. and W. W. Witt. 2002. Response of glyphosate tolerant and susceptible biotypes of horseweed (*Conyza canadensis*) to foliar applied herbicides. Proc. North Cent. Weed Sci. Soc. 57:185.

Martinell B. J., L. S. Julson, C. A. Emler, H. Yong, D. E. McCabe, E. J. Williams. 2002. Soybean *Agrobacterium* transformation method. U.S. Pat. No. 6,384,301

McCabe D. E., W. F. Swain, B. J. Martinell, P. Christou. 1988. Stable transformation of soybean (*Glycine max*) by particle acceleration. Bio/Technology 6:923-926.

Miller S. D., P. W. Stahlman, P. Westra, G. W. Wicks, R. G. Wilson, J. M. Tichota. 2003. Risks of weed spectrum shifts and herbicide resistance in glyphosate-resistant cropping systems. Proc. West. Soc. Weed Sci. 56:61-62.

Muller R, S. Jorks, S. Kleinsteuber, W. Babel. 1999. *Comamonas acidovorans* strain MC1: a new isolate capable of degrading the chiral herbicides dichlorprop and mecoprop and the herbicides 2,4-D and MCPA. Microbiol. Res. 154:241-246.

Muller T, S. Byrde, C. Werlen, J. Roelof van der Meer, H-P. Kohler. 2004. Genetic Analysis of Phenoxyalkanoic Acid Degradation in *Sphingomonas herbicidovorans* MH. Appl. Environ. Microbiol. 70(10):6066-6075.

Muller T, T. Fleischmann, J. Roelof van der Meer, H-P. Kohler. 2006. Purification and Characterization of Two Enantioselective α-Ketoglutarate-Dependent Dioxygenases, RdpA and SpdA from *Sphingomonas herbicidovorans* MH. Appl. Environ. Microbiol. 72(7):4853-4861.

Muller T, M. Zavodszky, M. Feig, L. Kuhn, R. Hausinger. 2006. Structural basis for the enantiospecificities of R- and S-specific phenoxyproprionate/α-ketoglutarate dioxygenases. Protein Sci. 15:1356-1368.

Murashige T. and F. Skoog. 1962. A revised medium for rapid growth and bioassays with tobacco tissue cultures. Physiol. Plant. 15:473-497.

Murphy G. P., T. E. Dutt, R. F. Montgomery, T. S. Willard, G. A. Elmore. 2002. Control of horseweed with glyphosate. Proc. North Cent. Weed Sci. Soc. 57:194.

Ng, C. H., R. Wickneswari, S. Salmigah, Y. T. Teng, and B. S. Ismail. 2003. Gene polymorphisms in glyphosate-resistant and -susceptible biotypes of *Eleusine indica* from Malaysia. Weed Res. 43:108-115.

Olhoft P. M. and D. A. Somers. 2001. L-Cysteine increases *Agrobacterium*-mediated T-DNA delivery into soybean cotyledonary-node cells. Plant Cell Rep 20: 706-711

Olhoft, P. M., L. E. Flagel, C. M. Donovan, and D. A. Somers. 2003. Efficient soybean transformation using hygromycin B selection in the cotyledonary-node method. Planta 216:723-735

Padgette S. R., K. H. Kolacz, X. Delannay, D. B. Re, B. J. LaVallee, C. N. Tinius, W. K. Rhodes, Y. I. Otero, G. F. Barry, D. A. Eichholtz, V. M. Peschke, D. L. Nida, N. B. Taylor, and G. M. Kishore. 1995. Development, identification, and characterization of a glyphosate-tolerant soybean line. Crop Sci. 1995; 35:1451-1461.

Parrott W. A., J. N. All, M. J. Adang, M. A. Bailey, H. R. Boerma, and C. N. Stewart, Jr. 1994. Recovery and evaluation of soybean plants transgenic for a *Bacillus thuringiensis* var. *kurstaki* insecticidal gene. In Vitro Cell. Dev. Biol. 30P:144-149.

Popelka, J. C. and F. Altpeter 2003. *Agrobacterium tumefaciens*-mediated genetic transformation of rye (*Secale cereale* L) Mol. Breed 11:203-211

Powles, S. B. and C. Preston. 2006. Evolved glyphosate resistance in plants: biochemical and genetic basis of resistance. Weed Tech 20:282-289.

Saari, R. E., D. A. Hogan, and R. P. Hausinger. 1999. Stereospecific degradation of the pheonxypropionate herbicide dichlorprop. J. Mol. Catal. B: Enz. 6:421-428.

Saiki, R. K., S. Scharf, F. Faloona, K. B. Mullis, G. T. Horn, H. A. Erlich, and N. Arnheim. 1985. Enzymatic Amplification of β-Globin Genomic Sequences and Restriction Site Analysis for Diagnosis of Sickle Cell Anemia. *Science* 230:1350-1354.

Sambrook, J., E. F. Fritsch, and T. Maniatis. 1989. Molecular Cloning, A Laboratory Manual, Cold Spring Harbor Press.

Sambrook, J. and D. W. Russell 2000. *Molecular Cloning*. Cold Spring Harbor Laboratory Press, Cold Spring Harbor, N.Y.

Schenk, R. U. and A. C. Hildebrandt (1972) Methods and techniques for induction and growth of monocotyledenous and dicotyledenous plant cell cultures. Can. J. Bot. 50:199-204.

Sfiligoj, E. 2004. Spreading resistance. Crop Life. March issue.

Simarmata, M., J. E. Kaufmann, and D. Penner. 2003. Potential basis of glyphosate resistance in California rigid ryegrass (*Lolium rigidum*). Weed Sci. 51:678-682.

Singh R. J., T. M. Klein, C. J. Mauvais, S. Knowlton, T. Hymowitz, C. M. Kostow. Cytological characterization of transgenic soybean. Theor. Appl. Genet. 1998; 96:319-324.

Smejkal, C. W., T. Vallaeys, S. K. Burton, and H. M. Lappin-Scott. 2001. Substrate specificity of chlorophenoxyalkanoic acid-degrading bacteria is not dependent upon phylogenetically related tfdA gene types. Biol. Fertil. Sols 33:507-513.

Streber, W. and L. Willmitzer. 1989. Transgenic tobacco plants expressing a bacterial detoxifying enzyme are resistant to 2,4-D. Bio/Technology 7:811-816.

Streber, W. R., K. N. Timmis, and M. H. Zenk. 2000. Microorganisms and plasmids for 2,4-dichlorophenoxyacetic acid (2,4-D) monooxygenase formation and process for the production of these plasmids and strains. U.S. Pat. No. 6,153,401.

Streber, W. R., K. N. Timmis, and M. H. Zenk. 1987. Analysis, cloning, and high-level expression of 2,4-dichlorophenixyacetic monooxygenase gene tfdA of *Alcaligenes eutrophus* JMP 134. J. Bacteriol. 169:2950-2955.

Suggs, S. V., T. Miyake, E. H. Kawashime, M. J. Johnson, K. Itakura, and R. B. Wallace. 1981. *ICN-UCLA Symp. Dev. Biol. Using Purified Genes*, D. D. Brown [ed.], Academic Press, New York, 23:683-693.

Terakawa T, H. Hisakazu, Y. Masanori 2005. Efficient whiskermediated gene transformation in a combination with supersonic treatment. Breeding science 55: 456-358.

Tingay, S., D. McElroy, R. Kalla, S. Fieg, W. Mingbo, S. Thornton, and R. Bretell. 1997. *Agrobacterium tumefaciens*-mediated barley transformation. Plant J. 11:1369-1376.

Weigel, D. and J. Glazebrook. 2002. *Arabidopsis*: A Laboratory Manual. Cold Spring Harbor Lab Press, Cold Spring Harbor, N.Y. 358 pp.

Weising, K., J. Schell, and G. Kahl. 1988. Foreign genes in plants: transfer, structure, expression and applications. Ann. Rev. Genet. 22:421-477.

Welter, M. E., D. S. Clayton, M. A. miler, and J. F. Petolino. 1995. Morphotypes of friable embryogenic maize callus. Plant Cell Rep. 14:725-729.

Westendorf A., D. Benndorf, R. Muller, W. Babel. 2002. The two enantiospecific dichlorprop/α-ketoglutarate-dioxygenases from *Delftia acidovorans* MC1-protein and sequence data of Rdpa and SdpA. Microbiol. Res. 157: 317-22.

Westendorf, A., R. H. Muller, and W. Babel. 2003. Purification and characterization of the enantiospecific dioxygenases from *Delftia acidovorans* MC1 initiating the degradation of phenoxypropionates and phenoxyacetate herbicides. Acta Biotechnol. 23: 3-17.

WSSA. 2002. Herbicide Handbook (8$^{th}$ ed). Weed Science Society of America. Lawrence, Kans. 492 pp.

Zeng P, D. Vadnais, Z. Zhang, and J. Polacco. 2004. Refined glufosinate selection in *Agrobacterium*-mediated transformation of soybean [*Glycine max* (L.) Merr.]. Plant Cell Rep. 22: 478-482.

Zhang S (1995) Efficient plant regeneration from indica (group 1) rice protoplasts of one advanced breeding line and three varieties. Plant Cell Rep 15:68-71

Zhang S, Chen L, Qu R, Marmey P, Beachy R N, Fauquet C M (1996) Efficient plant regeneration from indica (group 1) rice protoplasts of one advanced breeding line and three varieties. Plant Cell Rep 15:465-469.

Zhang S, Song W, Chen L, Ruan D, Taylor N, Ronald P, Beachy R N, Fauquet C M (1998) Transgenic elite Indica rice varieties, resistant to *Xanthomonas oryzae* pv. *oryzae*. Mol Breed 4:551-558.

Zhang, Z., A. Xing, P. E. Staswick, and T. E. Clemente. 1999. The use of glufosinate as a selective agent in *Agrobacterium*-mediated transformation of soybean. Plant Cell, Tissue, and Organ Culture 56:37-46.

Zhao, Z. Y., T. Cai, L. Tagliani, M. Miller, N. Wang, H. Pang, M. Rudert, S. Schroeder, D. Hondred, J. Seltzer, and D. Pierce. 2000. *Agrobacterium*-mediated *sorghum* transformation, Plant Mol. Biol. 44:789-798.

Zipper, C., M. Bunk, A. Zehnder, H. Kohler. 1998. Enantioselective uptake and degradation of the chiral herbicide dichlorprop [(RS)-2-(2,4-dichlorophenoxy) propanoic acid] by *Delftia acidovorans* MH. J. Bact. 13:3368-3374

---

We claim:

1. An expression cassette for expression in a plant cell, comprising a polynucleotide operably linked to a heterologous plant promoter or a plant virus promoter, wherein said polynucleotide encodes a protein that catalyzes degradation of phenoxy auxin and pyridyloxy auxin herbicides, wherein the polynucleotide that encodes said protein comprises SEQ ID NO:3.

2. The expression cassette of claim 1, wherein said polynucleotide comprises plant codons for expression in said plant cell.

3. The expression cassette of claim 1, wherein said plant promoter or said plant virus promoter is selected from a cassava vein mosaic virus promoter, a CaMV 35S promoter, a Figwort Mosaic Virus promoter, a rice actin promoter, a phaseolin promoter, an *Arabidopsis thaliana* Ubiquitin 10 promoter, a maize ubiquitin promoter, an *Arabidopsis thaliana* Act2 promoter, an *Arabidopsis thaliana* Ubiquitin 11 promoter, and an *Arabidopsis thaliana* Ubiquitin 3 promoter.

4. A method of controlling herbicide resistance in weeds in a field, wherein said method comprises applying to said weeds at least one herbicide selected from the group consisting of a pyridyloxy auxin herbicide and a phenoxy auxin herbicide, said field comprising a plurality of crop plants comprising the expression cassette of claim 1.

5. A method of selecting at least one transgenic plant that is resistant or tolerant to both phenoxy auxin and pyridyloxy auxin herbicides, said method comprising applying a herbicidically effective amount of an aryloxyalkanoate herbicide to a plurality of plants in a field, wherein said plurality of plants in said field comprises at least one plant that is stably transformed with the expression cassette of claim 1 and is able to grow in said effective amount of the aryloxyalkanoate herbicide, and identifying said plant that is stably transformed with said expression cassette.

6. The method of claim 4, wherein said plurality of crop plants are dicots.

7. The method of claim 6, wherein said dicots are selected from the group consisting of soybean plants, cotton plants, canola plants, sugar beet plants, tomato plants, and sunflower plants.

8. The method of claim 4, wherein said method comprises applying to said weeds at least one herbicide selected from the group consisting of a pyridyloxy auxin herbicide and a phenoxy auxin herbicide, and wherein said pyridyloxy auxin herbicide comprises one or more pyridyloxyacetate herbicides.

9. The method of claim 8, wherein said pyridyloxyacetate herbicide(s) is selected from the group consisting of triclopyr and fluroxypyr.

10. The method of claim 4, wherein said applying step comprises applying said herbicide to said crop plants within 14 days of planting a seed in said field, wherein said seed comprises an expression cassette comprising a polynucleotide operably linked to a heterologous plant promoter or a plant virus promoter, wherein said polynucleotide encodes a protein that catalyzes degradation of phenoxy auxin and pyridyloxy auxin herbicides, wherein the polynucleotide that encodes said protein comprises SEQ ID NO:3.

11. The method of claim 4, wherein said plurality of crop plants further comprises a second polynucleotide encoding a second protein that confers said crop plants with resistance to at least one other herbicide, wherein said second polynucleotide is heterologous, and said method further comprises applying said at least one other herbicide to least a portion of said field.

12. The method of claim 11, wherein said herbicides are applied sequentially or concurrently.

13. The method of claim 11, wherein said herbicides are applied from a tank mix.

14. The method of claim 11, wherein said at least one other herbicide is selected from the group consisting of acetochlor, acifluorfen, alloxydim, amidosulfuron, aminopyralid, atrazine, beflubutamid, bispyribac, butafenacil, cafenstrole, carfentrazone, chlorimuron, chlorotoluron, cinidonethyl, clethodim, clodinafop, clomazone, cloproxydim, clopyralid, cloransulam, cyanazine, cyclosulfamuron, cycloxydim, cyhalofop, daimuron, dicamba, diclofop, diclosulam, diflufenican, dimethenamid, diquat, dithiopyr, diuron, ethalfluralin, fenoxaprop, flazasulfuron, florasulam, fluazifop, flucarbazone, flufenacet, flufenican, flufenpyr, flumetsulam, flumiclorac, flumioxazin, fluroxypyr, fluthiacet, fomesafen, foramsulfuron, glufosinate, glyphosate, halosafen, halosulfuron, haloxyfop, imazamethabenz, imazamox, imazapic, imazapyr, imazaquin, imazethapyr, imazosulfuron, iodosulfuron, ioxynil, isoxaben, isoxaflutole, lactofen, linuron, mefenacet, mefluidide, mesosulfuron, mesotrione, metamifop, metazachlor, metosulam, metribuzin, MSMA, napropamide, nicosulfuron, norflurazon, oryzalin, oxadiazon, oxyfluorfen, paraquat, pebulate, pendimethalin, penoxsulam, picloram, picolinafen, pinoxaden, primisulfuron, profoxydim, propanil, pyraflufen, pyrazosulfuron, pyribenzoxim, pyriminobac, pyrithiobac, pyroxasulfone, pyroxsulam, quinclorac, quinmerac, quizalofop, rimsulfuron, sethoxydim, simazine, sulcotrione, sulfentrazone, sulfometuron, tefuryltrione, tembotrione, tepraloxydim, terbacil, thiazopyr, thidiazuron, thiencarbazone, thifensulfuron, thiobencarb, topramezone, tralkoxydim, triasulfuron, tribenuron, triclopyr, trifloxysulfuron, trifluralin, triflusulfuron, and tritosulfuron.

15. The method of claim 4, wherein said weeds are glyphosate-resistant.

16. The method of claim 15, wherein said crop plants are glyphosate tolerant crop plants.

17. The method of claim 4, wherein said herbicide is the phenoxy auxin herbicide.

18. The method of claim 17, wherein said phenoxy auxin is selected from the group consisting of MCPA and a 2,4-D herbicide.

19. A method of controlling volunteer plants in a field, wherein said method comprises applying to said volunteer plants at least one herbicide selected from the group consisting of a pyridyloxy auxin herbicide and a phenoxy auxin herbicide, said field comprising a plurality of transgenic crop plants comprising the expression cassette of claim 1.

20. The method of claim 19 wherein said volunteer plants are glyphosate-resistant and of a different species than said transgenic crop plants.

21. A polynucleotide operably linked to a heterologous plant promoter or a plant virus promoter, wherein the polynucleotide encodes a protein having aryloxyalkanoate dioxygenase activity, wherein the protein enzymatically degrades phenoxy auxin and pyridyloxy auxin herbicides, and wherein the polynucleotide that encodes said protein comprises SEQ ID NO:3.

22. A polynucleotide optimized for expression in a plant wherein said polynucleotide is operably linked to a heterologous plant promoter or a plant virus promoter, wherein the polynucleotide encodes a protein having aryloxyalkanoate dioxygenase activity, wherein the protein enzymatically degrades phenoxy auxin and pyridyloxy auxin herbicides, and wherein the polynucleotide that encodes said protein has SEQ ID NO:3.

23. The polynucleotide of claim 22 wherein said polynucleotide is optimized for expression in a dicotyledonous plant or a monocotyledonous plant.

24. An isolated polynucleotide that is operably linked to a heterologous plant promoter or a plant virus promoter, wherein the polynucleotide encodes a protein that enzymatically degrades phenoxy auxin and pyridyloxy auxin herbicides, and wherein the polynucleotide that encodes said protein comprises SEQ ID NO:3.

25. The polynucleotide of claim 24 wherein said promoter is a cassava vein mosaic virus promoter.

* * * * *